United States Patent
Ying et al.

(10) Patent No.: US 11,701,657 B2
(45) Date of Patent: Jul. 18, 2023

(54) COLUMN-BASED DEVICE FOR RETRIEVAL OF RARE CELLS BASED ON SIZE, AND USES THEREOF

(71) Applicant: Agency for Science, Technology and Research, Singapore (SG)

(72) Inventors: Jackie Y. Ying, Singapore (SG); Min-Han Tan, Singapore (SG); Yoke San Daniel Lee, Singapore (SG); Igor Cima, Singapore (SG); Yeon Joon Park, Singapore (SG); Wai Min Phyo, Singapore (SG)

(73) Assignee: AGENCY FOR SCIENCE, TECHNOLOGY AND RESEARCH, Singapore (SG)

(*) Notice: Subject to any disclaimer, the term of this patent is extended or adjusted under 35 U.S.C. 154(b) by 49 days.

(21) Appl. No.: 17/077,828

(22) Filed: Oct. 22, 2020

(65) Prior Publication Data

US 2021/0106997 A1   Apr. 15, 2021

Related U.S. Application Data

(62) Division of application No. 15/544,761, filed as application No. PCT/SG2016/050027 on Jan. 21, 2016, now Pat. No. 11,084,034.

(30) Foreign Application Priority Data

Jan. 21, 2015 (SG) ............... 10201500471Q
Jan. 21, 2015 (SG) ............... 10201500472R

(51) Int. Cl.
*B01L 3/00* (2006.01)
*C12N 5/071* (2010.01)
(Continued)

(52) U.S. Cl.
CPC ........ *B01L 3/502761* (2013.01); *C12N 5/069* (2013.01); *C12Q 1/6886* (2013.01);
(Continued)

(58) Field of Classification Search
CPC ............................... B01L 2300/0681
See application file for complete search history.

(56) References Cited

U.S. PATENT DOCUMENTS 4,915,848 A   4/1990 Carmen et al.
8,889,361 B2   11/2014 Chen
(Continued)

FOREIGN PATENT DOCUMENTS

CN   102 304 581 B   10/2013
FR   2926091 A1   7/2009
(Continued)

OTHER PUBLICATIONS

Siyang Zheng et al., "3D microfilter device for viable circulating tumor cell (CTC) enrichment from blood", Feb. 2011, Biomed Microdevices (Year: 2011).*
(Continued)

*Primary Examiner* — Jennifer Wecker
*Assistant Examiner* — Mickey Huang
(74) *Attorney, Agent, or Firm* — Marshall, Gerstein & Borun LLP

(57) ABSTRACT

A column-based device and method for retrieving cells of interest were enclosed. The said device comprises a column comprising (i) an inner wall defining an inner chamber with inlet and outlet openings, (ii) a perforated plug disposed adjacent to the outlet opening, (iii) a sleeve insert with a channel and disposed within the chamber and adjacent to the perforated plug, and (iv) a filtering means housed within sleeve insert sandwiched between two sealing means. In particular, Tumor-derived endothelial cell clusters (TECCs)
(Continued)

as characterized multiple nuclei, expression of endothelial markers (PECAM1, VWF and CDH5), and non-expression of leukocyte, megakaryocyte and platelets markers, may be retrieved using the disclosed device. Also encompassed are methods, reagents and kits for the diagnosis and prognosis of cancers by detecting for the presence of TECCs isolated from blood samples using the claimed device.

12 Claims, 16 Drawing Sheets

Specification includes a Sequence Listing.

(51) Int. Cl.
    G01N 33/50     (2006.01)
    G01N 33/574    (2006.01)
    C12Q 1/6886    (2018.01)
(52) U.S. Cl.
    CPC ..... *G01N 33/5064* (2013.01); *G01N 33/5094* (2013.01); *G01N 33/574* (2013.01); *G01N 33/57419* (2013.01); *G01N 33/57492* (2013.01); *B01L 2200/027* (2013.01); *B01L 2200/0647* (2013.01); *B01L 2300/042* (2013.01); *B01L 2300/0681* (2013.01); *C12Q 2600/156* (2013.01)

(56) References Cited

U.S. PATENT DOCUMENTS

| | | |
|---|---|---|
| 2007/0215533 A1 | 9/2007 | Tittgen |
| 2009/0191535 A1 | 7/2009 | Connelly et al. |
| 2013/0122539 A1 | 5/2013 | Li et al. |
| 2014/0315295 A1 | 10/2014 | Makarova et al. |
| 2014/0322743 A1 | 10/2014 | Tang et al. |
| 2018/0008982 A1 | 1/2018 | Ying et al. |

FOREIGN PATENT DOCUMENTS

| | | |
|---|---|---|
| FR | 2926091 B1 | 9/2014 |
| JP | 2012-044876 A | 3/2012 |
| WO | WO-2005/105256 A1 | 11/2005 |
| WO | WO-2007/121464 A2 | 10/2007 |
| WO | WO-2009/038754 A2 | 3/2009 |
| WO | WO-2014/023765 A2 | 2/2014 |
| WO | WO-2015/088979 A1 | 6/2015 |
| WO | WO-2015/116780 A1 | 8/2015 |

OTHER PUBLICATIONS

Tang et al. "Microfluidic device with integrated microfilter of conical-shaped holes for high efficiency and high purity capture of circulating tumor cells", 2014, Scientific Reports (Year: 2014).*
Quilici et al., "Circulating Endothelial Cell Count as a Diagnostic Marker for Non-ST-Elevation Acute Coronary Syndromes", Circulation, 2004, 110, pp. 1586-1591.
Thompson et al., "Chromosomes and Cancer Cells", Chromosome Res. 19(3), Apr. 2011, 16 pages.
Gisselsson et al., "Abnormal Nuclear Shape in Solid Tumors Reflects Mitotic Instability", American Journal of Pathology, vol. 158, No. 1, Jan. 2001, pp. 199-206.
Written Opinion in SG Application No. 10201804421X dated Sep. 26, 2022, 11 pages.
Alessandri, G. et al., Phenotypic and functional characteristics of tumour-derived microvascular endothelial cells, Clinical & Experimental Metastasis, 17(8): 655-662 (1999).
Bertolini, F. et al., The multifaceted circulating endothelial cell in cancer: towards marker and target identification, Nature Reviews, 6(11): 835-845 (2006).
Bethel, K. et al., Fluid phase biopsy for detection and characterization of circulating endothelial cells in myocardial infarction, Phys. Biol., 11(16002): 1-9 (2014).
Blann, A.D. et al., Circulating endothelial cell. Biomarker of vascular disease., Thromb Haemost, 93(2): 228-235 (2005).
Cima, I. et al., Tumor-derived circulating endothelial cell clusters in colorectal cancer, Science Translational Medicine, 8(345): 345ra89 1-11 (2016).
Damani, S. et al., Characterization of Circulating Endothelial Cells in Acute Myocardial Infarction, Sci Transl Med, 4(126): 126ra33 1-20 (2012).
Desitter, I. et al., a new device for rapid isolation by size and characterization of rare circulating tumor cells, Anticancer Res., 31 (2): 427-441 (2011).
Dome, B. et al., Circulating endothelial, cells, bone marrow-derived endothelial progenitor cells and proangiogenic hematopoietic cells in cancer: From biology to therapy, Critical Reviews In Oncology/Hematology, 69(2): 108-124 (2000).
Dudley, A.C. Tumor Endothelial Cells, Cold Spring Harb Perspect Med, 2(3): 1-18 (2012).
Elhallani, S. et al., Tumor and Endothelial Cell Hybrids Participate in Glioblastoma Vasculature, Biomed Res Int, 2014: 1-9 (2014).
Erdbruegger, U. et al., Circulating endothelial cells: A novel marker of endothelial damage, Clinica Chimica Acta, 373:17-26 (2006).
Goon, P.K.Y. et al., Circulating, Endothelial Cells, Endothelial Progenitor Cells, and Endothelial Microparticles in Cancer, Neoplasia, 8(2): 79-88 (2006).
International Search Report for PCT/SG2016/050027, 8 pages (dated Mar. 21, 2016).
Joo, C.H. et al., Differential amplifying RT-PCR: a novel RT-PCR method to differentiate mRNAfrom its DNA lacking intron, Journal of Virological Methods, 100: 71-81 (2002).
Kraan, J. et al., A new approach for rapid and reliable enumeration of circulating endothelial cells in patients, Journal of Thrombosis and Haemostasis, 10:931-939 (2012).
Kraan, J. et al., Clinical value of circulating endothelial cell detection in oncology, Drug Discovery Today, 17:710 (2012).
Kraan, J. et al., Endothelial CD276 (B7-H3) expression is increased in human malignancies and distinguishes between normal and tumour-derived circulating endothelial cells, British Journal of Cancer, 111:149-156 (2014).
Magbanua, M.J.M. et al., A Novel Strategy for Detection and Enumeration of Circulating Rare Cell Populations in Metastatic Cancer Patients Using Automated Microfluidic Filtration and Multiplex Immunoassay, PLOS One, 10(10): 1-18 (2015).
Malka, D. et al., Clinical value of circulating endothelial cell levels in metastatic colorectal cancer patients treated with first-line chemotherapy and bevacizumab, Annals of Oncology, 23: 919-927 (2012).
Mancuso, P. et al., A Subpopulation of Circulating Endothelial Cells Express CD109 and is Enriched in the Blood of Cancer Patients, PLoS One, 9(12): e114713 1-16 (2014).
Matsusaka, S. et al., Circulating endothelial cells predict for response to bevacizumab-based chemotherapy in metastatic colorectal cancer, Cancer Chemother Pharmacol, 68:763-768 (2011).
Mehran, R. et al., Tumor Endothelial Markers Define Novel Subsets of Cancer-Specific Circulating Endothelial Cells Associated with Antitumor Efficacy, Cancer Res, 74(1): 2731-2741 (2014).
Mesri, M. et al., Identification and Characterization of Angiogenesis Targets through Proteomic Profiling of Endothelial Cells in Human Cancer Tissues, Plos One, 8(11): e78885 (2013).
Ramcharan, S. K. et al., Angiogenin outperforms VEGF, EPCs and CECs in predicting Dukes and AJCC stage in colorectal cancer, European Journal of Clinical Investigation, 43(8):801-808 (2013).
Rigolin, G.M. et al., Neoplastic circulating endothelial cells in multiple myeloma with 12q14 deletion, Blood, 107:2531-2535 (2006).
Ronzoni, M. et al., Circulating endothelial cells and endothelial progenitors as predictive markers of clinical response to bevacizumab-based first-line treatment in advanced colorectal cancer patients, Annals of Oncology, 21:2382-2389 (2010).

(56) References Cited

OTHER PUBLICATIONS

Rowand, J. et al., Endothelial Cells in Peripheral Blood of Healthy Subjects and Patients with Metastatic Carcinomas, Cytometry Part A, 71A:105-113 (2007).
Simkens, L.H.J. et al., The predictive and prognostic value of circulating endothelial cells in advanced colorectal cancer patients receiving first-line chemotherapy and bevacizumab, Annals of Oncology, 21(12): 2447-2448 (2010).
Smirnov, D.A. et al., Global Gene Expression Profiling of Circulating Endothelial Cells in Patients with Metastatic Carcinomas, Cancer Res, 66(6): 2918-2921 (2006).
Strijbos, M.H. et al., Circulating endothelial cells in oncology: pitfalls and promises, British Journal of Cancer, 98: 1731-1735 (2008).
Written Opinion for PCT/SG2016/050027, 8 pages (dated Mar. 21, 2016).
Zanetta, L. et al., Expression of von Willebrand factor, an endothelial cell marker, is up-regulated by angiogenesis factors: A potential method for objective assessment of tumor angiogenesis, Int. J. Cancer, 85(2): 281-288 (2000).
First Examination Report in IN Application No. 201717025388 dated Feb. 9, 2022, 8 pages.
Cima, I. et al., Supplementary Materials for Tumor-derived circulating endothelial cell clusters in colorectal cancer, Sci. Transl. Med. (2016), <<https://stm.sciencemaci.orci/content/suppl/2016/06/27/8.345.345ra89.DC1>>. Retrieved on Nov. 10, 2020.
Office Action in Indonesian Application No. PID201704787 dated Aug. 27, 2021, 4 pages.
Office Action in Republic of Korea Patent Application No. 10-2017-7021401 dated Nov. 29, 2021, 5 pages.
"Supplementary Tables for 'Tumor-derived circulating endothelial cell clusters in colorectal cancer.'".
Second Office Action in EP Application No. 19 151 704.4 dated Feb. 6, 2023, 5 pages.

* cited by examiner

A

Inlet of Insert Device

Outlet of Insert Device

B b c

COLUMN-BASED DEVICE FOR RETRIEVAL OF RARE CELLS BASED ON SIZE, AND USES THEREOF

CROSS-REFERENCE TO RELATED APPLICATIONS

This patent application is a divisional of U.S. application Ser. No. 15/544,761, filed Jul. 19, 2017, which is a National Stage Entry of International Patent Application No. PCT/SG2016/050027, filed on Jan. 21, 2016, which claims the benefit of priority of Singapore provisional application Nos. 10201500471Q and 10201500472R, both filed on 21 Jan. 2015, the contents of each of which are hereby incorporated by reference in their entirety for all purposes herein.

SEQUENCE LISTING

The instant application contains a Sequence Listing, which has been submitted in ASCII format via EFS-WEB and is hereby incorporated by reference in its entirety. Said ASCII copy, created on Sep. 16, 2020, is named "Sequence Listing" and is 59.6 KB in size.

FIELD OF THE INVENTION

The present invention relates to a device and method for retrieving cells of interest, in particular rare cells. The present invention also relates to cells retrieved using the disclosed device and method, and use of the cells as biomarkers for the diagnosis and prognosis of cancer.

BACKGROUND OF THE INVENTION

Detection and retrieval of rare cells, such as diseased cells, are becoming increasingly important for accurate diagnosis of a disease state, such as cancer. Cancer is the second leading cause of death worldwide, accounting for 8.2 million deaths in 2012. Cancer mortality can be significantly reduced if detected and treated early. However, methods for reliable early detection of cancer mainly involve the use of endoscopies or radioactive scannings, which are costly and impose certain health risks to the patient.

Most devices currently available for isolation and detection of cells focus on capturing the cells only (for example using filter sieves), without retrieving the captured cells. This limits subsequent analysis of the captured cells to on-sieve characterization, for example using immunohistochemical staining. Using such devices, more complex analyses such as DNA mutation analysis or gene expression analysis on single cells of interest are not feasible. The devices and methods currently available for the isolation of rare cells suffer from the drawback of requiring additional steps to detach the cells stuck on the filter (using cumbersome techniques such as laser dissection microscopy). In fact, rare cells isolated using available microfiltration devices easily adhere to the filters or other components of the devices impacting negatively on the retrieval efficiency or even preventing any cell to be retrieved for downstream analyses.

Therefore, there is a need to provide a device and method for efficiently capturing and retrieving cells, particularly rare cells, that overcome, or at least ameliorate, one or more of the disadvantages described above. There is a need to optimize the efficiency of the retrieval of isolated rare cells using methods, materials and/or device configurations in such a way that the rare cells do not adhere to the components of the device and filters, so that the rare cells can be easily and efficiently retrieved for downstream procedures.

There is a need to provide less invasive screening test methods for the early detection of cancer.

SUMMARY OF THE INVENTION

In a first aspect, there is provided an apparatus for capturing and retrieving a cell from a sample, comprising at least one column, the column comprising:
  (i) an inner wall defining an inner chamber, the inner chamber having an inlet opening at a first end of the column for receiving the sample, and an outlet opening at a second end of the column;
  (ii) a perforated plug disposed within the inner chamber adjacent to the second end of the column;
  (iii) a sleeve insert having an opening at a first end and an opening at a second end, the sleeve insert comprising a channel tapered at the second end and disposed within the inner chamber with its second end adjacent to the perforated plug; and
  (iv) a filtering means housed within the sleeve insert, the filtering means comprising a sieve sandwiched between two sealing means.

In a second aspect, there is provided a method of capturing and retrieving a cell from a sample, comprising the steps of:
  (a) introducing the sample to the inlet opening of the apparatus as described herein to allow the sample to flow through the sleeve insert and filtering means of the apparatus; and
  (b) collecting the residue retained on the surface of the sieve in the filtering means of the apparatus.

In a third aspect, there is provided an isolated cell population having the following characteristics:
  (i) being endothelial cells derived from a tumor and isolated from blood;
  (ii) each cell having at least two clearly distinct nuclei;
  (iii) each cell having a major axis of greater than about 10 µm;
  (iv) expression of endothelial cell genes or proteins;
  (v) non-expression of leukocyte-specific genes or proteins; and
  (vi) non-expression of megakaryocyte or platelets-specific genes or proteins.

In a fourth aspect, there is provided a method for detecting the isolated cell population as described herein in a sample of a subject, the method comprising:
  (a) capturing and retrieving the cells from the sample using the apparatus as described herein or the method as described herein.

In one embodiment, the method of the fourth aspect further comprises the steps of:
  (b) contacting the cells from step (a) with at least one antibody coupled to a detectable label to allow binding of the antibody to one or more target biomarkers expressed on the cells;
  (c) removing unbound antibody from the sample; and
  (d) detecting and analyzing the detectable label bound to the antibody to detect the isolated population of cells.

In another embodiment, the method of the fourth aspect further comprises the steps of:
  (b) lysing the cells from step (a);
  (c) contacting the lysed cell sample from step (b) with a reverse primer from a first primer pair, the reverse primer from the first primer pair being directed to a target RNA region, and a reverse transcriptase to effect reverse transcription of the RNA into cDNA;
(d) subsequently contacting the sample from step (c) with:
(i) a forward primer from the first primer pair, the forward primer from the first primer pair being directed to a target cDNA region,
(ii) a reverse primer and a forward primer from a second primer pair, the reverse primer and forward primer from the second primer pair being directed to a target DNA region, and
(iii) a DNA polymerase
to simultaneously amplify the target cDNA region and the target DNA region in a pre-amplification step; and
(e) analyzing the amplified target cDNA region and/or the amplified target DNA region.

In one embodiment, the method of the fourth aspect further comprises: subjecting the sample from step (d) to a semi-nested PCR using the reverse primer in step (c) or the forward primer in step (d)(i), and a nested primer that binds within the amplified target cDNA region.

In yet another embodiment, the method of the fourth aspect further comprises: subjecting the sample from step (d) to a nested PCR using a nested primer pair that binds within the amplified target DNA region.

In a fifth aspect, there is provided a method for detecting the isolated cell population of the third aspect in a sample of a subject, the method comprising:
(a) contacting cells from the sample with at least one antibody coupled to a detectable label to allow binding of the antibody to one or more target biomarkers expressed on the cells;
(b) removing unbound antibody from the sample; and
(c) detecting and analyzing the detectable label bound to the antibody to detect the isolated population of cells.

In a sixth aspect, there is provided a method for detecting the isolated cell population of the third aspect in a sample of a subject, the method comprising:
(a) lysing the cells present in the sample;
(b) contacting the lysed cell sample from step (a) with a reverse primer from a first primer pair, the reverse primer from the first primer pair being directed to a target RNA region, and a reverse transcriptase to effect reverse transcription of the RNA into cDNA;
(c) subsequently contacting the sample from step (b) with:
(i) a forward primer from the first primer pair, the forward primer from the first primer pair being directed to a target cDNA region,
(ii) a reverse primer and a forward primer from a second primer pair, the reverse primer and forward primer from the second primer pair being directed to a target DNA region, and
(iii) a DNA polymerase
to simultaneously amplify the target cDNA region and the target DNA region in a pre-amplification step; and
(d) analyzing the amplified target cDNA region and/or the amplified target DNA region.

In one embodiment, the method of the sixth aspect further comprises: subjecting the sample from step (c) to a semi-nested PCR using the reverse primer in step (b) or the forward primer in step (c)(i), and a nested primer that binds within the amplified target cDNA region.

In yet another embodiment, the method of the sixth aspect further comprises: subjecting the sample from step (c) to a nested PCR using a nested primer pair that binds within the amplified target DNA region.

In a seventh aspect, there is provided a method of diagnosing a cancer in a subject, comprising analyzing a sample from the subject for presence of the isolated population of cells as described herein, wherein presence of the isolated population of cells indicates that the subject has cancer.

In an eighth aspect, there is provided a method for monitoring and/or predicting the response to treatment of a cancer patient, the method comprising analyzing a sample obtained from the patient after treatment for determining the number of the isolated population of cells as described herein, wherein a reduction in the number of the isolated population of cells compared to the number of the isolated population of cells in a baseline sample obtained from the patient prior to treatment indicates that the patient is responding positively to the treatment.

In a ninth aspect, there is provided a method for predicting the response to treatment of a cancer patient, the method comprising analyzing a sample obtained from the cancer patient before treatment for determining the number of the isolated population of cells as described herein, wherein an equal or higher number of the isolated population of cells compared to the number of the isolated population of cells in a sample obtained before treatment from a patient or a group of patients that have responded positively to the treatment indicates that the cancer patient will respond positively to the treatment, and wherein a lower number of the isolated population of cells compared to the number of the isolated population of cells in a sample obtained before treatment from a patient or a group of patients that have responded positively to the treatment indicates that the cancer patient will respond negatively to the treatment.

In a tenth aspect, there is provided a method for analyzing blood vessel characteristics of a tumor in a subject, the method comprising analyzing a sample from the subject for determining the number of the isolated population of cells as described herein, wherein an increased number of the isolated population of cells compared to a baseline sample indicates that the tumor has larger blood vessels compared to the baseline sample, and wherein a reduced number of the isolated population of cells compared to a baseline sample indicates that the tumor has smaller blood vessels compared to the baseline sample.

In an eleventh aspect, there is provided a kit for use in the method of the second, the fourth, the seventh, the eighth, the ninth or the tenth aspects, the kit comprising:
(a) the apparatus as described herein.

In one embodiment, the kit of the eleventh aspect further comprises one or more of the following:
(b) one or more cell lysis buffers;
(c) a primer selected from the group consisting of:
  i. the reverse primer of step (c) of the method of the fourth aspect,
  ii. the forward primer of step (d)(i) of the method of the fourth aspect,
  iii. the primer pair of step (d)(ii) of the method of the fourth aspect, and
  iv. the nested primer and nested primer pair of the method of the fourth aspect;
(d) one or more reagents, selected from the group consisting of:
  i. a reverse transcriptase and one or more suitable reaction buffers for the reverse transcription in step (c) of the method of the fourth aspect,
  ii. a DNA polymerase and one or more suitable reaction buffers for the amplification in step (d) of the method of the fourth aspect or the semi-nested or nested PCR of the method of the fourth aspect, and iii. one or more labelled or unlabelled deoxyribonucleotides selected from the group consisting of dATP, dCTP, dGTP, and dTTP or dUTP; and
(e) an antibody capable of specific binding to a protein selected from the group consisting of PAI-1, Vimentin, FOXC1, keratin-8, keratin-18, keratin-19, Ep-CAM, CD45, VWF, PECAM-1, CD146, CD41, CD34, PSMA, CD105, CD309, CD144, CD202B and Angiopoietin 2, wherein the antibody is coupled to a detectable label; and optionally means for detecting the detectable label.

In a twelfth aspect, there is provided a kit for use in the method of the fifth, the sixth, the seventh, the eighth, the ninth or the tenth aspects, the kit comprising one or more of the following:
(a) one or more cell lysis buffers;
(b) a primer selected from the group consisting of:
 i. the reverse primer of step (b) of the method of the fifth aspect,
 ii. the forward primer of step (c)(i) of the method of the fifth aspect,
 iii. the primer pair of step (c)(ii) of the method of the fifth aspect, and
 iv. the nested primer and nested primer pair of the method of the fifth aspect;
(c) one or more reagents, selected from the group consisting of:
 i. a reverse transcriptase and one or more suitable reaction buffers for the reverse transcription in step (b) of the method of the fifth aspect,
 ii. a DNA polymerase and one or more suitable reaction buffers for the amplification in step (c) of the method of the fifth aspect or the semi-nested or nested PCR of the method of the fifth aspect, and
 iii. one or more labelled or unlabelled deoxyribonucleotides selected from the group consisting of dATP, dCTP, dGTP, and dTTP or dUTP; and
(d) an antibody capable of specific binding to a protein selected from the group consisting of PAI-1, Vimentin, FOXC1, keratin-8, keratin-18, keratin-19, Ep-CAM, CD45, VWF, PECAM-1, CD146, CD41, CD34, PSMA, CD105, CD309, CD144, CD202B and Angiopoietin 2, wherein the antibody is coupled to a detectable label as described herein; and optionally means for detecting the detectable label.

In another embodiment, the kit of the eleventh or the twelfth aspect further comprises instructions for performing the methods as described herein.

BRIEF DESCRIPTION OF THE DRAWINGS

The invention will be better understood with reference to the detailed description when considered in conjunction with the non-limiting examples and the accompanying drawings, in which:

FIG. 14, panel (A) is a flow chart of the lineage inference workflow. FIG. 14, panel (B) shows selected genes with highest specificity index for representative lineages are verified for specificity using BioGPS (Wu et al.). FIG. 14, panel (C) shows gene expression level of markers commonly used in CTC research to denote epithelial cells. Note KRT18 expression in the endothelial lineages and EPCAM expression in hematopoietic cells.

DETAILED DESCRIPTION OF THE PRESENT INVENTION

Figure 1:
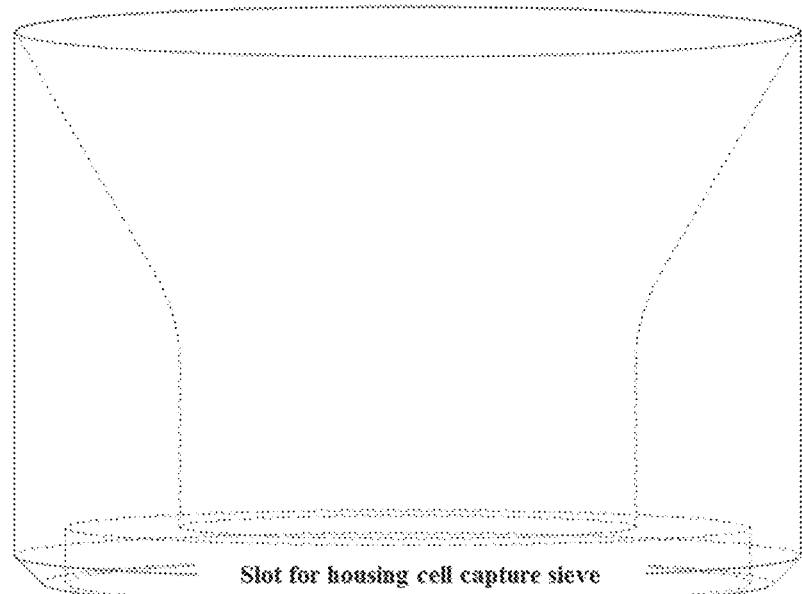
FIG. 1 shows an example of the device described herein for the capture and retrieval of rare cells. (A) shows the insert sleeve, which has an inlet at the upper end and an outlet at the lower end. The insert sleeve functions as a housing for the cell capturing sieve, securing the cell capture sieve near the outlet of a column. The sample flows in from the inlet of the insert sleeve, and flows out through the outlet of the insert sleeve. (B) shows that the channel through which the sample flows tapers at the lower end of the insert sleeve. (C) illustrates the assembly of the insert sleeve (or "sleeve insert" used interchangeably herein) and the cell capture sieve in a column of the device. The cell capture sieve (sandwiched between two O-rings acting as the sealing means) is first placed into the slot near the outlet of the insert sleeve, and then the entire assembly is inserted into the column by using an insert tool in the form of a rod (not shown). (D) shows two cell capturing and retrieval devices being connected to a peristaltic pump in one exemplary configuration when using the devices in a method described herein. A blood sample was filtered through the device. (E) shows depletions of contaminating white blood cells (WBCs) and red blood cells (RBCs) using cell capturing sieves with various pore diameters. One ml of whole blood was filtered through the device. Contaminating WBCs and RBCs were retrieved and counted (black bars), or retrieved and counted after inverting the flow of the peristaltic pump ("backflushing") for a short time to dislodge cells that were stuck on the sieve (white bars). Fold depletion was calculated as follows: Fold Depletion of WBCs or RBCs=(WBCs or RBCs in Whole Blood)/(WBCs or RBCs in Microfiltrate). The bars in (E) represents the mean value obtained from tests with three different devices for each condition tested. Error bar represents the standard deviation. (F) shows the size distribution of SW620 (light grey line), (n=50). Median size of WBCs and circulating tumor cells (CTCs) isolated from colorectal, prostate and breast cancer patients respectively reported from Coumans, F et al., 2013. (G) shows retrieval efficacy of the device using whole blood spiked with the various cell lines. 20 to 50 cells/ml were labeled and spiked in 1 ml or 3 ml of whole blood. Each blood sample was passed through the device, and the target cells were retrieved, placed in a 96-well plate and counted. Retrieval efficacy was calculated as follows: % Retrieval Efficiency= (Retrieved cells)×100/(Spiked Cells). Each dot corresponds to an independent experiment.
Figure 1:
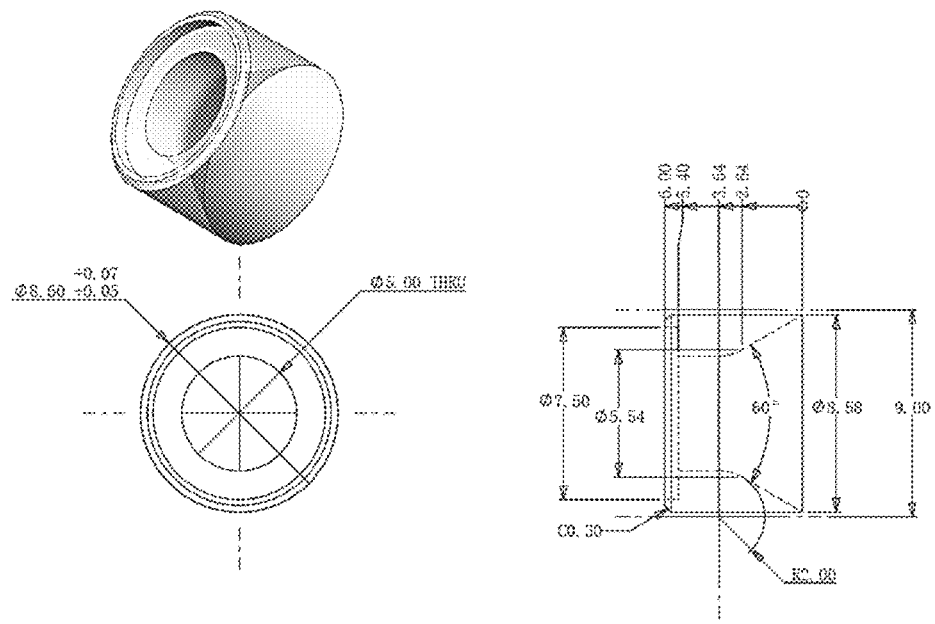
Figure 1:
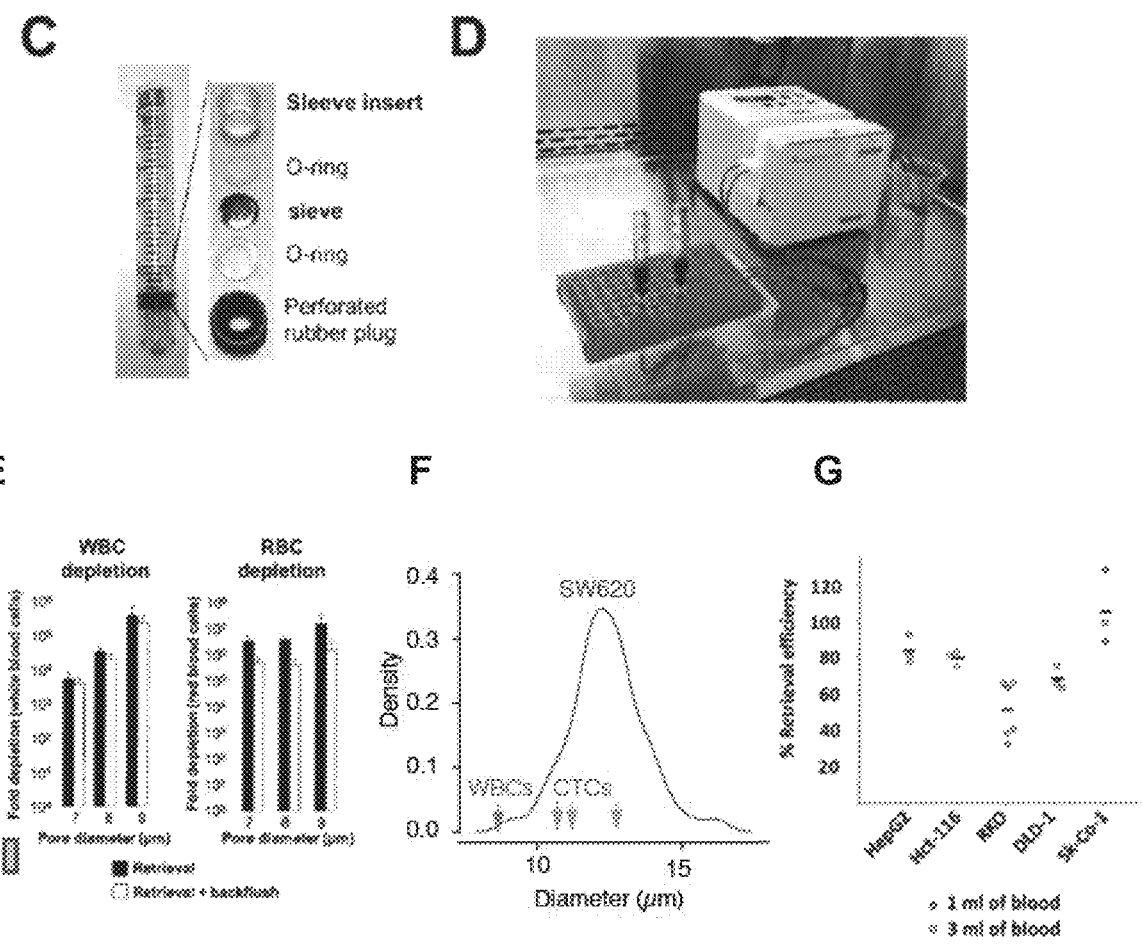

The present disclosure provides an apparatus for capturing and retrieving cells, particularly rare cells, which allows easy downstream manipulation and analysis of the captured cells. Thus, in a first aspect, there is provided an apparatus for capturing and retrieving a cell from a sample, comprising at least one column, the column comprising:
 (i) an inner wall defining an inner chamber, the inner chamber having an inlet opening at a first end of the column for receiving the sample, and an outlet opening at a second end of the column;
 (ii) a perforated plug disposed within the inner chamber adjacent to the second end of the column;
 (iii) a sleeve insert having an opening at a first end and an opening at a second end, the sleeve insert comprising a channel tapered at the second end and disposed within the inner chamber with its second end adjacent to the perforated plug; and
 (iv) a filtering means housed within the sleeve insert, the filtering means comprising a sieve sandwiched between two sealing means.

The terms "apparatus" and "device" are used interchangeably in the present disclosure.

The term "capture" or "capturing" used herein means catching or trapping the cell(s) of interest. The term "retrieve", "retrieval" or "retrieving" used herein means recovering or collecting the captured cell(s). For example, the retrieval may involve recovering or collecting the cells from the capture sieve by detaching the cells using a pipette.

The term "isolate", "isolating" or "isolated" used herein means separating the cell(s) of interest from the sample, such that the separated cell(s) is substantially or essentially free from other components present in the sample.

The term "microfiltration" used herein refers to a physical filtration process wherein a sample is passed through a special pore-sized filtering means to isolate suspended particles (such as cells, microorganisms, etc.) from the sample. The typical pore diameters used for microfiltration are in microns (i.e. micro meter or μm).

The term "sample" used herein refers to a biological sample, or a sample that comprises at least some biological materials such as cells. The biological samples of this disclosure may be any sample suspected to contain TECCs, including solid tissue samples, such as bone marrow, and liquid samples, such as whole blood, blood serum, blood plasma, cerebrospinal fluid, central spinal fluid, lymph fluid, cystic fluid, sputum, stool, pleural effusion, mucus, pleural fluid, ascitic fluid, amniotic fluid, peritoneal fluid, saliva, bronchial washes and urine. In some embodiments, the biological sample is a blood sample. As will be appreciated by those skilled in the art, a biological sample can include any fraction or component of blood, without limitation, T-cells, monocytes, neutrophiles, erythrocytes, platelets and microvesicles such as exosomes and exosome-like vesicles.

The biological samples of this disclosure may be obtained from any organism, including mammals such as humans, primates (e.g., monkeys, chimpanzees, orangutans, and gorillas), cats, dogs, rabbits, farm animals (e.g., cows, horses, goats, sheep, pigs), and rodents (e.g., mice, rats, hamsters, and guinea pigs).

It is noted that, as used herein, the terms "organism," "individual," "subject," or "patient" are used as synonyms and interchangeably.

The organism may be a healthy organism or suffer from a disease condition. Disease conditions may include any disease. In some embodiments, the disease is cancer, diabetes, metabolic syndrome, or an autoimmune disorder. In some embodiments, the healthy or diseased organism is a human organism. In some embodiments, the healthy or diseased organism is an animal model for a disease condition, such as cancer. A person of ordinary skill understands that animal models for various disease conditions are well known in the art.

A diseased organism may be untreated or may have received treatment, such as chemotherapy, radiotherapy and surgery. The treatment may predate the sample collection or be ongoing at the time of sample collection.

The samples of this disclosure may each contain a plurality of cell populations and cell subpopulations that can be distinguishable by methods well known in the art (e.g., FACS, immunohistochemistry). For example, a blood sample may contain populations of non-nucleated cells, such as erythrocytes or platelets, and populations of nucleated cells such as white blood cells (WBCs), circulating tumor cells (CTC). WBCs may contain cellular subpopulations such as neutrophils, lymphocytes, monocytes, eosinophils, basophils and the like. The samples of this disclosure may be non-enriched samples, i.e., they are not enriched for any specific population or subpopulation of nucleated or non-nucleated cells. For example, non-enriched blood samples are not enriched for TECCs, WBCs, B-cells, T-cells, NK-cells, monocytes, or the like.

The term "rare cell," as used herein, refers to a cell that has an abundance of less than 1:1,000 in a cell population, e.g., an abundance of less than 1:5,000, 1:10,000, 1:30,000, 1:50,000, 1:100,000, 1:300,000, 1:500,000, 1:1,000,000, 1:5,000,000, 1:10,000,000, 1:30,000,000, 1:50,000,000, 1:100,000,000, 1:300,000,000, 1:500,000,000 or 1:1,000,000,000. In some embodiments, the rare cell has an abundance of 1:1,000,000 to 1:10,000,000,000 in the cell population. In some examples, the cell population is a nucleated or non-nucleated cell population. In some embodiments, the rare cell is a TECC.

The term "adjacent" used herein means near, next to, proximate to, or adjoining. For example, the sleeve insert of the device described herein may be next to or proximate to the perforated plug in the column of the device. A gap may or may not be present between the sleeve insert and the perforate plug, and the sleeve insert may or may not be attached to the perforated plug.

In one embodiment, the apparatus comprises one column. In some other embodiments, the apparatus comprises two or more columns. The two or more columns can be arranged in any configurations, including but not limited to in series or in parallel, or any combinations thereof. The column may be any completely or partially hollow structure of any shape, such as cylindrical, conical or cubical. In one example, the column is cylindrical. In one example, the column comprises a syringe.

The first end of the column can be adapted for connection to an upstream device or apparatus, while the second end of the column can be adapted for connection to a downstream device or apparatus. In one embodiment, the first end of the column comprises an opening which allows easy retrieval of the captured cells. In one example, simply pipetting can be used to retrieve the cells from the opening. Advantageously, in some examples, back-flushing of the captured cells is not necessary for retrieval. Advantages of omitting the back-flushing step include but are not limited to, reduction in the number of steps required in the capturing and retrieving procedure and reduced contamination of the captured and retrieved cells by impurities. In one embodiment, the second end of the column is adapted for connection to one or more pumps for controlling flow-rate of the sample passing through the column. Any pumps suitable for this purpose may be used, such as peristaltic pumps.

The flow-rate at which the sample is passed through the column may be determined by factors including but not limited to: the types of samples used, the amount of samples available, the size of the target cells to be captured and retrieved, the number of cells to be captured and retrieved, the percentage of cells in the sample to be captured and retrieved, etc. In some examples, the flow-rate can be any one of the following: at least about 0.01 mL/min, at least about 0.02 mL/min, at least about 0.03 mL/min, at least about 0.04 mL/min, at least about 0.05 mL/min, at least about 0.06 mL/min, at least about 0.07 mL/min, at least about 0.08 mL/min, at least about 0.09 mL/min, at least about 0.10 mL/min, at least about 0.15 mL/min, at least about 0.20 mL/min, at least about 0.25 mL/min, at least about 0.30 mL/min, at least about 0.35 mL/min, at least about 0.40 mL/min, at least about 0.45 mL/min, at least about 0.50 mL/min, at least about 0.60 mL/min, at least about 0.70 mL/min, at least about 0.80 mL/min, at least about 0.90 mL/min, at least about 1.0 mL/min, at least about 1.1 mL/min, at least about 1.2 mL/min, at least about 1.3 mL/min, at least about 1.4 mL/min, at least about 1.5 mL/min, at least about 1.6 mL/min, at least about 1.7 mL/min, at least about 1.8 mL/min, at least about 1.9 mL/min, at least about 2.0 mL/min, at least about 3.0 mL/min, at least about 4.0 mL/min, at least about 5.0 mL/min, at least about 6.0 mL/min, at least about 7.0 mL/min, at least about 8.0 mL/min, at least about 9.0 mL/min, at least about 10.0 mL/min, at least about 15.0 mL/min, at least about 20.0 mL/min, at least about 25.0 mL/min, at least about 30.0 mL/min, at least about 35.0 mL/min, at least about 40.0 mL/min, at least about 45.0 mL/min, or at least about 50.0 mL/min. In one example, the flow rate is between 0.05 mL/min and 50.0 mL/min.

The perforated plug serves as a supporting means for the insert sleeve, while at the same time providing a channel for the filtrate to pass through. The term "perforated" or "perforation" refers to a hole or a number of holes through the plug. The plug can be perforated by a puncturing means, and the perforated plug can be made of any materials. In one example, the perforated plug is a perforated rubber plug.

The sleeve insert (or insert sleeve used interchangeably herein) may function as a housing for the filtering means, while at the same time function as a sealing means to prevent the unfiltered sample from flowing through channels other than through the filtering means. The sleeve insert comprises a channel tapered at the second end to channel the sample to the center of the filtering means. In one example, the filtering means comprises a sieve.

The cells captured using the device as described herein can be easily retrieved without requiring additional steps such as laser dissection and optical tweezers to detach the captured cells from the cell capture sieve. Thus the one of more of the surfaces of the device that are in direct contact with the sample comprises non cell-adhesive material.

In one embodiment, the sieve comprises non cell-adhesive material. In another embodiment, the non cell-adhesive material is selected from the group consisting of silicon, silicon dioxide, silicon nitride, epoxy-based negative photoresist and ceramic. An example of the epoxy-based negative photoresist is SU-8.

The sieve of the device as described herein comprises a plurality of pores through which cells (or other components of the sample) that are not of interest and therefore not to be captured, may be allowed to pass. The size or diameter of the pores may be determined by factors including but not limited to: the size of the cells to be captured and retrieved, the size of the cells to be eliminated, the amount of sample used, the viscosity of the sample used, etc. The plurality of pores in the same sieve may be of the same diameter, or maybe of various diameters. In some examples, the pore diameter can be any one of the following: at least about 5 µm, at least about 6 µm, at least about 7 µm, at least about 8 µm, at least about 9 µm, at least about 10 µm, at least about 11 µm, at least about 12 µm, at least about 13 µm, at least about 14 µm, at least about 15 µm, at least about 16 µm, at least about 17 µm, at least about 18 µm, at least about 19 µm, at least about 20 µm, at least about 25 µm, at least about 30 µm, at least about 35 µm, at least about 40 µm, at least about 45 µm, at least about 50 µm, at least about 60 µm, at least about 70 µm, at least about 80 µm, at least about 90 µm, at least about 100 µm or at least about 200 µm. For example, to capture and retrieve tumor-derived endothelial cell clusters (TECCs), the pore diameters can be about 6 µm, about 7 µm, about 8 µm, about 9 µm or about 10 µm. In one example, the pore diameter is 9 µm. In another example, the pore diameter is 10 µm.

In a second aspect, there is provided a method of capturing and retrieving a cell from a sample, comprising the steps of:
  (a) introducing the sample to the inlet opening of the apparatus as described herein to allow the sample to flow through the sleeve insert and filtering means of the apparatus; and
  (b) collecting the residue retained on the surface of the sieve in the filtering means of the apparatus.

The method may be applied to a biological sample as described herein, which may comprise heterogenous cell types from a subject. The biological sample may be selected from the group consisting of tissues, cells (e.g. a stem cell, a suspected cancer cell), body fluids and isolates thereof etc., isolated from a subject.

In one embodiment, the sample comprises a biological fluid. In some embodiments, the biological fluid comprises any one of the following: whole blood, blood serum, blood plasma, cerebrospinal fluid, lymph fluid, cystic fluid, sputum, stool, pleural effusion mucus, ascitic fluid and urine.

The sample may comprise any number of cells. In one embodiment, the sample comprises a single cell. In another embodiment, the sample comprises a plurality of cells. In a further embodiment, the sample comprises a plurality of cells, wherein two or more of the plurality of cells form a cell cluster or a multinucleated cell. In one embodiment, the multinucleated cell comprises a single-TECC. In one embodiment, the single cell is selected from the group consisting of a suspected cancer cell, a suspected tumor-derived cell, a suspected cell derived from an embryo or a foetus, and a cell from a pathogenic organism.

In another embodiment, at least some of the plurality of cells are selected from the group consisting of: suspected cancer cells, suspected tumor-derived cells, suspected cells derived from an embryo or a foetus, and cells from a pathogenic organism.

The cell captured and retrieved using the method described herein may comprise various numbers of clearly distinct nuclei. For example, the number of clearly distinct nuclei can be any one of the following: from about 2 to about 100, from about 5 to about 90, from about 10 to about 80, from about 20 to about 70, from about 30 to about 60, from about 40 to about 50 distinct nuclei, or at least 2, at least 3, at least 4, at least 5, at least 7, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or at least 100 distinct nuclei.

In one embodiment, the sample is a blood sample, and the cell captured and retrieved therefrom comprises at least two clearly distinct nuclei.

The length of the major axis of the cell captured and retrieved can be any one of the following: at least about 5 µm, at least about 6 µm, at least about 7 µm, at least about 8 µm, at least about 9 at least about 10 µm, at least about 11 µm, at least about 12 µm, at least about 13 µm, at least about 14 µm, at least about 15 µm, at least about 16 µm, at least about 17 µm, at least about 18 µm, at least about 19 µm, at least about 20 µm, at least about 25 µm, at least about 30 µm, at least about 35 µm, at least about 40 µm, at least about 45 µm, at least about 50 µm, at least about 60 µm, at least about 70 µm, at least about 80 µm, at least about 90 µm, at least about 100 µm or at least 200 µm.

The cell captured and retrieved using the method as described herein may be characterized by the expression or non-expression of a number of genes and/or proteins. In one embodiment, the cell captured and retrieved expresses one or more of the following genes: PECAM1, VWF and CDH5. In one example of this embodiment, the cell expresses any of the following combinations of genes: PECAM1 and VWF; PECAM1 and CDH5; VWF and CDH5; or PECAM1, VWF and CDH5. In another embodiment, the cell captured and retrieved does not express one or more of the following genes: PTPRC, ITGA2B and GP1BA. In one example of this embodiment, the cell does not express any of the following combinations of genes: PTPRC and ITGA2B; PTPRC and GP1BA; ITGA2B and GP1BA; or PTPRC, ITGA2B and GP1BA.

A person skilled in the art will understand that the gene PECAM1 encodes for the protein CD31, the gene VWF encodes for the protein VWF, the gene CDH5 encodes for the protein CD144, the gene PTPRC encodes for the protein CD45, the gene ITGA2B encodes for the protein CD41 and the gene GP1BA encodes for the protein CD42B. Thus, in one embodiment, the cell captured and retrieved expresses one or more of the following proteins: CD31, VWF and CD144. In one example of this embodiment, the cell expresses any of the following combinations of proteins: CD31 and VWF; CD31 and CD144; VWF and CD144; or CD31, VWF and CD144. In another embodiment, the cell captured and retrieved does not express one or more of the following gene proteins: CD45, CD41 and CD42B. In one example of this embodiment, the cell does not express any of the following combinations of proteins: CD45 and CD41; CD45 and CD42B; CD41 and CD42B; or CD45, CD41 and CD42B.

The method of cell capturing and retrieving as described herein may allow any percentage of the target cells in the sample to be captured. Advantageously, a high percentage of the target cells in the sample may be captured and/or retrieved. The percentage of cells present in the sample being captured and retrieved using the method as described herein may be any one of the following: at least about 10, at least about 20%, at least about 30%, at least about 40%, at least about 50%, at least about 55%, at least about 60%, at least about 65%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 95.5%, at least about 96%, at least about 96.5%, at least about 97%, at least about 97.5%, at least about 98%, at least about 98.5%, at least about 99%, at least about 99.5% or 100%.

The collection of the residue retained on the surface of the sieve in the filtering means of the apparatus may be carried out using various physical and/or chemical methods. In one embodiment, collecting the residue retained on the surface of the sieve in the filtering means of the apparatus comprises standard pipetting.

Using the cell capturing and retrieving device and method of the present invention allowed the inventors to identify an isolated population of cells. Thus, in a third aspect, there is provided an isolated cell population having the following characteristics:
  (i) being endothelial cells derived from a tumor and isolated from blood;
  (ii) each cell having at least two clearly distinct nuclei;
  (iii) each cell having a major axis of greater than about 10 μm;
  (iv) expression of endothelial cell genes or proteins;
  (v) non-expression of leukocyte-specific genes or proteins; and
  (vi) non-expression of megakaryocyte or platelets-specific genes or proteins.

The term "endothelial cells" refers to the thin layer of simple squamous cells that line the inner surface of blood vessels and lymphatic vessels. Endothelial cells in direct contact with blood are called vascular endothelial cells, whereas those in direct contact with lymph are known as lymphatic endothelial cells.

The term "leukocyte" refers to white blood cells (WBCs), which are the cells of the immune system that are involved in protecting the body against both infectious disease and foreign invaders. The term "megakaryocyte" refers to a large bone marrow cell with a lobulated nucleus responsible for the production of blood thrombocytes (platelets), which are necessary for normal blood clotting. The term "platelets" refers to a component of blood whose function (along with the coagulation factors) is to stop bleeding by clumping and clotting blood vessel injuries. Platelets have no cell nucleus, they are fragments of cytoplasm that are derived from the megakaryocytes of the bone marrow, and then enter the circulation.

In one embodiment, the endothelial cell genes expressed by the isolated cell population described herein include but are not limited to PECAM1, VWF and CDH5. In one embodiment, the endothelial cell proteins expressed by the isolated cell population described herein include but are not limited to CD31, VWF and CD144.

In one embodiment, the leukocyte-specific, megakaryocytic or platelet-specific genes not expressed by the isolated cell population described herein include but are not limited to PTPRC, ITGA2B and GP1BA. In one embodiment, the leukocyte-specific, megakaryocytic or platelet-specific proteins not expressed by the isolated cell population described herein include but are not limited to CD45, CD41 and CD42B.

In some examples, the following combination of gene expressions can be used to define an endothelial cell: PECAM1 positive and PTPRC negative, VWF positive and ITGA2B negative, VWF positive and GP1BA negative, CDH5 positive and PTPRC negative. In some other examples, the following combination of protein expressions can be used to define an endothelial cell: CD31 positive and CD45 negative, VWF positive and CD41 negative, VWF positive and CD42B negative, CD144 positive and CD45 negative.

The cell capturing and retrieving device and method as described herein can be used to capture and retrieve the isolated cell population as described herein. Thus, in a fourth aspect, there is provided a method for detecting the isolated cell population as described herein in a sample of a subject, the method comprising:
  (a) capturing and retrieving the cells from the sample using the apparatus as described herein or the method as described herein.

The isolated cell population captured using the device and method as described herein can be subjected to downstream manipulation and/or analysis, for example, to detect the expression of certain genes and/or proteins. Thus, in one embodiment, the method of the fourth aspect further comprises:
  (b) contacting the cells from step (a) with at least one antibody coupled to a detectable label to allow binding of the antibody to one or more target biomarkers expressed on the cells;
  (c) removing unbound antibody from the sample; and
  (d) detecting and analyzing the detectable label bound to the antibody to detect the isolated population of cells.

The isolated cell population as described herein can also be obtained using other cell isolation methods. Thus, in a fifth aspect, there is provided a method for detecting the isolated cell population of the third aspect in a sample of a subject, the method comprising:
  (a) contacting cells from the sample with at least one antibody coupled to a detectable label to allow binding of the antibody to one or more target biomarkers expressed on the cells;
  (b) removing unbound antibody from the sample; and
  (c) detecting and analyzing the detectable label bound to the antibody to detect the isolated population of cells.

In one embodiment, prior to step (a) of the method of the fifth aspect, the cells are isolated from the sample using the method of the second aspect or any cell capture and retrieval methods known in the art.

The term "antibody" means an immunoglobulin molecule able to bind to a specific epitope on an antigen. Antibodies can be comprised of a polyclonal mixture, or may be monoclonal in nature. Further, antibodies can be entire immunoglobulins derived from natural sources, or from recombinant sources. The antibodies used in the methods described herein may exist in a variety of forms, including for example as a whole antibody, or as an antibody fragment, or other immunologically active fragment thereof, such as complementarity determining regions. Similarly, the antibody may exist as an antibody fragment having functional antigen-binding domains, that is, heavy and light chain variable domains. Also, the antibody fragment may exist in a form selected from the group consisting of, but not limited to: Fv, Fab, F(ab)2, scFv (single chain Fv), dAb (single domain antibody), bi-specific antibodies, diabodies and triabodies. Exemplary antibodies are as described in Example 3.

In one embodiment, the antibodies used in the methods described herein are capable of specific binding to a biomarker. The term "biomarker" refers to a biological molecule, or a fragment of a biological molecule, the change and/or the detection of which can be correlated with a particular physical condition or state of a TECC. The terms "marker" and "biomarker" are used interchangeably throughout the disclosure. Such biomarkers include, but are not limited to, biological molecules comprising nucleotides, nucleic acids, nucleosides, amino acids, sugars, fatty acids, steroids, metabolites, peptides, polypeptides, proteins, carbohydrates, lipids, hormones, antibodies, regions of interest that serve as surrogates for biological macromolecules and combinations thereof (e.g., glycoproteins, ribonucleoproteins, lipoproteins). The term also encompasses portions or fragments of a biological molecule, for example, peptide fragment of a protein or polypeptide. In one embodiment, the biomarkers are cancer biomarkers. In one embodiment, the antibody is capable of specific binding to any one of the following target biomarkers: PAI-1, Vimentin, FOXC1, keratin-8, keratin-18, keratin-19, Ep-CAM, CD45, VWF, PECAM-1, CD146, CD41, CD34, PSMA, CD105, CD309, CD144, CD202B and Angiopoietin 2.

In one embodiment, the antibody is coupled to a detectable label by methods known in the art, such as direct antibody conjugation and indirect antibody conjugation. The term "direct antibody conjugation" refers to the conjugation of the primary antibody to a detectable label. The term "indirect antibody conjugation" refers to a two-step method wherein the primary antibody is not conjugated to a detectable label. A secondary antibody directed against the primary antibody is used, wherein the secondary antibody is conjugated to a detectable label. The detectable label can be any one of the following: a fluorescent group, a radioisotope, a stable isotope, an enzymatic group, a chemiluminescent group or a biotinyl group. Exemplary fluorescence-labeled antibodies are described in Example 3.

A number of other methods are known in the art for detecting binding of an antibody to its antigen in an immunoassay and are within the scope of the present disclosure.

Other methods such as scrmPCR can also be used for detecting and analysing the isolated cell population as described herein. Thus, one embodiment of the method of the fourth aspect further comprises:
(b) lysing the cells from step (a);
(c) contacting the lysed cell sample from step (b) with a reverse primer from a first primer pair, the reverse primer from the first primer pair being directed to a target RNA region, and a reverse transcriptase to effect reverse transcription of the RNA into cDNA;
(d) subsequently contacting the sample from step (c) with:
(i) a forward primer from the first primer pair, the forward primer from the first primer pair being directed to a target cDNA region,
(ii) a reverse primer and a forward primer from a second primer pair, the reverse primer and forward primer from the second primer pair being directed to a target DNA region, and
(iii) a DNA polymerase
to simultaneously amplify the target cDNA region and the target DNA region in a pre-amplification step; and
(e) analyzing the amplified target cDNA region and/or the amplified target DNA region.

In a sixth aspect, there is provided a method for detecting the isolated cell population of the third aspect in a sample of a subject, the method comprising:
(a) lysing the cells present in the sample;
(b) contacting the lysed cell sample from step (a) with a reverse primer from a first primer pair, the reverse primer from the first primer pair being directed to a target RNA region, and a reverse transcriptase to effect reverse transcription of the RNA into cDNA;
(c) subsequently contacting the sample from step (b) with:
(i) a forward primer from the first primer pair, the forward primer from the first primer pair being directed to a target cDNA region,
(ii) a reverse primer and a forward primer from a second primer pair, the reverse primer and forward primer from the second primer pair being directed to a target DNA region, and
(iii) a DNA polymerase
to simultaneously amplify the target cDNA region and the target DNA region in a pre-amplification step; and
(d) analyzing the amplified target cDNA region and/or the amplified target DNA region.

In one embodiment, prior to step (a) of the method of the sixth aspect, the cells are isolated from the sample using the method of the second aspect or any cell capture and retrieval methods known in the art.

Advantageously, the simultaneous amplification of the target cDNA region and the target DNA region in step (d) of the fourth aspect or step (c) of the sixth aspect (see scrmPCR as described in Example 3) may form a pre-amplification step that increases the amount of cDNA and/or DNA as templates for further amplification of the target cDNA and/or target DNA regions prior to analysis. The target DNA region may be a target genomic DNA region.

The term "primer" refers to an oligonucleotide which, when paired with a strand of DNA or RNA, is capable of initiating the synthesis of a primer extension product in the presence of a suitable polymerising agent. The primer is preferably single-stranded for maximum efficiency in amplification but may alternatively be double-stranded. A primer must be sufficiently long to prime the synthesis of extension products in the presence of the polymerisation agent. The length of the primer depends on many factors, including application, temperature to be employed, template reaction conditions, other reagents, and source of primers. For example, depending on the complexity of the target sequence, the oligonucleotide primer typically contains 15 to 35 or more nucleotides, although it may contain fewer nucleotides. Primers can be large polynucleotides, such as from about 200 nucleotides to several kilobases or more. Primers may be selected to be "substantially complementary" to the sequence on the template to which it is designed to hybridise and serve as a site for the initiation of synthesis. For example, not all bases in the primer need to reflect the sequence of the template molecule to which the primer will hybridize—the primer need only contain sufficient complementary bases to enable the primer to hybridize to the template. The primer may include additional bases, for example in the form of a restriction enzyme recognition sequence at the 5' end, to facilitate cloning of the amplified DNA. A primer may also include mismatch bases at one or more positions, being bases that are not complementary to bases in the template, but rather are designed to incorporate changes into the DNA upon base extension or amplification.

The term "amplification" or "amplify" relates to the production of additional copies of a nucleic acid. Amplification may be carried out using polymerase chain reaction (PCR) technologies or other nucleic acid amplification technologies well known in the art.

"Primer pairs" can be used for amplification (and identification) of a nucleic acid, e.g., by the polymerase chain reaction (PCR). The "primer pair" may comprise a "forward primer" and a "reverse primer". In a PCR reaction, both strands of a double stranded DNA are amplified. The "forward primer" may bind to one strand of the DNA and allow the synthesis of a primer extension product from the 5' to 3' direction. The "reverse primer" may bind to the complementary strand of DNA, and also allows the synthesis of a primer extension product in the 5' to 3' direction of the complementary DNA strand. In a reverse transcription reaction, the "reverse primer" may bind to an RNA strand and allow the synthesis of a complementary DNA (cDNA) strand in a 5' to 3' direction of the cDNA strand in the presence of a reverse transcriptase enzyme. The "reverse primer" may subsequently be used together with a "forward primer" to amplify the synthesized cDNA strand. PCR primer pairs can be derived from a known sequence, for example, by using computer programs intended for that purpose such as Primer (Version 0.5, 1991, Whitehead Institute for Biomedical Research, Cambridge Mass.) and those used in the Examples disclosed herein (e.g. PrimerBLAST). Oligonucleotides for use as primers are selected using software known in the art for such purpose. For example, OLIGO 4.06 software is useful for the selection of PCR primer pairs of up to 30-100 nucleotides each, and for the analysis of oligonucleotides and larger polynucleotides of up to 5,000 nucleotides from an input polynucleotide sequence of up to 32 kilobases.

The methods and reagents for use in PCR amplification reactions, restriction enzyme digestion and subsequent fragment resolution, and nucleic acid sequencing are well known to those skilled in the art. In each case, suitable protocols and reagents will largely depend on individual circumstances. Guidance may be obtained from a variety of sources, such as for example Sambrook et al., Molecular Cloning: A Laboratory Manual, Cold Spring Harbor, N.Y., 1989, and Ausubel et al., Current Protocols in Molecular Biology, Greene Publ. Assoc. and Wiley-Intersciences, 1992. A person skilled in the art would readily appreciate that various parameters of these procedures may be altered without affecting the ability to achieve the desired product. For example, in the case of PCR amplification, the salt concentration may be varied. Similarly, the amount of DNA used as a template may also be varied depending on the amount of DNA available or the optimal amount of template required for efficient amplification.

A skilled person would be able to understand that a "reverse transcriptase" is an enzyme that may be used to synthesise cDNA based on an RNA template. A skilled person would also understand that a "DNA polymerase" is an enzyme that can synthesise DNA molecules based on a DNA template.

By "contacting", a primer may be brought into physical association with a sample. This allows, for example, a primer pair to anneal with the DNA present in the sample, and subsequently amplify the DNA by PCR. This also allows a primer to anneal to an RNA strand present in the sample, to allow synthesis of cDNA using a reverse transcriptase enzyme as known to a person skilled in the art.

The term "analyze" or "analyzing" refers to studying or examining the amplified target cDNA region and/or the amplified target DNA region by various techniques known in the art. The amplified cDNA region and/or the amplified target DNA region may be studied for its gene expression or for mutations that may be present.

The inventors have found that specific amplification of both DNA and RNA can be achieved by using at least a semi-nested approach for RNA and a fully nested approach for DNA molecules. The term "semi-nested PCR" as used herein refers to a modified PCR technique in which one "nested primer" is used to reduce non-specific binding due to the amplification of unexpected binding sites. A "fully nested approach" would refer to a modified PCR technique where two nested primers are used on either side on a template DNA. The use of "nested primers" allow the specific recognition of a PCR product amplified using a first set of primers, thus eliminating contamination from unwanted products such as primer dimers, hairpins and alternative primer target sequences. The inventors have also found that amplification of DNA and RNA molecules are differentially affected by annealing temperature in the pre-amplification step. A trade-off therefore needs to be set in order to amplify both molecules.

Accordingly, one embodiment of the method of the fourth aspect or further comprises the step of: subjecting the sample from step (d) to a semi-nested PCR using the reverse primer in step (c) or the forward primer in step (d)(i), and a nested primer that binds within the amplified target cDNA region. Another embodiment of the method of the fourth aspect further comprises the step of: subjecting the sample from step (d) to a nested PCR using a nested primer pair that binds within the amplified target DNA region.

Similarly, one embodiment of the method of the sixth aspect further comprises the step of: subjecting the sample from step (c) to a semi-nested PCR using the reverse primer in step (b) or the forward primer in step (c)(i), and a nested primer that binds within the amplified target cDNA region. Another embodiment of the method of the sixth aspect further comprises the step of: subjecting the sample from step (c) to a nested PCR using a nested primer pair that binds within the amplified target DNA region.

In one embodiment, steps (c) and (d) of the method of the fourth aspect or steps (b) and (c) of the method of the sixth aspect are conducted in the same reaction mixture.

In one embodiment, the analysis in step (e) of the fourth aspect or step (d) of the sixth aspect comprises analyzing the amplified target cDNA for gene expression (e.g. in a gene expression analysis). The gene expression analysis may be conducted using any techniques known in the art, such as quantitative PCR, digital PCR, microarray, and the like.

In one embodiment, the analysis in step (e) of the fourth aspect or step (d) of the sixth aspect comprises analyzing the amplified target cDNA for mutations (e.g in a mutational analysis). The mutational analysis may be conducted using any techniques known in the art, such as Sanger sequencing, Maxam-Gilbert sequencing, Pyrosequencing, Shot-gun sequencing, high-throughput DNA sequencing, Allele-Specific PCR (ASPCR) or High Resolution Melting temperature PCR (HRM).

The method according to the fourth aspect or the sixth aspect can be performed simultaneously for one or more target RNA regions, and/or one or more target cDNA regions, and/or one or more target DNA regions. Accordingly, one or more reverse primers, each having the same or a differing specificity for a target RNA region may be used in step (c) of the fourth aspect or step (b) of the sixth aspect, one or more forward primers, each having the same or a differing specificity for a target cDNA region may be used in step (d)(i) of the fourth aspect or step (c)(i) of the sixth aspect, one or more primer pairs, each having the same or a differing specificity for a target DNA region may be used in step (d)(ii) of the fourth aspect or step (c)(ii) of the sixth aspect, one or more nested primers that bind to a target cDNA region, and one or more nested primer pairs that bind to a target DNA region, may be used.

The first primer pair may comprise primers that span exon-exon boundaries or are separated by at least one intron on the corresponding DNA region. The second primer pair may comprise primers that bind to intronic regions of the target DNA region.

The term "exon" refers to the portion of the genomic DNA that becomes a part of the genomic DNA that is converted into the mature messenger mRNA. The term "intron" or "intronic region" refers to the portion of the genomic DNA that is removed by RNA splicing and which would therefore not be present in the final mature mRNA.

In one embodiment, the first primer pair used can be any one or more of the primer pairs listed in Table 1.

TABLE 1

Primer pairs used for preamplification step

| Gene name | ID (transcript or gene) | Marker | Preamplification step Forward primer | Reverse primer |
|---|---|---|---|---|
| SERPINE1 | NT_007933.15 | EMT | GCCAAGAGCGCTGTCAA (SEQ ID NO: 1) | CAGCAGACCCTTCACCAAA (SEQ ID NO: 2) |
| VIM | NM_003380.3 | EMT | GATGTTTCCAAGCCTGACCT (SEQ ID NO: 3) | CAGTGGACTCCTGCTTTGC (SEQ ID NO: 4) |
| FOXC1 | NM_001453.2 | EMT | CACACCCTCAAAGCCGAACT (SEQ ID NO: 5) | AAAGTGGAGGTGGCTCTGAA (SEQ ID NO: 6) |
| KRT8 | NM_002273.3 | EMT/L(Ep) | AAGGATGCCAACGCCAAGTT (SEQ ID NO: 7) | CCGCTGGTGGTCTTCGTATG (SEQ ID NO: 8) |
| EPCAM | NT_022184.15 | EMT/L(Ep) | GCAGGTCCTCGCGTTCG (SEQ ID NO: 9) | TCTCCCAAGTTTTGAGCCATTC (SEQ ID NO: 10) |
| PTPRC | NT_004487.19 | L(He) | GACATCATCACCTAGCAGTTCATG (SEQ ID NO: 11) | CAGTGGGGAAGGTGTTGG (SEQ ID NO: 12) |
| VWF | NM_000552.3 | L(En) | ACACAGGGGGACCAAAGAG (SEQ ID NO: 13) | GAGATGCCCGTTCACACCA (SEQ ID NO: 14) |
| PECAM1 | NM_000442.4 | L(He, En) | TCTCAACGGTGACTTGTGG (SEQ ID NO: 15) | GTTCTTCCCATTTTGCACCGT (SEQ ID NO: 16) |
| MCAM | NM_006500.2 | L(En) | CTCGGTCCCAGGAGTACC (SEQ ID NO: 17) | TGTACAAACCACTCGACTCCA (SEQ ID NO: 18) |
| ITGA2B | NM_000419.3 | L(Me) | CTTCTATGCAGGCCCCAAT (SEQ ID NO: 19) | AGCCTACATTTCGGGTCTCATC (SEQ ID NO: 20) |
| CD34 | NM_001773.2 | S/L(En) | CCTTCTGGGTTCATGAGTCTTGACA (SEQ ID NO: 21) | TGTCGTTTCTGTGATGTTTGTTGTG (SEQ ID NO: 22) |
| FOLH1 | NT_009237.18 | TEC | CGGATATTGTACCACCTTTCAGT (SEQ ID NO: 23) | AGCAGGGTCGGAGTAGAGAA (SEQ ID NO: 24) |
| ENG | NT_008470.19 | L(En) | GTGACGGTGAAGGTGGAACTGA (SEQ ID NO: 25) | TTGAGGTGTGTCTGGGAGCT (SEQ ID NO: 26) |
| KDR | NM_002253.2 | L(En) | GAAATGACACTGGAGCCTACAAG (SEQ ID NO: 27) | AATGGACCCGAGACATGGAAT (SEQ ID NO: 28) |
| CDH5 | NM_001795.3 | L(En) | GTTCACGCATCGGTTGTTCAAT (SEQ ID NO: 29) | GCCTGCTTCTCTCGGTCCAA (SEQ ID NO: 30) |
| TEK | NT_008413.19 | L(En) | CTTATTTCTGTGAAGGGCGAGTT (SEQ ID NO: 31) | CTCCCTTGTCCACAGTCATAGT (SEQ ID NO: 32) |
| ANGPT2 | NM_001147.2 | L(En) | AACACTCCCTCTCGACAAACAAATT (SEQ ID NO: 33) | CTGTAGTTGGATGATGTGCTTGTC (SEQ ID NO: 34) |
| KRT18 (1) | NM_000224.2 | EMT/L(Ep) | TGCTCACCACACAGTCTGAT (SEQ ID NO: 52) | CACTTTGCCATCCACTAGCC (SEQ ID NO: 53) |
| KRT19 | NM_002276.4 | EMT/L(Ep) | CAGCCACTACTACACGACCA (SEQ ID NO: 54) | CGTTGATGTCGGCCTCCA (SEQ ID NO: 55) |

REFERENCE (1) derived from Hesse et al. (2001) J. Cell Sci. 114, 2569

LEGEND

EMT: Epithelial-mesenchymal transition marker
L: Lineage marker
TEC: Tumor endothelial cell marker
S: Stem cell marker
Ep: Epithelial marker
He: Hematopoietic cell marker
En: Endothelial cell marker
Me: Megakaryocyte/platelet marker In one embodiment, the second primer pair used can be any one or more of the primer pairs listed in Table 2.

TABLE 2

Primer pairs used for amplification step

| Gene name | Allows DNA/RNA discrimination | Forward primer | Reverse primer |
|---|---|---|---|
| SERPINE1 | 1148 bp intron in DNA sequence | AGAACTTCAGGATGCAGATGTCT (SEQ ID NO: 35) | CAGCAGACCCTTCACCAAA (SEQ ID NO: 2) |
| VIM | 761 bp intron in DNA sequence | GATGTTTCCAAGCCTGACCT (SEQ ID NO: 3) | TGTACCATTCTTCTGCCTCCT (SEQ ID NO: 36) |
| FOXC1 | NA (single exon coding gene) | CACACCCTCAAAGCCGAACT (SEQ ID NO: 5) | GAGGGATATTCTGTTCGCTGGT (SEQ ID NO: 37) |
| KRT8 | 159 bp intron in DNA sequence | GCTGGAGGGCGAGGAGA (SEQ ID NO: 38) | CCGCTGGTGGTCTTCGTATG (SEQ ID NO: 8) |
| EPCAM | 4118 bp intron in DNA sequence | CCGCAGCTCAGGAAGAATGT (SEQ ID NO: 39) | TCTCCCAAGTTTTGAGCCATTC (SEQ ID NO: 10) |
| PTPRC | 53092 bp intron in DNA sequence | CAACAGTGGAGAAAGGACGCA (SEQ ID NO: 40) | CAGTGGGGGAAGGTGTTGG (SEQ ID NO: 12) |
| VWF | Forward primer on exon junction | TGCCTCCAAAGGGCTGTATC (SEQ ID NO: 41) | GAGATGCCCGTTCACACCA (SEQ ID NO: 14) |
| PECAM1 | 12457 bp intron in DNA sequence | CAGTCTTCACTCTCAGGATGC (SEQ ID NO: 42) | GTTCTTCCCATTTTGCACCGT (SEQ ID NO: 16) |
| MCAM | 1724 bp intron in DNA sequence | CTCGGTCCCAGGAGTACC (SEQ ID NO: 17) | CGGCCATTCTTGTACCAGATGA (SEQ ID NO: 43) |
| ITGA2B | 3242 bp intron in DNA sequence | GGCGGCGTGTTCCTGT (SEQ ID NO: 44) | AGCCTACATTTCGGGTCTCATC (SEQ ID NO: 20) |
| CD34 | Forward and reverse primers on exon junction | CTACCCCAGAGTTACCTACCCA (SEQ ID NO: 45) | TGTCGTTTCTGTGATGTTTGTTGTG (SEQ ID NO: 22) |
| FOLH1 | 6811 bp intron in DNA sequence | CCAGAGGGCGATCTAGTGTA (SEQ ID NO: 46) | AGCAGGGTCGGAGTAGAGAA (SEQ ID NO: 24) |
| ENG | 256 bp intron in DNA sequence | GTGACGGTGAAGGTGGAACTGA (SEQ ID NO: 25) | AGTATTCTCCAGTGGTCCAGATCT (SEQ ID NO: 47) |
| KDR | 3192 bp intron in DNA sequence | GAAATGACACTGGAGCCTACAAG (SEQ ID NO: 27) | TGTTGGTCACTAACAGAAGCA (SEQ ID NO: 48) |
| CDH5 | 2143 bp intron in DNA sequence | CACGCCTCTGTCATGTACCA (SEQ ID NO: 49) | GCCTGCTTCTCTCGGTCCAA (SEQ ID NO: 30) |
| TEK | 10352 bp intron in DNA sequence | CTTATTTCTGTGAAGGGCGAGTT (SEQ ID NO: 31) | GTAGCTGGTAGGAAGGAAGCT (SEQ ID NO: 50) |
| ANGPT2 | 6144 bp intron in DNA sequence | GGACCAGACCAGTGAAATAAACAA (SEQ ID NO: 51) | CTGTAGTTGGATGATGTGCTTGTC (SEQ ID NO: 34) |
| KRT18(1) | 641 bp introns in DNA sequence | TGGAGGACCGCTACGCCCTA (SEQ ID NO: 56) | CCAAGGCATCACCAAGACTA (SEQ ID NO: 57) |
| KRT19 | 2745 bp intron in DNA sequence | TGCGGGACAAGATTCTTGGT (SEQ ID NO: 58) | CGTTGATGTCGGCCTCCA (SEQ ID NO: 55) |

Reference:
(1) derived from Hesse et al. (2001) J. Cell Sci. 114, 2569

The pre-amplification in step (d) of the method of the fourth aspect may comprise one or more cycling steps. Each cycling step may comprise one or more cycles of amplification (i.e. denaturation, annealing and elongation) at a pre-determined temperature for a pre-determined duration. It would be appreciated that the number of cycling steps, the number of cycles of denaturation, annealing and elongation, the temperature(s) at which these are conducted, and the duration for which each temperature is applied would depend on factors such as the reagents used in the amplification reactions, the target cDNA or DNA region, the primers used, the sample(s) to be amplified, etc. In one embodiment, the amplification does not include a final extension step.

For example, step (d) may comprise about 1 to about 60 cycling steps, about 1 to about 50 cycling steps, about 1 to about 40 cycling steps, about 1 to about 30 cycling steps, about 1 to about 25 cycling steps, about 1 to about 20 cycling steps, about 1 to about 15 cycling steps, about 1 to about 10 cycling steps, about 1 to about 5 cycling steps, about 1 to about 4 cycling steps, about 1 to about 3 cycling steps, about 1 cycling step, about 2 cycling steps, or about 3 cycling steps.

Each cycling step may comprise about 1 to about 50 cycles, about 1 to about 40 cycles, about 1 to about 30 cycles, about 1 to about 25 cycles, about 1 to about 20 cycles, about 1 to about 18 cycles, about 1 to about 15 cycles, about 1 to about 10 cycles, about 1 to about 6 cycles, about 2 cycles, about 4 cycles, about 6 cycles, about 8 cycles, about 10 cycles, about 15 cycles about 20 cycles, about 25 cycles, about 30 cycles, about 40 cycles, or about 50 cycles of denaturation, annealing and elongation.

In some examples, the annealing and/or elongation temperature in a cycle is about 40° C. to about 80° C., about 40° C. to about 75° C., about 40° C. to about 70° C., about 40° C. to about 65° C., about 40° C. to about 60° C., about 40° C. to about 55° C., about 40° C. to about 50° C., about 40° C., about 45° C., about 50° C., about 55° C., about 60° C., about 65° C., about 70° C., about 75° C. or about 80° C.

The annealing and/or elongation temperature for successive cycling steps may be reduced by about 1° C. to about 10° C., about 1° C. to about 9° C., about 1° C. to about 8° C., about 1° C. to about 7° C., about 1° C. to about 6° C., about 1° C. to about 5° C., about 1° C. to about 4° C., about 1° C. to about 3° C., or about 1° C. to about 2° C.

In some examples, the annealing and/or elongation can be carried out for about 10 seconds to about 10 minutes, about 10 seconds to about 8 minutes, about 10 seconds to about 6 minutes, about 10 seconds to about 4 minutes, about 10 seconds to about 2 minutes, about 10 seconds to about 1 minute, about 1 minute, about 2 minutes, about 4 minutes, about 6 minutes, about 8 minutes, or about 10 minutes.

In some examples, the denaturation can be carried out at a temperature of about 75° C. to about 120° C., about 75° C. to about 115° C., about 75° C. to about 110° C., about 75° C. to about 105° C., about 75° C. to about 100° C., about 75° C. to about 95° C., about 75° C. to about 90° C., about 75° C. to about 85° C., about 75° C. to about 80° C., about 75° C., about 80° C., about 85° C., about 90° C., about 95° C., about 100° C., about 105° C., about 110° C., about 115° C., or about 120° C.

The denaturation may be carried out for about 1 second to about 10 minutes, about 1 second to about 5 minutes, about 1 second to about 4 minutes, about 1 second to about 3 minutes, about 1 second to about 2 minutes, about 1 second to about 1 minute, about 1 second, about 10 seconds, about 20 seconds, about 30 seconds, about 40 seconds, about 50 seconds, about 1 minute, about 2 minutes, about 3 minutes, about 4 minutes, about 5 minutes, or about 10 minutes.

In one example, step (d) of the method comprises:
6 cycles of 60° C. for 4 minutes followed by 95° C. for 1 minute,
6 cycles of 55° C. for 4 minutes followed by 95° C. for 1 minute, and
6 cycles of 50° C. for 4 minutes followed by 95° C. for 1 minute.

In some examples, the lysed cell sample from step (b) comprises cell-free RNA, or cell-free DNA.

Advantageously, the method according to the fourth aspect or the sixth aspect can be used to analyze RNA and DNA in instances where a limited amount of sample is available, for example in rare cell samples.

In some examples, the RNA or DNA may be present in a low amount, for example from about 1 pg to about 10 ng, about 5 pg to about 10 ng, about 5 pg to about 5 ng, about 5 pg to about 1 ng, about 5 pg to about 500 pg, about 5 pg to about 250 pg, about 5 pg to about 125 pg, about 5 pg to about 100 pg, or about 5 pg to about 50 pg.

The methods described herein can be used for diagnosis, in particular for the diagnosis of cancers. Thus, in a seventh aspect, there is provided a method of diagnosing a cancer in a subject, comprising analyzing a sample from the subject for presence of the isolated population of cells as described herein, wherein presence of the isolated population of cells indicates that the subject has cancer. One example of the detection of TECCs in cancer patients is shown in Example 3.

In some examples, the isolated population of cells is considered as "present" if it is detectable above the background noise of the respective detection method used (e.g., 2-fold, 3-fold, 5-fold, or 10-fold higher than the background; e.g., 2-fold or 3-fold over background).

The subject may be a mammal, for example human.

The major types of cancers that can be diagnosed by the method as described herein include but are not limited to carcinoma, sarcoma, lymphoma, germ cell tumor and blastoma. The specific types of cancers that can be diagnosed by the method as described herein include but are not limited to colon cancer, rectal cancer, breast cancer, prostate cancer, renal cell cancer, transitional cell carcinoma, lung cancer, cholangiocarcinoma, colon cancer, brain cancer, non-small cell lung cancer, pancreatic cancer, gastric carcinoma, bladder cancer, esophageal cancer, mesothelioma, melanoma, thyroid cancer, head and neck cancer, osteosarcoma and gliobastoma. A person skilled in the art will understand that the term "colorectal cancer" can be used to refer to colon cancer and rectal cancer. Specifically, when a colorectal cancer originates from the colon, it is considered as a colon cancer, and when a colorectal cancer originates from the rectum, it is considered as a rectal cancer.

In one embodiment, the cancer is invasive and/or metastatic cancer. In another embodiment, the cancer is stage I cancer, stage II cancer, stage III cancer or stage IV cancer. In a further embodiment, the cancer is early stage cancer, such as pre-operative stage cancer. An example of an early stage cancer is a primary tumor. The methods as described herein care particularly useful for the detection of early stage cancer due to the ability of the method to capture and retrieve cells that are present in very low numbers, such as those in early stage cancers, for analysis.

The methods as described herein can be used for monitoring and/or predicting the response to treatment of a cancer patient. Thus, in an eighth aspect, there is provided a method for monitoring and/or predicting the response to treatment of a cancer patient, the method comprising analyzing a sample obtained from the patient after treatment for determining the number of the isolated population of cells as described herein, wherein a reduction in the number of the isolated population of cells compared to the number of the isolated population of cells in a baseline sample obtained from the patient prior to treatment indicates that the patient is responding positively to the treatment. Similarly, in a ninth aspect, there is provided a method for predicting the response to treatment of a cancer patient, the method comprising analyzing a sample obtained from the cancer patient before treatment for determining the number of the isolated population of cells as described herein, wherein an equal or higher number of the isolated population of cells compared to the number of the isolated population of cells in a sample obtained before treatment from a patient or a group of patients that have responded positively to the treatment indicates that the cancer patient will respond positively to the treatment, and wherein a lower number of the isolated population of cells compared to the number of the isolated population of cells in a sample obtained before treatment from a patient or a group of patients that have responded positively to the treatment indicates that the cancer patient will respond negatively to the treatment.

The isolated population of cells is considered as "absent" if it is not detectable above the background noise of the detection method used (e.g., <1.5-fold or <2.0-fold higher than the background signal; e.g., <1.5-fold or <2.0-fold over background). The term "reduction", "reduced" or "lower" refers to a decrease in the number of the isolated population of cells relative or compared to a baseline sample or control. The baseline or control may be a sample obtained from the same subject prior to treatment, or a sample obtained from a normal, healthy subject, or a group of normal, healthy subjects, or a sample obtained from a patient or a group of patients that have responded to the treatment in a preliminary study. In some examples, the number of the isolated population of cells in the baseline or control sample is from 1 to 5, 1 to 10, 1 to 15, 1 to 20, 1 to 25, 1 to 30, 1 to 30, 1 to 40 or 1 to 50/ml of blood. In some examples, the reduced or lower number of the isolated population of cells is reduced by at least 10%, at least 20%, at least 30%, at least 40%, at least 50%, at least 60%, at least 70%, at least 80%, at least 90% or at least 95% as compared to the number of the isolated population of cells in a baseline or control sample. The term "increased" or "higher" refers to an increase in the number of the isolated population of cells relative or compared to a baseline sample or control. The baseline or control may be a sample obtained from the same subject prior to treatment, or a sample obtained from a normal, healthy subject or a sample obtained from a patient that has responded to the treatment in a preliminary study. In some examples, the increased or higher number of the isolated population of cells is at least about 1.05 times, at least about 1.1 times, at least about 1.2 times, at least about 1.3 times, at least about 1.4 times, at least about 1.5 times, at least about 1.6 times, at least about 1.7 times, at least about 1.8 times, at least about 1.9 times or at least about 2.0 times the number of the isolated population of cells in a baseline or control sample.

In some examples, the response to treatment of a cancer patient will be negative if the number of the isolated population of cells is less than 100/ml, less than 90/ml, less than 80/ml, less than 70/ml, less than 60/ml, less than 50/ml, less than 40/ml, less than 30/ml, less than 20/ml, less than 15/ml, less than 10/ml, less than 9/ml, less than 8/ml, less than 7/ml, less than 6/ml, less than 5/ml, less than 4/ml, less than 3/ml, less than 2/ml or less than 1/ml of blood.

In some other examples, the response to treatment of a cancer patient will be positive if the number of the isolated population of cells is more than 1/ml, more than 2/ml, more than 3/ml, more than 4/ml, more than 5/ml, more than 6/ml, more than 7/ml, more than 8/ml, more than 9/ml, more than 10/ml, more than 15/ml, more than 20/ml, more than 30/ml, more than 40/ml, more than 50/ml, more than 60/ml, more than 70/ml, more than 80/ml, more than 90/ml or more than 100/ml of blood.

A person skilled in the art will appreciate that a number of methods can be used to determine the presence, absence or the increase or decrease in the expression of a biomarker, including microscopy based approaches, including fluorescence scanning microscopy (see, e.g., Marrinucci D. et al, 2012, Phys. Biol. 9016003), mass spectrometry approaches, such as MS/MS, LC-MS/MS, multiple reaction monitoring (MRM) or SRM and production monitoring (PIM) and also including antibody based methods such as immunofluorescence, immunohistochemistry, immunoassays such as Western blots, enzyme-linked immunosorbant assay (ELISA), immunoprecipitation, radioimmunoassay, dot blotting, Fluorescence-activated cell sorting (FACS) and mass cytometry. Immunoassay techniques and protocols are generally known to those skilled in the art (Price and Newman, Principles and Practice of Immunoassay, 2nd Edition, Grove's Dictionaries, 1997; and Gosling, Immunoassays: A Practical Approach, Oxford University Press, 2000.) A variety of immunoassay techniques, including competitive and non-competitive immunoassays, can be used (Self et al, Curr. Opin. Biotechnol 7:60-65 (1996), see also John R. Crowther, The ELISA Guidebook, $1^{st}$ ed., Humana Press 2000, ISBN 0896037282 and, An Introduction to Radioimmunoassay and Related Techniques, by Chard T, ed., Elsevier Science 1995, ISBN 0444821 198).

A person of skill in the art will further appreciate that the presence, absence or the increase or decrease in the expression of biomarkers may be detected using any class of marker-specific binding reagents known in the art, including, e.g., antibodies, aptamers, fusion proteins, such as fusion proteins including protein receptor or protein ligand components (e.g. CD31, VWF, CD144, CD 45, CD41, or CD42B binding receptors or ligands), or biomarker-specific small molecule binders.

The isolated population of cells as described herein are mainly of endothelial nature. Since endothelial cells line the interior of all blood vessels, the method as described herein can also be used for analyzing blood vessel characteristics of a tumor. Thus, in a tenth aspect, there is provided a method for analyzing blood vessel characteristics of a tumor in a subject, the method comprising analyzing a sample from the subject for determining the number of the isolated population of cells as described herein, wherein an increased number of the isolated population of cells compared to a baseline sample indicates that the tumor has larger blood vessels compared to the baseline sample, and wherein a reduced number of the isolated population of cells compared to a baseline sample indicates that the tumor has smaller blood vessels compared to the baseline sample.

In some examples, a baseline sample or a control sample is obtained from a patient shown to have small blood vessels in a preliminary study. In some examples, the number of the isolated population of cells in the baseline or control sample is from 1 to 5, 1 to 10, 1 to 15, 1 to 20, 1 to 25, 1 to 30, 1 to 30, 1 to 40 or 1 to 50/ml of blood. In some examples, the increased number of the isolated population of cells is at least about 1.05 times, at least about 1.1 times, at least about 1.2 times, at least about 1.3 times, at least about 1.4 times, at least about 1.5 times, at least about 1.6 times, at least about 1.7 times, at least about 1.8 times, at least about 1.9 times or at least about 2.0 times the number of the isolated population of cells in a baseline or control sample. In some examples, the reduced number of the isolated population of cells is reduced by at least 10%, at least 20%, at least 30%, at least 40%, at least 50%, at least 60%, at least 70%, at least 80%, at least 90% or at least 95% as compared to the number of the isolated population of cells in a the number of the isolated population of cells in a baseline or control sample.

In some examples, a patient is classified as having large blood vessels in the tumor if the number of the isolated population of cells is more than 1/ml, more than 2/ml, more than 3/ml, more than 4/ml, more than 5/ml, more than 6/ml, more than 7/ml, more than 8/ml, more than 9/ml, more than 10/ml, more than 15/ml, more than 20/ml, more than 30/ml, more than 40/ml, more than 50/ml, more than 60/ml, more than 70/ml, more than 80/ml, more than 90/ml or more than 100/ml of blood.

In some other examples, a patient is classified as having small blood vessels in the tumor if the number of the isolated population of cells is less than 100/ml, less than 90/ml, less than 80/ml, less than 70/ml, less than 60/ml, less than 50/ml, less than 40/ml, less than 30/ml, less than 20/ml, less than 15/ml, less than 10/ml, less than 9/ml, less than 8/ml, less than 7/ml, less than 6/ml, less than 5/ml, less than 4/ml, less than 3/ml, less than 2/ml or less than 1/ml of blood.

In some examples, the response to treatment of a cancer patient will be positive if the patient has larger blood vessels in the tumor. In some other examples, the response to treatment of a cancer patient will be negative if the patient has smaller blood vessels in the tumor.

It is also envisaged that commercial kits may be developed for rapid capturing, retrieval and/or detection of the isolated cell population, for the diagnosis, monitoring and/or predicting the response to treatment, and/or for the analysis of the blood vessel characteristics of tumor as described herein. Thus, in an eleventh aspect, there is provided a kit for use in the methods as described herein (such as methods of the second, the fourth, the seventh, the eighth, the ninth or the tenth aspects), wherein the kit comprises (a) the apparatus as described herein.

The kit of the eleventh aspect may further comprise one or more of the following:
(b) one or more cell lysis buffers for lysing the cells obtained from a sample;
(c) a primer selected from the group consisting of:
i. the reverse primer of step (c) of the method of the fourth aspect;
ii. the forward primer of step (d)(i) of the method of the fourth aspect,
iii. the primer pair of step (d)(ii) of the method of the fourth aspect, and
iv. the nested primer and nested primer pair of the method of the fourth aspect;
(d) one or more reagents, selected from the group consisting of:
i. a reverse transcriptase and one or more suitable reaction buffers for the reverse transcription in step (c) of the method of the fourth aspect,
ii. a DNA polymerase and one or more suitable reaction buffers for the amplification in step (d) of the method of the fourth aspect or the semi-nested or nested PCR of the method of the fourth aspect, and
iii. one or more labelled or unlabelled deoxyribonucleotides selected from the group consisting of dATP, dCTP, dGTP, and dTTP or dUTP; and
(e) an antibody capable of specific binding to a protein selected from the group consisting of PAI-1, Vimentin, FOXC1, keratin-8, keratin-18, keratin-19, Ep-CAM, CD45, VWF, PECAM-1, CD146, CD41, CD34, PSMA, CD105, CD309, CD144, CD202B and Angiopoietin 2, wherein the antibody is coupled to a detectable label as described herein; and optionally means for detecting the detectable label.

In a twelfth aspect, there is provided a kit for use in the methods described herein (such as methods of the fifth, the sixth, the seventh, the eighth, the ninth or the tenth aspects), the kit comprising:
(a) one or more cell lysis buffers for lysing the cells obtained from a sample;
(b) a primer selected from the group consisting of:
i. the reverse primer of step (b) of the method of the fifth aspect,
ii. the forward primer of step (c)(i) of the method of the fifth aspect,
iii. the primer pair of step (c)(ii) of the method of the fifth aspect, and
iv. the nested primer and nested primer pair of the method of the fifth aspect;
(c) one or more reagents, selected from the group consisting of:
i. a reverse transcriptase and one or more suitable reaction buffers for the reverse transcription in step (b) of the method of the fifth aspect,
ii. a DNA polymerase and one or more suitable reaction buffers for the amplification in step (c) of the method of the fifth aspect or the semi-nested or nested PCR of the method of the fifth aspect, and
iii. one or more labelled or unlabelled deoxyribonucleotides selected from the group consisting of dATP, dCTP, dGTP, and dTTP or dUTP; and
(d) an antibody capable of specific binding to a protein selected from the group consisting of PAI-1, Vimentin, FOXC1, keratin-8, keratin-18, keratin-19, Ep-CAM, CD45, VWF, PECAM-1, CD146, CD41, CD34, PSMA, CD105, CD309, CD144, CD202B and Angiopoietin 2, wherein the antibody is coupled to a detectable label as described herein; and optionally means for detecting the detectable label.

Lysis buffers commonly used in the art, such as alkaline lysis buffers or cell lysis buffers containing proteinase K, or simply buffers containing a detergent or a compound and/or an enzyme that will disrupt the cell and allow its nucleic acids to be released in solution may be used.

The kit according to the eleventh or twelfth aspect may also include probes or dyes for quantitative real-time PCR. Exemplary probes and dyes include, but are not limited to SYBR green dye, EvaGreen, dsGreen, TaqMan probes, hybridization probes and the like.

The kit may also include instructions for designing one or more of the primers, and/or optimizing the pre-amplification and/or amplification cycling conditions of steps (c) and/or (d) of the method of the fourth aspect or the fifth aspect.

In one embodiment, the primers and/or reagents are pre-mixed in combinations suitable for the lysis, pre-amplification, and amplification steps according to the method of the fourth aspect or the fifth aspect. In another embodiment, the primers are pre-mixed in combinations suitable for analysis of gene expression profiles or mutation signatures. The primers may be ones that have been designed for amplifying one or more target genes of interest.

One embodiment of the kit of the eleventh or the twelfth aspect further comprises instructions for performing the method as described herein.

In one embodiment, the kit comprises one or more containers comprising one or more reaction buffers for performing the methods and/or uses described above. In some embodiments, the kit includes software-driven assay protocols for use in commercial PCR instrumentation (such as the Life Technologies 7500 FastDx or Cepheid SmartCycler® II), which may be provided on a CD.

As used herein, the singular form "a", "an" and "the" include plural references unless the context clearly dictates otherwise. For example, the term "a primer" includes a plurality of primers, including mixtures thereof.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means+/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Certain embodiments may also be described broadly and generically herein. Each of the narrower species and subgeneric groupings falling within the generic disclosure also form part of the disclosure. This includes the generic description of the embodiments with a proviso or negative limitation removing any subject matter from the genus, regardless of whether or not the excised material is specifically recited herein.

EXPERIMENTAL SECTION

Example 1—Device for the Capturing and Retrieval of Cells from Blood

Figure 3:
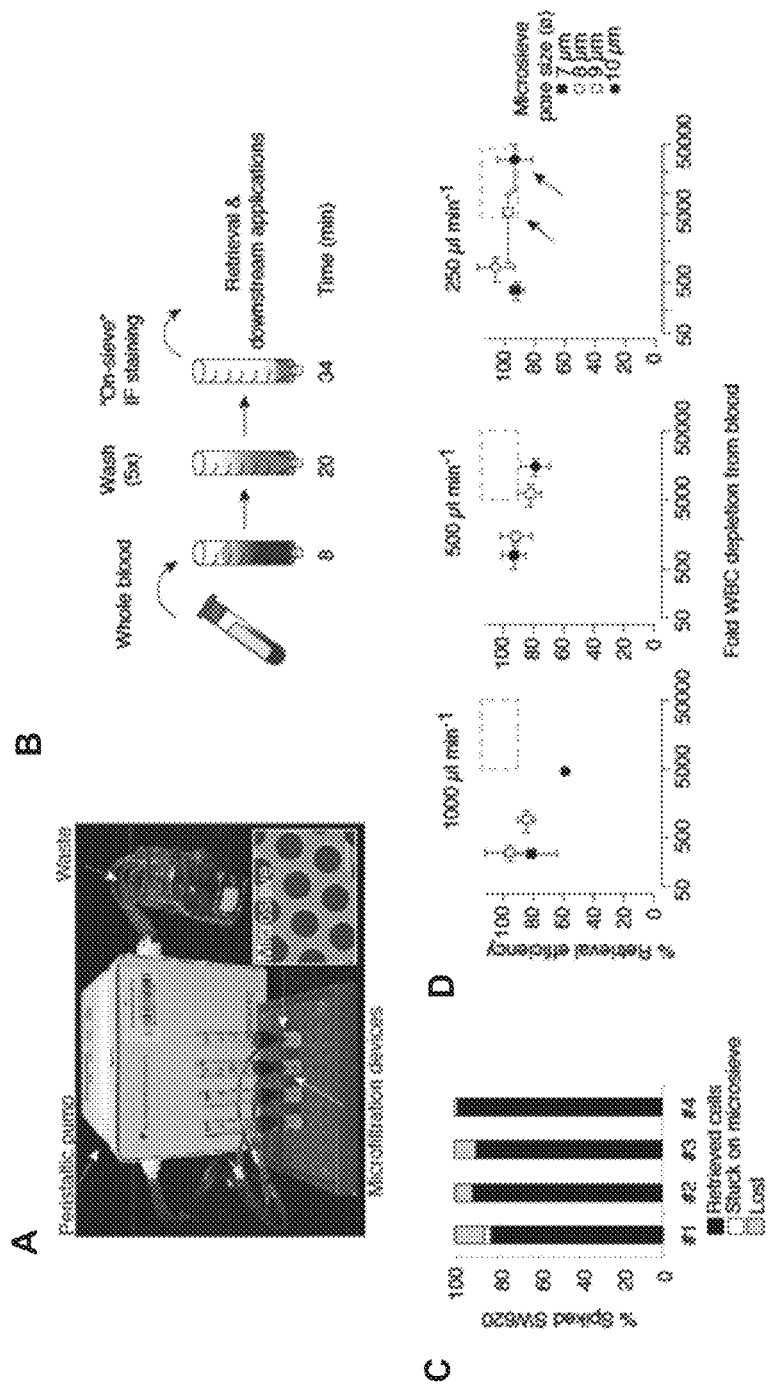
FIG. 3 shows the retrieval of tumor-derived endothelial cell clusters (TECCs) using the microfiltration device described herein. (A) shows an exemplary setup of the microfiltration device described herein, wherein four microfiltration devices each enclosing a silicon microsieve (inset, scale bar=10 µm) are connected to a peristaltic pump for flow rate control. (B) shows the microfiltration procedure for various downstream applications including imaging, counting, single-cell isolation and analysis, cell culture and pooled nucleic acid extraction. The numbers indicate procedure time (in minutes) for each step. The detailed procedures shown in (B) are as follows: whole blood sample (for example, 2 ml) was allowed to filter through the sieve for 8 minutes, washed for 20 minutes, and stained on sieve for 34 minutes for a total time of 62 minutes. Detailed procedures of on-sieve immunofluorescence are described in Example 3. (C) shows that use of silicon microsieves allow efficient retrieval of captured cells. Capture efficiency of SW620 cells from whole blood, indicating % of captured cells on the microsieve that can be retrieved for downstream assays (black bars), that are lost due to adhesion to the microsieve (white bars), or that are lost during the isolation procedure (grey bars). Results of four independent experiments are shown. (D) shows optimization of retrieval efficiency and purity for downstream single-cell micromanipulation. The scatter plots represent experiments using various flow rates and microsieve pore diameters. Black dashed rectangle indicates the target area of >90% retrieval efficiency and >5×10³ WBC depletion for optimal downstream handling of retrieved cells. Data points are means±s.e.m. of three independent experiments under each condition.

FIG. 1A shows the insert sleeve, which has an inlet at the upper end and an outlet at the lower end. The insert sleeve functions as a housing for the cell capturing sieve, securing the cell capture sieve near the outlet of the column of the device. The sample flows in from the inlet of the insert sleeve, and flows out through the outlet of the insert sleeve. FIG. 1B shows that the channel through which the sample flows tapers at the lower end of the insert sleeve. FIG. 1C illustrates the assembly of the insert sleeve and the cell capture sieve within the column. The cell capture sieve (sandwiched between two O-rings) is first placed into the slot near the outlet of the insert sleeve, and then the entire insert sleeve assembly is inserted into the column by using an insert tool in the form of a rod (not shown). FIG. 1D shows two cell capturing and retrieval devices being connected to a peristaltic pump, while FIG. 3A shows another exemplary setup of the microfiltration apparatus with four microfiltration devices each enclosing a silicon microsieve (inset, scale bar=10 μm) connected to a peristaltic pump for flow rate control. A blood sample was filtered through the device. Depletions of contaminating white blood cells (WBCs) and red blood cells (RBCs) using cell capturing sieves with various pore diameters were tested. The results are shown in FIG. 1E. One ml of whole blood was filtered through the device. Contaminating WBCs and RBCs were retrieved and counted (black bars), or retrieved and counted after inverting the flow of the peristaltic pump ("backflushing") for a short time to dislodge cells that were stuck on the sieve (white bars). Fold depletion was calculated as follows:

Fold Depletion of WBCs or RBCs=(WBCs or RBCs in Whole Blood)/(WBCs or RBCs in Microfiltrate)

The bars in FIG. 1E represent the mean value obtained from tests with three different devices for each condition tested. Error bar represents the standard deviation.

TECC enrichment and retrieval efficiency was optimized by spiking 1 ml of donor blood with 30 SW620 cells, a CRC cell line with similar median size as CTCs (FIG. 1F). An optimal tradeoff between retrieval efficiency and cell purity was obtained using a flow rate of 0.25 ml/min and pore diameters of 9-10 μm.

Retrieval efficiency of the device using whole blood spiked with the various cell lines was tested. The results are shown in FIG. 1G, with each dot plot corresponding to an independent experiment. 20 to 50 cells/ml were labeled and spiked in 1 ml or 3 ml of whole blood. Each blood sample was passed through the device, and target cells were retrieved, placed in a 96-well plate and counted. Retrieval efficacy was calculated as follows:

% Retrieval Efficiency=(Retrieved cells)×100/(Spiked Cells)

Figure 2:
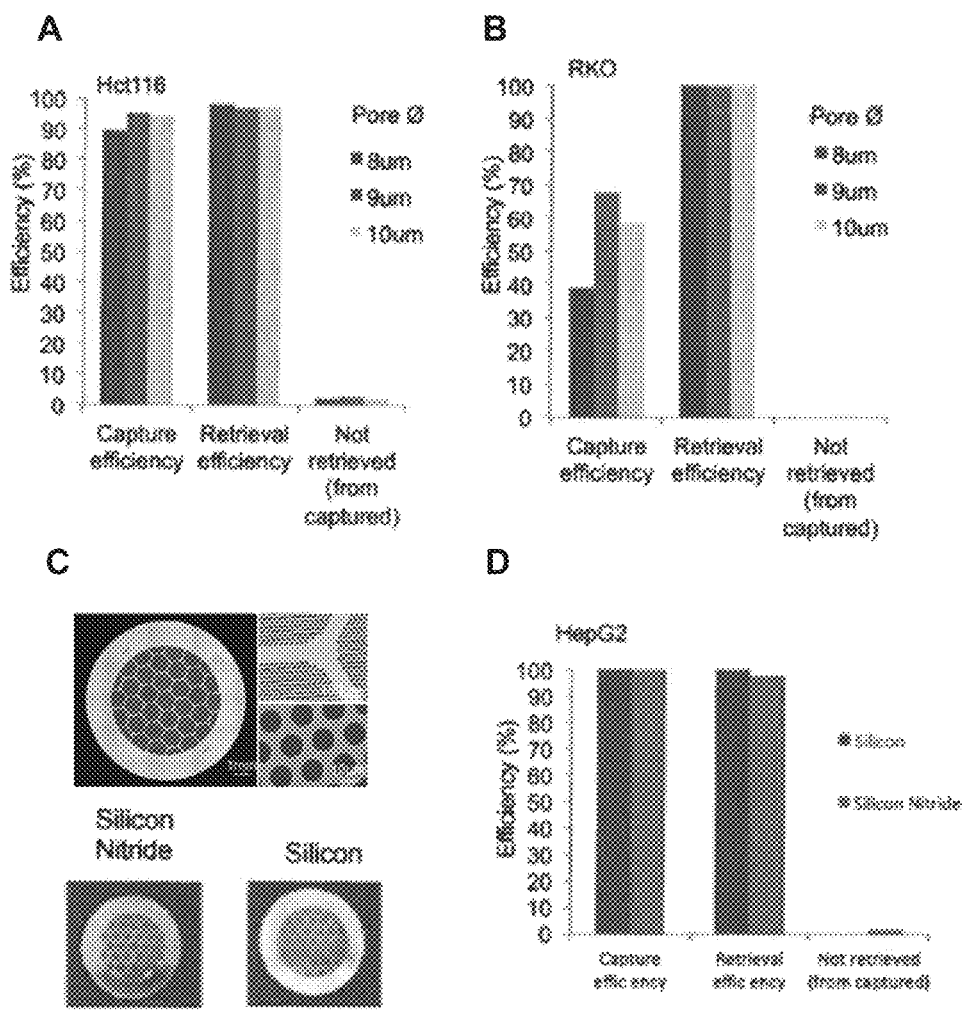
FIG. 2 shows the retrieval efficiency as compared to capture efficiency using the cell capturing and retrieval device described herein, with cell capture sieves having different pore diameters (8 µm, 9 µm, 10 µm). (A) shows the results using HCT 116 cells. For each independent experiment, 30 to 50 HCT 116 cells were spiked in 1 ml of whole blood, and retrieved cells were placed in a 96-well plate and counted. The number of cells remaining on the device was examined. Number of cells captured=number of cells retrieved+number of cells remaining on the device. The result shows that HCT 116 cells could be retrieved with an efficiency of >98%. Capture efficiency=(number of cells captured)×100%/number of spiked cells. Retrieval efficiency=(number of cells retrieved)×100%/number of cells captured. (B) shows the results using RKO cells. Capture efficiency was lower for RKO cells as compared to HCT 116 cells. However, the retrieval efficiency of captured RKO cells was always 100% for all pore diameters of cell capture sieves used. (C) shows a bright field composite image (upper left panel), scanning electron micrographs (upper right panels) of silicon microsieve, and photographs (lower panel) of microsieves with silicon and silicon nitride as different filter materials. (D) shows the cell capturing and retrieval efficiency using different filter materials tested with HepG2 cells, which indicates that the two different filter materials, silicon and silicon nitride, provided similar cell capturing and retrieval efficiency.

The cell retrieval efficiency as compared to capture efficacy using the apparatus was tested using two different cell lines: HCT116 and RKO cell lines. 30 to 50 cells were spiked in 1 ml of whole blood, the retrieved cells were placed in a 96-well plate and counted. The number of cells remaining un-retrieved on the sieve was also counted. Number of cells captured was calculated by combining the number of cells retrieved and the number of cells remaining un-retrieved on the sieve. As shown in FIG. 2A, the capture efficiency for HCT 116 cells was greater than 90% and the retrieval efficiency was greater than 98% using sieve of pore diameters 8 μm, 9 μm and 10 μm. As shown in FIG. 2B, the capture efficiencies for RKO cells using sieve of pore diameters 8 μm, 9 μm and 10 μm were about 40%, 68% and 58% respectively. However, the retrieval efficiency of captured RKO cells was 100% using all three different pore diameters.

Cell capturing and retrieval efficiency using different filter materials shown in FIG. 2C were tested with HepG2 cells. The results shown in FIG. 2D indicate that the two different filter materials, silicon and silicon nitride, provided similar cell capturing and retrieval efficiency.

Example 2—Capturing and Retrieval of Tumor-Derived Endothelial Cell Clusters (TECCs)

Patient samples and clinical data. All subjects had given informed written consent to participate. Clinical samples were obtained between July 2012 and April 2014 according to protocols approved by the Institutional Review Boards (IRB) of the National University of Singapore, Fortis Surgical Hospital and Singapore Health Services (SingHealth). Consecutive blood samples from 82 colorectal cancer patients were provided by Fortis Surgical Hospital (FSH) and National Cancer Center, Singapore (NCC). Blood samples from 45 healthy subjects were provided by the Singapore Consortium of Cohort Studies (SCCS). All samples were collected in EDTA Vacutainer tubes (Becton-Dickinson) and processed within 6 h at the Institute of Bioengineering and Nanotechnology. Two cases were excluded from analysis because of technical failure of the microfiltration device. Wherever available, matched tumor and metastatic samples were immediately frozen after resection, and stored at −80° C. until use. Clinicopathologic data for participating subjects are described in Supplementary Table 6 and were collected retrospectively after completion of TECC counts. Clinical data collection was conducted without prior knowledge of TECC counts. Similarly, clinical data for colorectal cancer patients were not known at the time of TECC count except for diagnosis and preoperative status of FSH samples. Tumor area was calculated by width×length.

Cell lines and culture. HCT 116, COLO 201, SW480, SW620, DLD-1 and RKO colorectal cancer cell lines, BJ-5ta immortalized human foreskin fibroblasts and HUVECs were from ATCC. HUVECs were used at passage 1 and 2 and cultured in EGM-2 medium (Lonza). All other cell lines were cultured in DMEM (Life Technologies) supplemented with 10% FBS. Cells were maintained in a humidified incubator at 37° C. in the presence of 5% $CO_2$.

Device fabrication and assembly. Silicon microsieves were fabricated as described (Lim et al.). Briefly, the microsieve consists of a silicon disk having an overall diameter (ø) of 7.3 mm and a support ring of thickness 300 µm. The central capture region has φ 5.3 mm and 60 µm thickness containing 100,000 circular pores obtained by deep reactive ion etching. To embed the microsieve in a sterile 3-ml syringe, an acrylic sleeve insert was designed, consisting of an inlet channel of ø 8.58 mm tapered to a ø 5.54 mm channel, which corresponded to the microsieve cell capture region. The sleeve insert housed the microsieve and silicone O-rings (0.5 mm thick) that ensured good sealing and cushioning as shown in FIG. 1C. The retrieval device was assembled as follows. Firstly, the rubber plug of a 3 ml syringe plunger was removed and a hole of 5.5 mm diameter was created using a punch cutter. The perforated rubber plug was placed in the 3-ml syringe. Next, an O-ring was placed in the slot of sleeve insert, followed by the microsieve and another O-ring. Finally the sleeve insert with the microsieve and O-rings was placed in the 3-ml syringe above the perforated rubber plug. This arrangement enabled the microfiltration of cells by size from whole blood and the subsequent retrieval of captured cells from the upper surface of microsieve in a convenient set-up.

Microfiltration. To optimize blood microfiltration, 5 µM CellTracker (Life Technologies) labelled cells were added to donor blood at 10-50 cells per ml of whole blood. Blood was filtered at various flow rates by means of a peristaltic pump (Ismatec). After 6 washes using PBS, 0.5% BSA and 2 mM EDTA, cells were resuspended in culture medium. Subsequently, cell nuclei were stained using Hoechst 33342 (Life Technologies), and cells were retrieved to determine retrieval efficiency and fold depletion of contaminating WBCs. In some experiments, CellTracker positive cells remaining on the microsieve were also counted.

Percent retrieval efficiency was calculated as follows:

% Retrieval Efficiency=(Retrieved cells)×100/(Spiked Cells)

Fold depletion was calculated as follows:

Fold Depletion of WBCs or RBCs=(WBCs or RBCs in Whole Blood)/(WBCs or RBCs in Microfiltrate)

WBC count in microfiltrate is defined as the number of any Hoechst 33342 positive, CellTracker negative event in the case of experimental enrichment or by any CD45 positive event in the case of clinical sample analysis. All clinical samples were immediately processed for the indicated downstream applications using optimized parameters described in the description of FIG. 3B, i.e. imaging, counting, single-cell isolation and analysis, cell culture or pooled nucleic acid extraction. To estimate ideal target WBC depletion, micromanipulation on serial dilution of PBMCs containing 50 CellTracker positive HCT 116 cells was performed. Five thousand fold depletion allowed micromanipulation of pure HCT 116 cells without contaminant white blood cells. The ideal target retrieval efficiency was chosen based on literature search on existing label-free CTC isolation devices (Cima et al.). Microfiltration of clinical samples was performed using 2 ml whole blood for each device and optimized microfiltration conditions.

An optimal tradeoff between retrieval efficiency and cell purity was obtained using a flow rate of 0.25 ml min$^{-1}$ and pore diameters of 9-10 µm. This resulted in >90% SW620 retrieval efficiency with >5×10$^3$ fold depletion of white blood cells (FIG. 3D), allowing for a variety of downstream applications beyond cell counting.

Example 3—Analysis and Characterization of the Captured and Retrieved TECCs

This example describes a method for identification and analysis of a well-defined population of endothelial cells (cells originating from the blood vessel) that can be isolated from blood and can be used as biomarker for:
1) Diagnosis of tumors at all stages, even at very early stages of the disease
2) Monitoring response to therapy of tumors
3) Predicting response to therapy of tumors
4) Predicting blood vessel features of the tumor The method may be used on its own, or can be combined with standard diagnostic/prognostic methods to increase the accuracy of the diagnostic/prognostic test(s). For example, this method can be combined with CEA measurement (a biomarker of colorectal cancer that is measured in blood) to facilitate diagnosis of colorectal tumors.

On-sieve immunofluorescence. Suspension cells were stained for 30 min directly 'on sieve' after 5 washes in PBS containing 0.5% BSA, 2 mM EDTA and human FcR Blocking Reagent (Miltenyi Biotec) using the following fluorescent-labelled antibodies: anti-CD45 1:200 (clone 2D1; eBioscience), anti-Ep-CAM 1:20 (9C4, BioLegend), anti-CD31 1:20 (WM59, BioLegend), anti-CD144 1:10 (55-7E11, BD), anti-CD41 1:20 (HIP8, BioLegend) anti-CD42B 1:20 (HIP1, BioLegend). For intracellular antigens, the Inside Stain kit (Miltenyi Biotec) and human FcR Blocking Reagent were used with the following antibodies: anti-VWF 1:200 (rabbit polyclonal A 0082, DAKO, conjugated in-house to Alexa 488 or Alexa 555 using Life Technologies APEX Antibody Labeling Kit), anti-Vimentin (V9, Santa Cruz Biotechnology), anti-pan Cytokeratin (C11, Cell Signaling Technology). Nuclei were stained using Hoechst 33342 (Life Technologies). In some experiments, Calcein AM (Life Technologies) was used to identify living cells. After a washing step, cells were retrieved and visualized in suspension under an inverted fluorescence microscope (1×81, Olympus) for imaging, counting and/or micromanipulation. Images were recorded using the MetaMorph software (Molecular Devices) with a CoolSNAP HQ2 CCD Camera (Photometrics).

Figure 8:
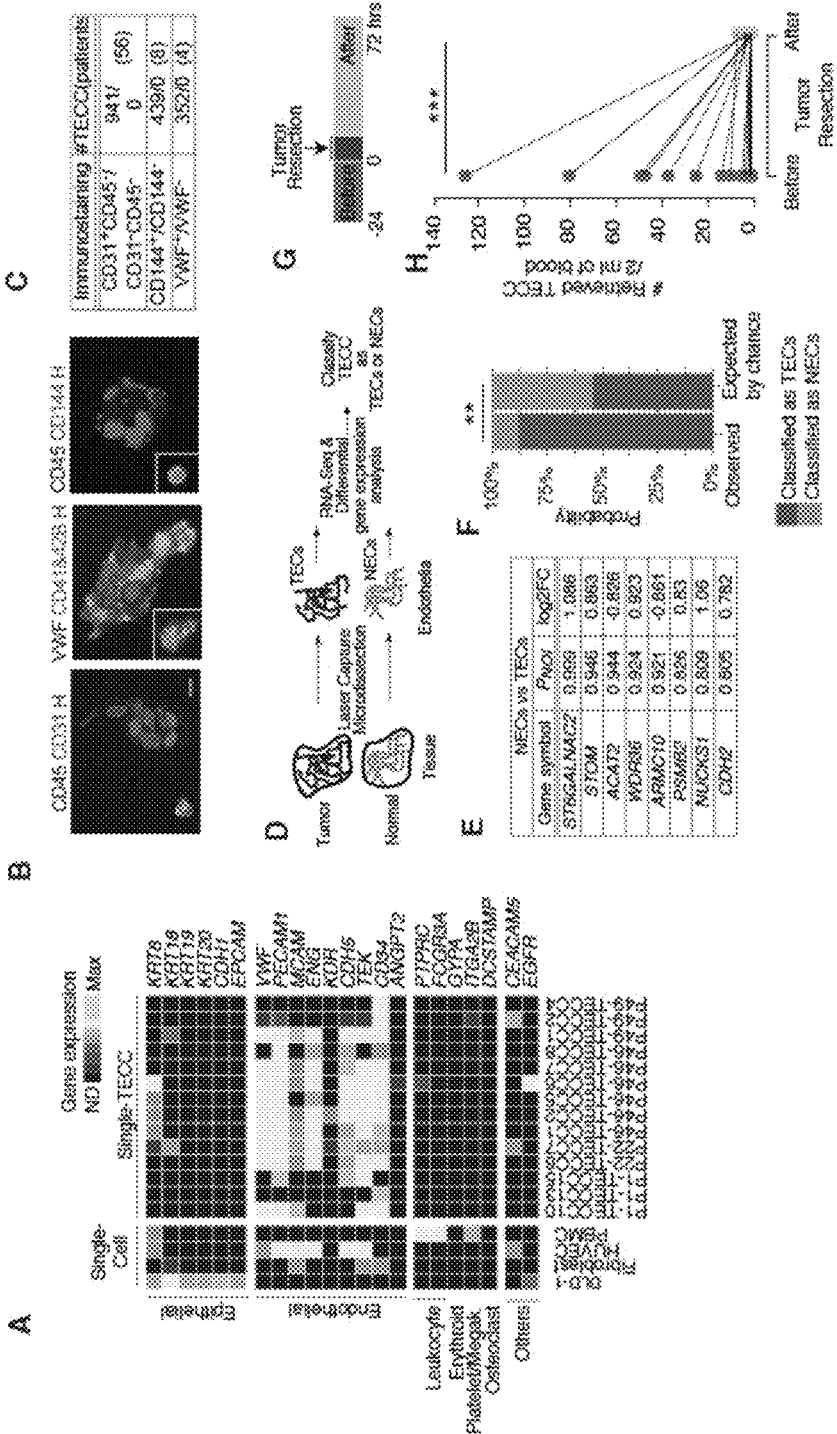
FIG. 8 shows characterization of TECCs. (A) shows scrm-PCR gene expression in control single cells and 14 TECCs (N=4 patients) indicate the presence of endothelial cell markers but the absence of epithelial cell markers or markers for white blood cells (leukocyte), red blood cells (Erythroid), platelets/megakaryocytes or osteoclasts. (B) shows results from immunofluorescence studies which confirm endothelial lineage of TECCs. Representative TECCs stained with the antibodies indicated and internal controls for each staining. Inset central panel, a CD41&CD42B⁺ platelet aggregate. Inset right panel, a CD45⁺ white blood cell. (C) Table indicates TECCs counts positive or negative for the indicated immunofluorescence (N=68 patients). (D) Experimental procedure used to classify TECCs as normal endothelial cells (NECs) and tumor endothelial cells (TECs). (E) Genes differentially expressed between NECs and TECs. $P_{NOI}$ probability of differential expression as computed by NOISe. Log₂FC, log₂(fold change). (F) Column chart stacked to 100% indicating classification of TECCs as TECs (red columns) and NECs (blue columns). Left column indicates the observed probabilities; right column indicates the mean probabilities obtained by 1000 random signatures. P=0.003, effect size r=0.46, exact binomial test. This experiment indicate that TECCs are indeed tumor-derived (G) Longitudinal sample collection strategy before and after surgery. (H) Ladder plot showing CD31⁺CD45⁻ TECCs counts 0-24 h before and 24-72 h after surgery. Lines connect data from the same patient. *P=0.0006, effect size r=0.54. This experiment support the hypothesis that TECCs are tumor-derived because they disappear shortly after tumor resection.

TECC definition and count. A population of tumor-derived endothelial cells in the blood of colorectal cancer patients was detected using the methods described herein. These cells form clusters of multiple cells deriving from the tumor vasculature (blood vessels of the tumor) (FIG. 8), and hence were identified as tumor-derived endothelial cell clusters (TECCs). TECC is defined as follows: "any cell or cellular cluster isolated from blood with a major axis of >10 µm, having at least 2 clearly distinct nuclei and expressing CD31, VWF or CD144 proteins but not expressing CD45, CD41 and CD42B" (FIG. 8B). Importantly, the cellular populations belonging to the megakaryocytic lineages, having large and lobulated single nuclei or large and round single nuclei, were excluded. These cells had characteristic cytomorphology easily discernible from TECC, stained positive for CD41 and CD42B, and were predominantly observed in colorectal cancer patients undergoing treatment, but also in some healthy volunteers and treatment-naive colorectal cancer patients. Single endothelial cells, owing to their smaller diameter that would allow them to pass through the microsieve, were also excluded from the analysis. TECCs were counted by applying these inclusion and exclusion criteria by adding the microfiltrate obtained from 2 ml of whole blood to a well of a 96-well plate. After a short centrifugation step, TECCs were identified and counted by manually scanning the target well three times using a 20× objective. A positive sample was defined by the detection of at least one TECC.

Figure 13:
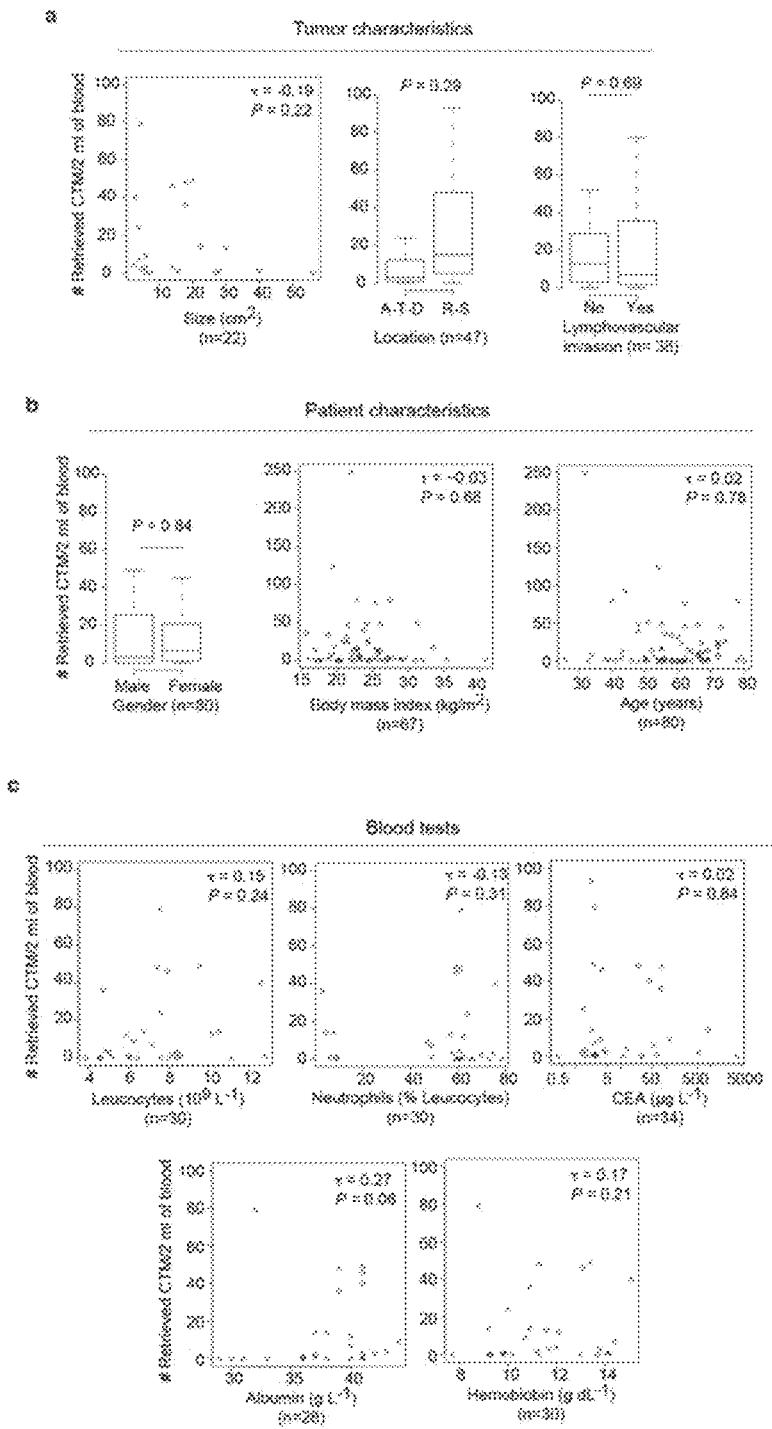
FIG. 13 shows that TECC counts do not correlate with inflammatory markers or other variables. (a-c) show the association of TECC number with the indicated tumor characteristics, patient's characteristics, and blood test values respectively. Correlations are shown as dot plots and measured using the Kendall's τ coefficient and its derived P value. Comparisons of dichotomized variables are shown as boxplots and differences are quantified using P values from two-tailed exact Wilcoxon-Mann-Whitney U tests.

As shown in FIG. 13, TECC counts do not correlate with inflammatory markers or other variables. This indicates that TECCs are not directly related to inflammatory events or other variables that are unrelated to tumor. This thus supports that TECCs are tumor-derived.

Determine if TECCs are Tumor-Derived

Figure 9:
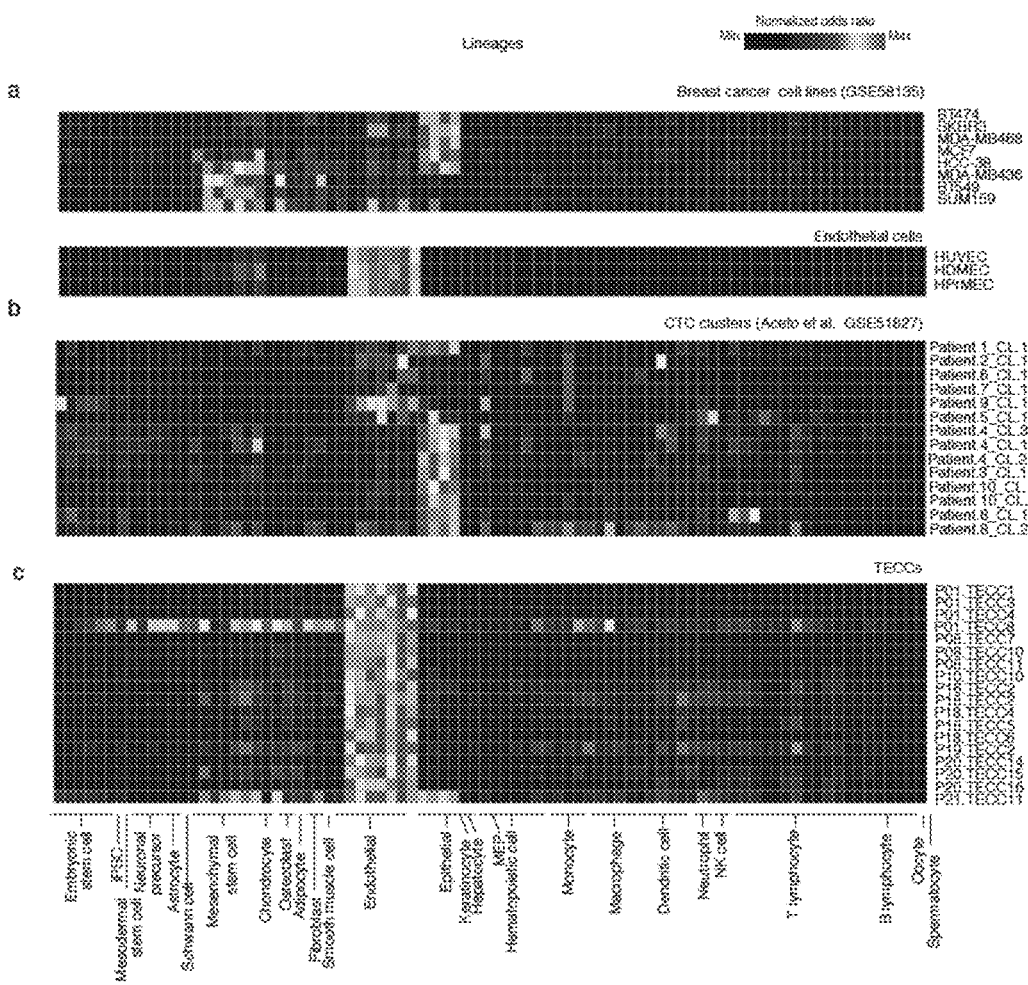
FIG. 9 shows lineage mapping of TECCs and CTC clusters (Aceto et al.). (a) shows selected breast cancer cell lines with epithelial and mesenchymal lineage profiles and primary endothelial cells were used as positive controls for epithelial, mesenchymal stem cells and endothelial lineages. Lineages were mapped using the method described in Cima I et al. (b) shows lineage inference of CTC clusters reported in Aceto et al. which shows the presence of epithelial-derived cell clusters. (c) shows lineage inference of single TECCs analyzed in this study indicate that TECCs are endothelial cells and are thus different from CTC clusters.
Figure 10:
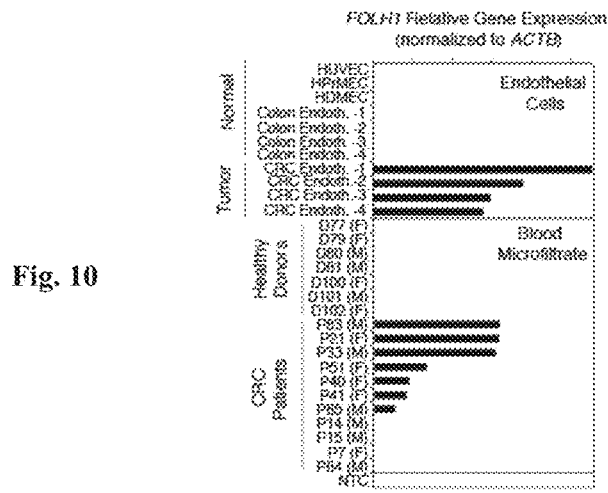
FIG. 10 shows amplification and analysis of PSMA gene using scrmPCR. PSMA (FOLH1) gene expression is shown for the indicated samples of normal and tumor endothelial cells, and for the blood microfiltrates for the indicated healthy donors (D) or CRC patients (P). F, female; M, male.
Figure 11:
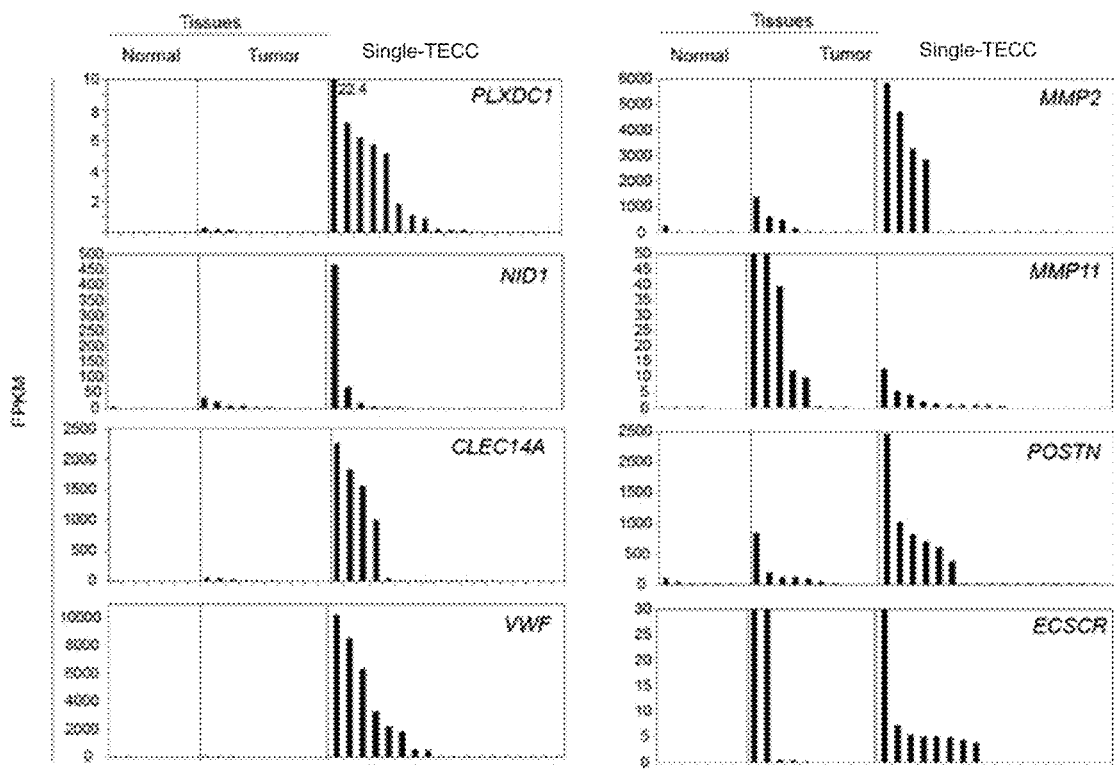
FIG. 11 shows tumor endothelial markers expressed in TECCs. Additional tumor endothelial markers were expressed in normal, tumour tissues and TECCs, detected from RNA-Seq data. PLXDC1, plexin domain containing 1 (tumor endothelial marker 3/7); MMP2, matrix metallopeptidase 2; NID1, nidogen 1; MMP11, matrix metallopeptidase 11; CLEC14A, C-type lectin domain family 14, member A; POSTN, periostin; VWF, von Willebrand factor; ECSCR, endothelial cell surface expressed chemotaxis and apoptosis regulator.

To test if TECCs were tumor-derived, paired samples from 17 colorectal cancer patients 0-24 h before and 24-72 h were collected after surgical tumor resection (n=34). Tumor removal caused a sharp decline of endothelial TECCs, supporting the direct link between the tumor and TECCs (FIG. 8H and Supplementary Table 5). Folate hydrolase (FOLH1), the gene encoding for prostate-specific membrane antigen (PSMA), is specifically expressed in tumor vasculature of various cancer types, but absent in normal vasculature and peripheral blood. FOLH1 was indeed expressed in $CD31^+CD45^-$ cells isolated from fresh colorectal cancer tissues and in TECCs isolated from the blood of 7/10 colorectal cancer patients, but not in endothelial cells isolated from normal tissues or in healthy donor peripheral blood mononuclear cells (PBMCs) (FIG. 9). This result further supported the tumor origin of endothelial TECCs (FIG. 8). Additionally, RNA-Seq data of TECCs revealed the expression of several tumor endothelial markers (FIG. 11). It was further asked whether TECC numbers might correlate with features of the underlying tumor vasculature, by counting blood vessels in tumor tissues derived from patients with low or high TECC count. Although the median number of vessel units did not differ, the median number of lumens was significantly higher in patients with high TECC counts. Taken together, it was shown that TECCs in colorectal cancer patients were not malignant entities but clusters of tumor-derived mature endothelial cells.

Figure 12:
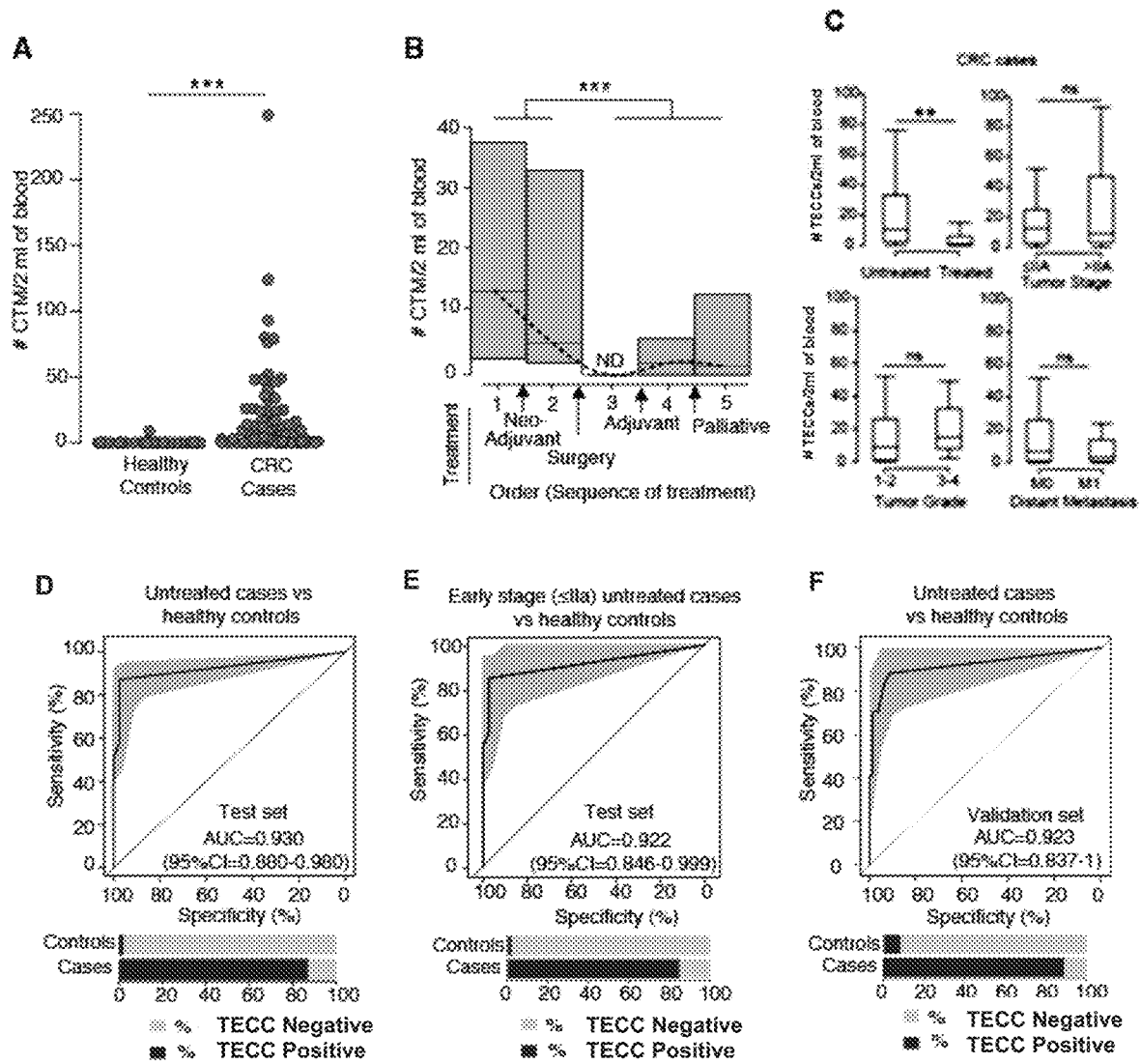
FIG. 12 shows that TECCs are detected in colorectal cancer (CRC) patients but not in healthy individuals. (A) shows TECCS count for healthy controls (median=0, N=45) and CRC patients (median=4.5, N=80). *$P=7.31\times10^{-15}$, effect size $r=0.65$. (B) Trend of TECCs count during sequence of treatment for colorectal cancer. Blood samples were collected independently at the following discrete time points: 1) treatment-naïve, 2) post neoadjuvant therapy, 3) post surgery, 4) post adjuvant therapy, and 5) palliative therapy. Boxes indicate the interquartile range (IQR), line across boxes indicates the median, dashed line indicates spline interpolation of medians. Arrows indicate treatment events. N=80 CRC cases, *$P=0.0002$, effect size $r=0.41$, ND, not detected. (C) shows association of TECC count with patients and tumour characteristics (n=80 CRC cases). Two-tailed Wilcoxon-Mann-Whitney U test with Bonferroni correction, **$P=0.0072$, effect size $r=0.34$, $\hat{\Delta}$ (95% CI)=$-6$ ($-13-(-1)$). (D) ROC curve comparing treatment-naive CRC patients with healthy controls (total N=89). Grey area represents the bootstrapped 95% CI. AUC (95% CI)=0.930 (0.880-0.980), effect size $r=0.716$. (E) ROC curve comparing treatment-naive, early-stage CRC patients (≤IIA) versus healthy controls. AUC (95% CI)=0.922 (0.846–0.999), effect size $r=0.706$, (total N=61). (F) Validation set. ROC curve comparing treatment-naive CRC patients with healthy controls (total N=100). AUC (95% CI)=0.923 (0.837–1), effect size $r=0.706$. In (D) to (F), 100% stacked bar charts indicate the percentage of TECCs-positive (dark grey) and TECCs-negative (light grey) samples for both healthy controls and CRC cases.

Because of the above-described associations between TECC and the primary tumor, it was next asked if endothelial TECCs were informative indicators of colorectal cancer. Endothelial TECCs from a total of 141 clinical specimens from 125 subjects (45 control healthy volunteers and a consecutive series of 80 colorectal cancer patients, including TECC counts from above-mentioned patients) were counted. At least one endothelial TECC in 76.2% (61/80) of colorectal cancer patients but only in 2.2% (1/45) of healthy individuals was observed (FIG. 12A). It was found that treatment-naive patients presented with significantly higher endothelial TECC counts as compared to patients that underwent therapeutic interventions for colorectal cancer (FIG. 12C). However, endothelial TECC count did not associate with clinical parameters such as tumor stage, grade or presence of distant metastasis (Supplementary Tables 6 and 7) or with other variables, including inflammatory markers. In particular, endothelial TECC numbers in time series analysis indicated that surgical resection events has the strongest effect on TECC distribution, confirming the results in FIG. 8H and further supporting the association of endothelial TECC with the presence of a primary tumor (FIG. 12B). The presence of endothelial TECC in 86.5% of treatment-naive patients (45/52), but only of 2.2% of healthy controls (1/45) indicated that TECC count might be useful in assisting colorectal cancer diagnosis. Area under the curve (AUC) of the receiving operator characteristic (ROC) curve comparing treatment-naive patients and healthy controls was 0.930 (FIG. 12D), and the AUC of ROC curve comparing treatment-naive, early-stage CRC patients and healthy controls was 0.923 (FIG. 12F). Remarkably, colorectal cancer patients with low pathologic tumor stage (stage≤IIA) were also positive for endothelial TECC in 86.4% (19/22) of cases, with AUC=0.922 (FIG. 12E). Taken together, these results further confirmed the association between endothelial TECC counts and presence of a primary tumor. Moreover, widespread presence of endothelial TECCs in treatment-naive patients but not in healthy individuals indicated the potential use of endothelial TECC count as a diagnostic adjunct for colorectal cancer.

Target cell identification, micromanipulation and storage. Target cells were manually micropipetted using a mouth pipette attached to a 25-ml syringe. Briefly, cells were identified from total cell retrieval by means of bright field image, nuclear staining and specific fluorescent signals. Target single-cells or TECCs were then micropipetted in a 10-µl droplet of wash buffer, followed by deposition in 0.2-ml PCR tubes containing appropriate buffer: 5 µl of 2× Reaction buffer (CellsDirect One-Step qRT-PCR Kit, Life Technologies) for scrmPCR, 2 µl of PBS for whole genome amplification or 2 µl of SuperBlock buffer (Thermo Scientific) for low-input RNA-Seq. Cells were stored immediately at −80° C. until use. In some cases, the complete microfiltrate was spun down, and stored at −80° C. until further use.

Single-Cell RNA and Mutational Analysis PCR (scrm-PCR).

Figure 5:
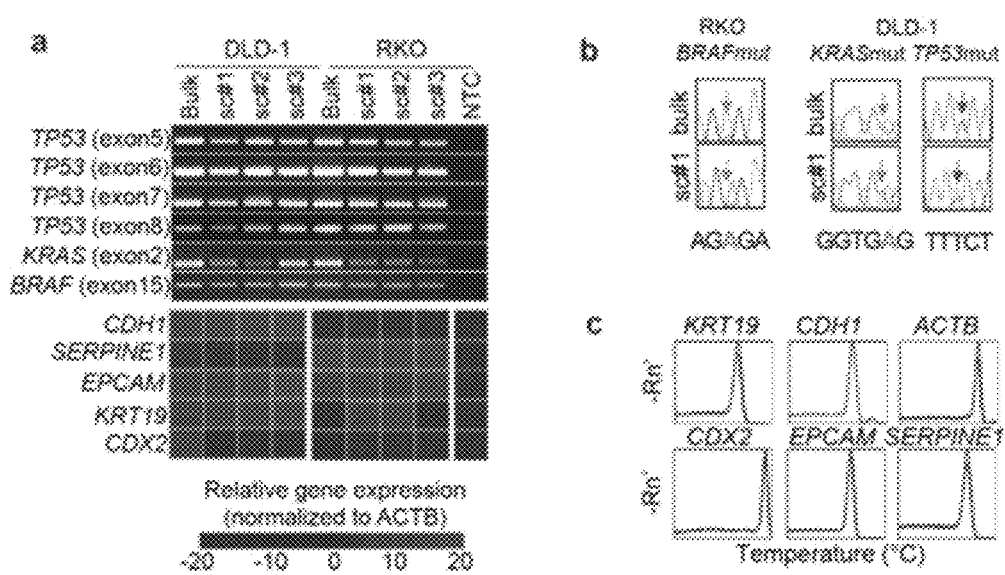
FIG. 5 provides the proof of principle for the scrmPCR method described herein. Single DLD-1 and RKO cells (colorectal cancer cell lines) were micro-manipulated in 5 μl 2× Reaction Buffer (CellDirect kit). scrmPCR was then performed as described herein, with the results shown in (a). Genomic regions belonging to TP53, KRAS and BRAF genes were amplified. PCR products were subjected to Sanger sequencing and known hotspot mutations that have been previously characterized in both cell lines were detected as shown in (b). At the same time several transcripts from the same cells were amplified and shown to have variable gene expression in both cell lines. Gene expression specificity was verified by the melting curve peak temperature and by the presence of a single peak, as shown in (c).

To confirm the presence of DNA mutations in single-cells undergoing EMT, a PCR protocol was established for the simultaneous quantitation of RNA transcripts and detection of DNA mutations at the single-cell scale (Single-cell RNA and Mutational Analysis PCR or 'scrmPCR') (FIG. 5. Supplementary Table 1).

Primers were designed using Primer-BLAST (Ye et al.). For each RNA transcript, primers were designed either spanning exon-exon boundaries or primers separated by at least one intron on the corresponding genomic DNA region. Primers for mutational analysis were designed to bind intronic regions of the target gene (Supplementary Table 1). The scrmPCR could be used to simultaneously detect and quantify RNA transcripts and sequence DNA hotspots in the same cell. Briefly, single-cell RNA transcripts were reverse transcribed at 50° C. for 30 min using SuperScript III Reverse Transcriptase (Invitrogen) and a mix of 500 nM target reverse primers. A preamplification round was then performed using Platinum Taq DNA polymerase (Invitrogen) by adding a matching mix of forward primers to the transcript-specific reverse primers and primers pairs for targeted genomic regions. Preamplification cycling was conducted by alternating annealing and denaturation steps without extension as follows: 6× cycles at 60° C., 4 min, 95° C., 1 min; 6× cycles at 55° C., 4 min, 95° C., 1 min; 6× cycles at 50° C., 4 min, 95° C., 1 min. Primers cleanup was performed using the Axyprep PCR Clean-up Kit (Axygen). Samples were diluted 1/20 and stored at −20° C. until further use. For RNA transcript quantitation, quantitative PCR was performed on a ViiA7 Instrument (Applied Biosystems) using 2 µl of preamplification reaction, seminested primer pairs according to the target transcript (Supplementary Table 1) and the SensiFAST SYBR Lo-ROX Kit (Bioline) following manufacturer's protocol. Relative gene expression was normalized using ACTB as reference gene. To analyze selected DNA mutational hotspots, PCR was performed by using 2 µl of preamplification reaction, nested PCR primer pairs (Supplementary Table 1) and a master mix containing a proof-reading polymerase (KOD Hot Start Master Mix, EMD Millipore) following manufacturer's instructions. For KRAS exon 2 sequencing in tumor and normal tissue (FIG. 6d), PCR amplification was performed using the following forward primer, TTTGTATTAAAAGGTACTGGTGGAG and reverse primer, CCTTTATCTGTAT CAAAGAATGGTC. PCR products were separated on agarose gel; specific bands were excised and sequenced using the Sanger method.

Figure 6:
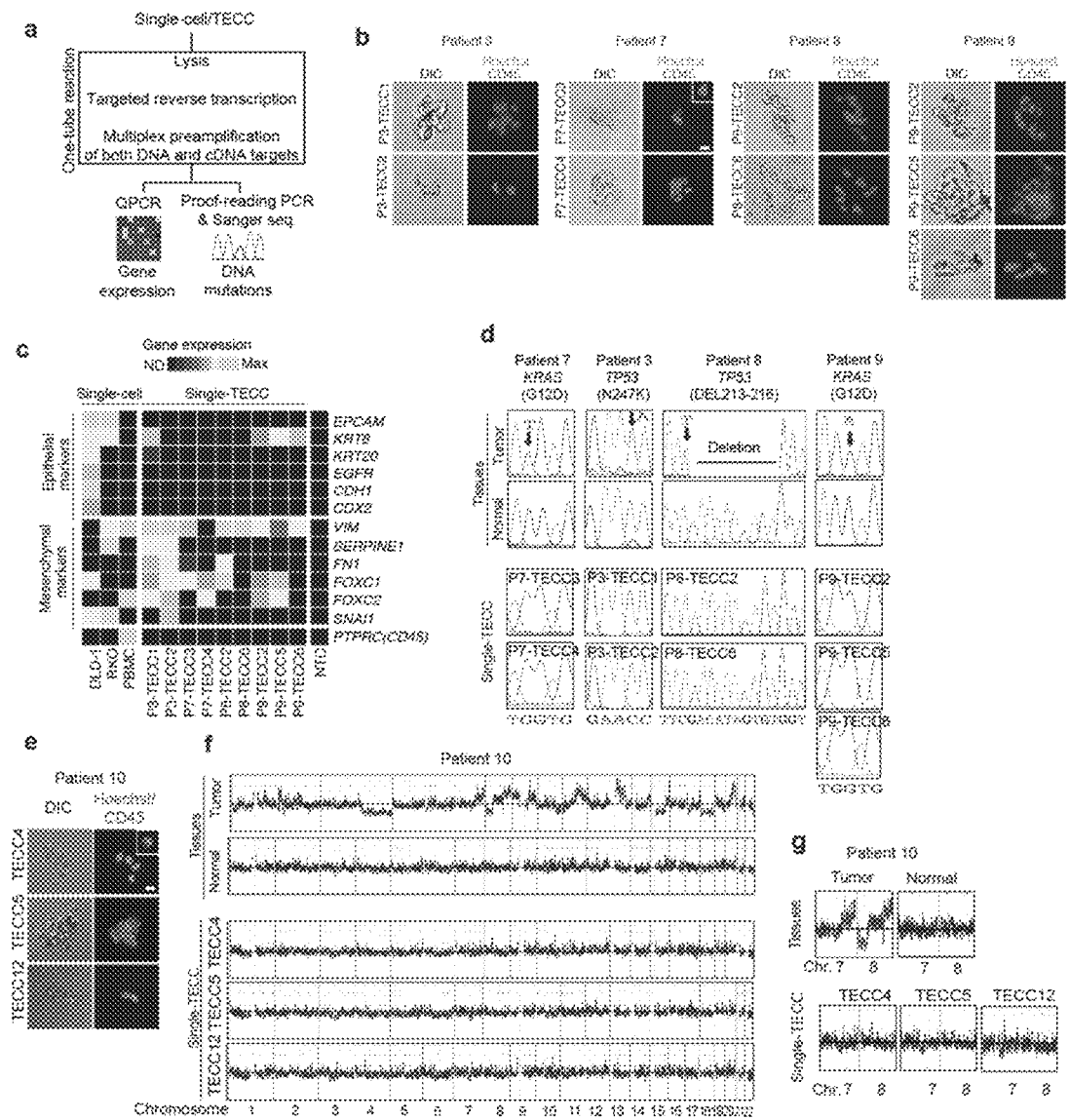
FIG. 6 shows that TECCs express epithelial-mesenchymal transition (EMT) markers, but do not mirror primary tumor mutations or chromosome abnormalities, thus indicating that TECCs and CTCs are different entities. (a) shows an exemplary scrmPCR workflow as described herein for single-cells or single-TECC. (b) shows images of nine TECCs from 4 colorectal cancer patients with known primary tumor mutations micro-manipulated in single tubes for downstream scrmPCR. (c) shows the gene expression heat map of TECCs shown in (b), and control single-cells for the indicated epithelial and mesenchymal markers and PTPRC (CD45). Colours represent gene expression from absent (black) to maximum (light grey). NTC—no template control. (d) shows chromatograms of hotspot gene sequences derived from the same single-TECC shown in (b) and (c). Matching primary tumor and normal colon tissues (top panels) were used to compare gene mutations. Note that in TECCs no such mutations were found, indicating that TECCs do not originate from the tumor epithelium, as such TECCs are different from previously described malignant CTC clusters. (e) TECC array comparative genomic hybridization (aCGH) shows images of three TECCs from a representative colorectal cancer patient with known chromosomal abnormality. (f) shows aCGH analysis of TECCs shown in (e) with matching normal and tumor tissues. (g) shows the analysis for chromosomes 7 and 8 for the indicated tissues and TECCs. The lines indicate smoothed data calculated using Affymetrix ChAS software.
Figure 7:
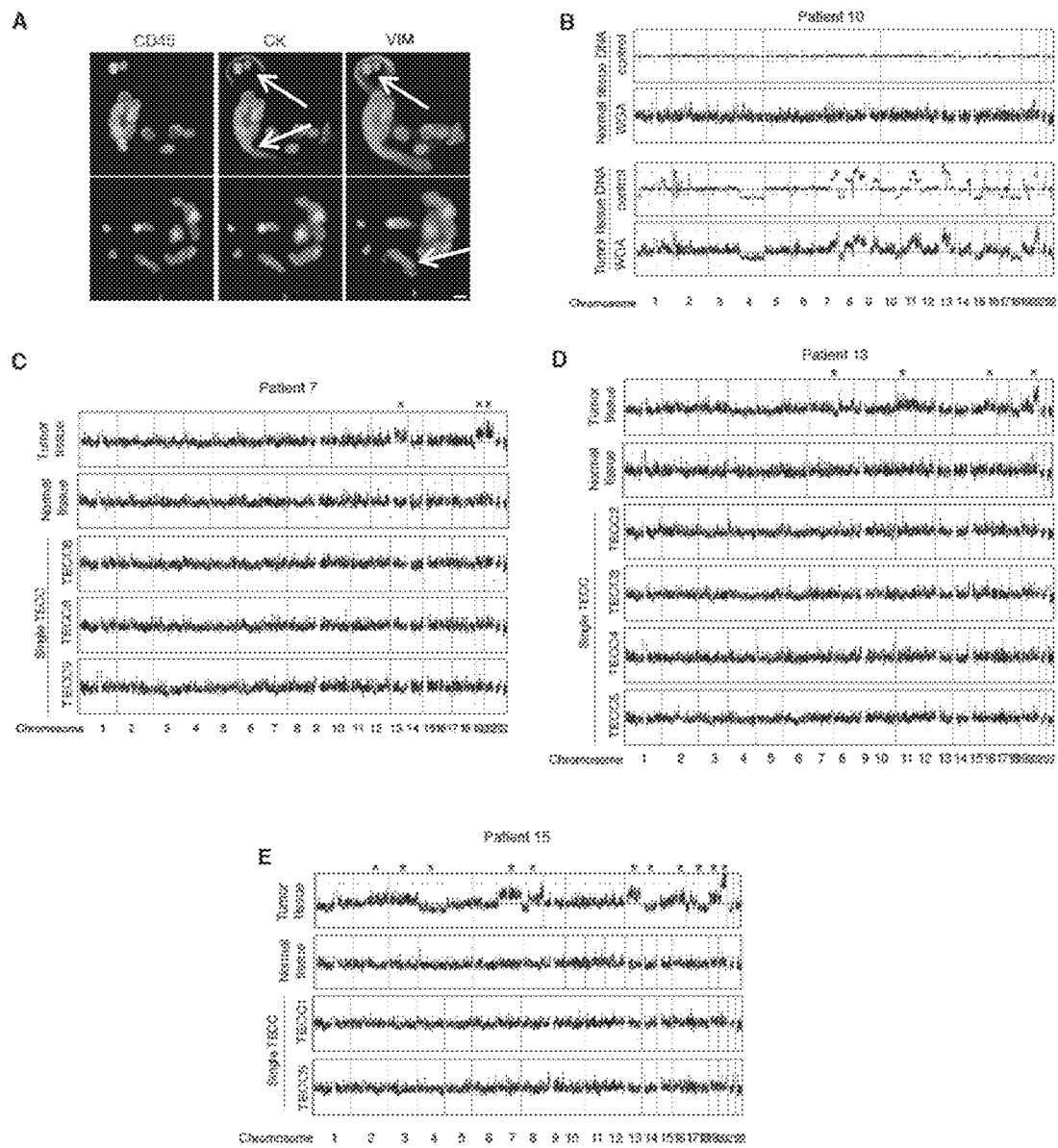
FIG. 7 shows that TECCs express EMT markers but have normal chromosomal structures. (A) shows representative 4-colour immunofluorescence of two TECCs for CD45, Vimentin (VIM), pan-Keratin (CK) and DAPI, indicating heterogeneous mesenchymal and epithelial markers expression (the points of the arrows indicate visible stainings). (B) shows a control experiment to assess the impact of whole genome amplification (WGA) for aCGH experiments using single-cells. (C-E) each shows aCGH of single-TECC for the indicated patients similar to normal tissue DNA shown in (B). As shown in (c-e), in TECCs, no chromosomal abnormalities could be found, indicating that TECCs do not originate from the tumor epithelium. As such, TECCs are different from previously described malignant CTC clusters.

FIG. 6a provides an exemplary scrmPCR workflow for TECC. TECC samples were analyzed using the scrmPCR method according to the workflow. scrmPCR in 9 TECCs derived from 4 patients revealed the presence of epithelial and mesenchymal markers including SERPINE1, FOXC1 and KRT8, in line with epithelial-mesenchymal profiles reported previously for breast cancer CTCs (FIGS. 6b and 6c). These results were confirmed by panCK and Vimentin immunostaining (FIG. 7a). These TECCs were next sequenced for mutations present in the corresponding primary tumors. Surprisingly, all tested DNA sequences hotspots matched the wild-type alleles (FIG. 6d). Targeted high-throughput DNA sequencing was further applied to 8 commonly mutated genes in DNA amplified from 16 single-TECC (6 patients) and matching tumor tissues. Again, matching mutations between tumor tissues and associated TECCs (Supplementary Tables 2 and 3) could not be detected. Using amplified DNA from 12 TECCs (4 patients), array comparative genomic hybridization (aCGH) was next performed. In fact, CTCs from lung cancer patients have been shown to reproducibly mirror cancer tissue copy number variations. Here, the TECCs had instead normal cytogenetic profiles in contrast to matched primary tumors (FIG. 6e-g). In summary, single-cell scale analysis of 26 TECCs from 10 patients, while displaying epithelial-mesenchymal marker expression, did not mirror DNA anomalies found in matching tumor tissues. This suggested a source for TECC that was unrelated to the tumor epithelium.

Nucleic Acid Extraction. Complete microfiltrates or isolated cells were subjected to RNA extraction using the RNAqueous-Micro Total RNA Isolation Kit (Ambion) following manufacturer's instructions. Total RNA from tissues was isolated using the RNeasy mini kit (Qiagen). DNA from tissues was isolated using DNeasy mini kit (Qiagen).

TECC targeted resequencing and array comparative genomic hybridization (aCGH). Single-TECC was subjected to whole genome amplification using the GenomePlex Single-cell Whole Genome Amplification Kit (Sigma) and following manufacturer's instructions. Tissue DNA (50 pg) samples were amplified using the same procedure. For targeted resequencing, a custom gene panel targeting exons for NRAS, CTNNB1, PIK3CA, EGFR, BRAF, PTEN, KRAS, AKT1 and TP53 genes (~6.1 kb) was designed. The libraries were constructed using Ion AmpliSeq Library Kits 2.0 (Life Technologies) with 10 ng of input DNA. Targeted resequencing run was performed on Ion Torrent Personal Genome Machine (PGM) Sequencer (Life Technologies). Variants were called using Ion Torrent Variant Caller Plugin in high stringency settings. aCGH was performed by hybridizing 250 ng of DNA to CytoScan 750 K arrays (Affymetrix) with manufacturer's instructions and reagents. Data were analyzed and visualized using Chas software version 2.1 (Affymetrix). FIG. 6f shows results of the aCGH analysis. The lines indicate smoothed data calculated using Affymetrix ChAS software. Asterisks indicate large chromosomal abnormalities detected in the tumor sample. Note that in TECCs, no chromosomal abnormalities could be found, indicating that TECCs do not originate from the tumor epithelium. As such TECCs are different from previously described malignant CTC clusters.

TECC and Tissues cDNA Synthesis and RNA-Seq.

18 single-TECC from 8 patients and matching normal colon and tumor tissues were subjected to RNA expression profiling by high-throughput sequencing (RNA-Seq) (FIG. 9c, Supplementary Table 4). cDNA was synthesised from single-TECC and 10 pg of tissue RNA with the SMARTer Ultra Low RNA kit (Clontech Laboratories) using long distance PCR (LDPCR) with 25 cycles and 18 cycles respectively. For each sample, cDNA was sheared using the Adaptive Focused Acoustics system (Covaris). Libraries were constructed using NEBNext DNA Library Prep Master Mix kit (New England Biolabs). All libraries were barcoded using unique indexes and pooled for RNA sequencing run on the Illumina HiSeq 2000 platform. Data were mapped to Human Genome version 19 (hg19) using Tophat (version 2) (Trapnell et al., 2009). Cufflinks (version 2.2) (Trapnell, C. et al., 2010) was used to quantify gene expression as FPKM (Fragments Per Kilobase of transcript per Million mapped reads).

Figure 14:
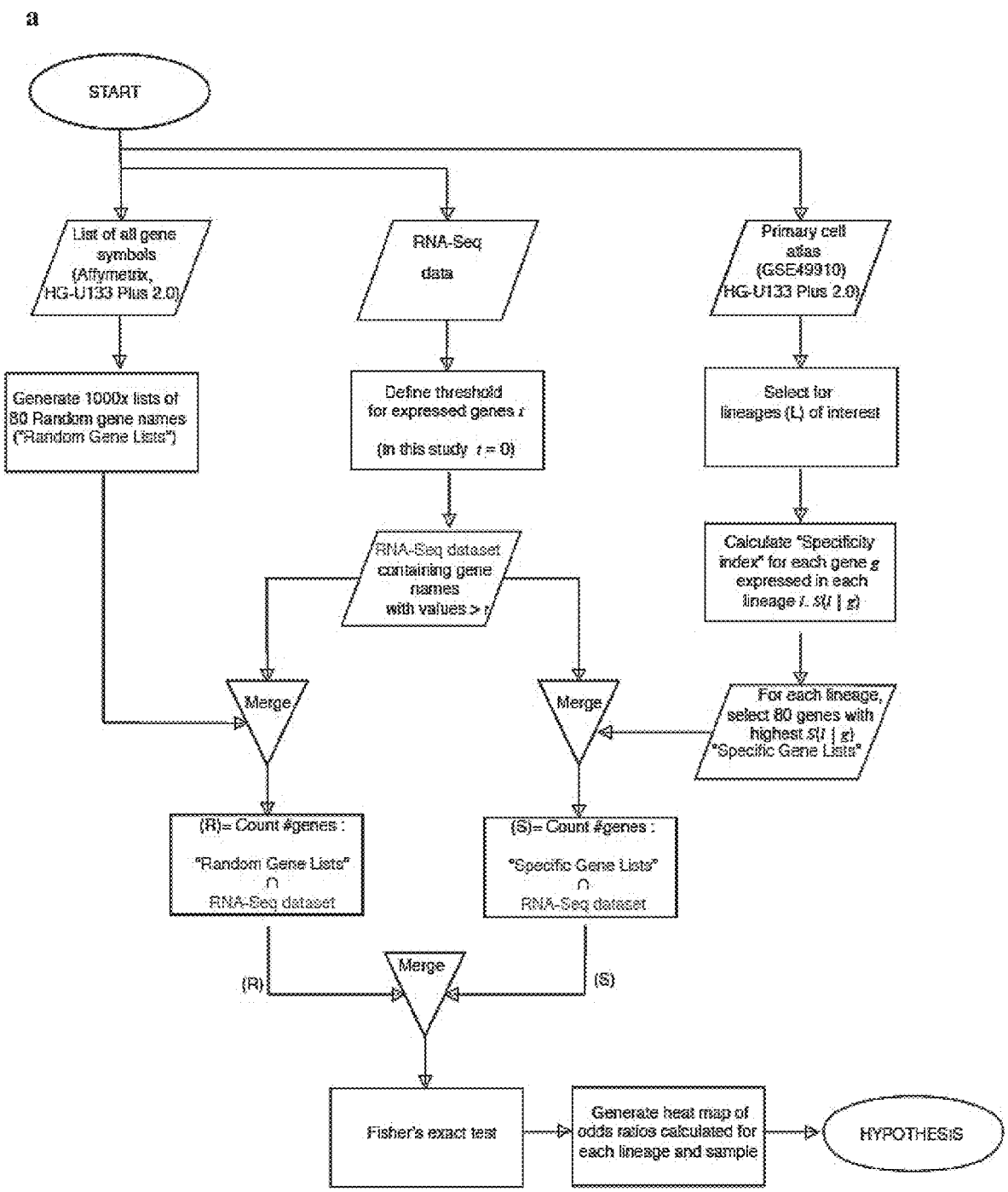
FIG. 14 shows a lineage inference workflow used to generate the data shown in FIG. 9.
Figure 14:
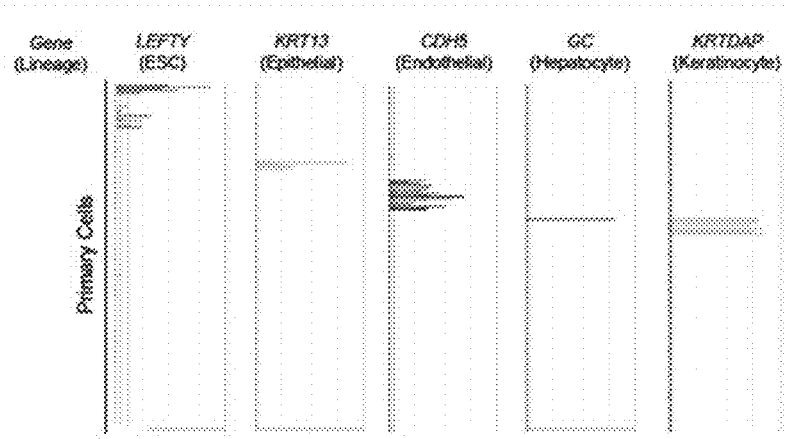
Figure 14:
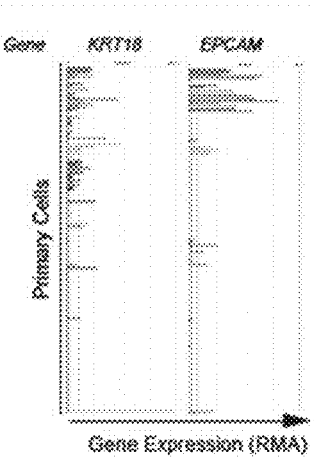
Figure 14:
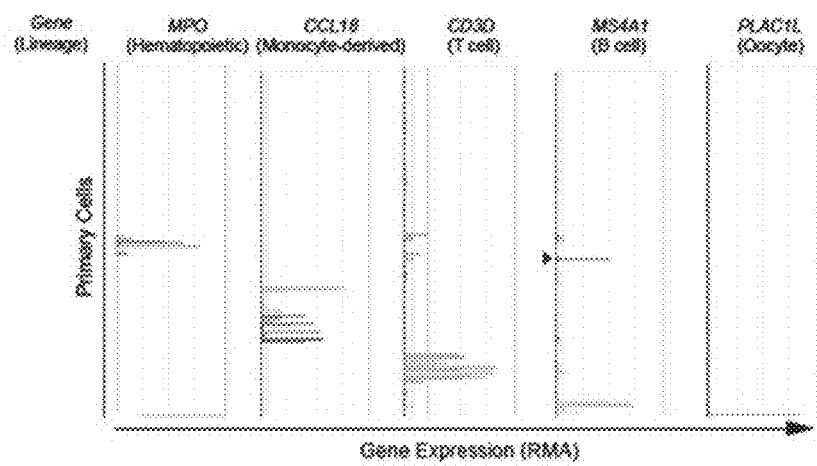
Figure 15:
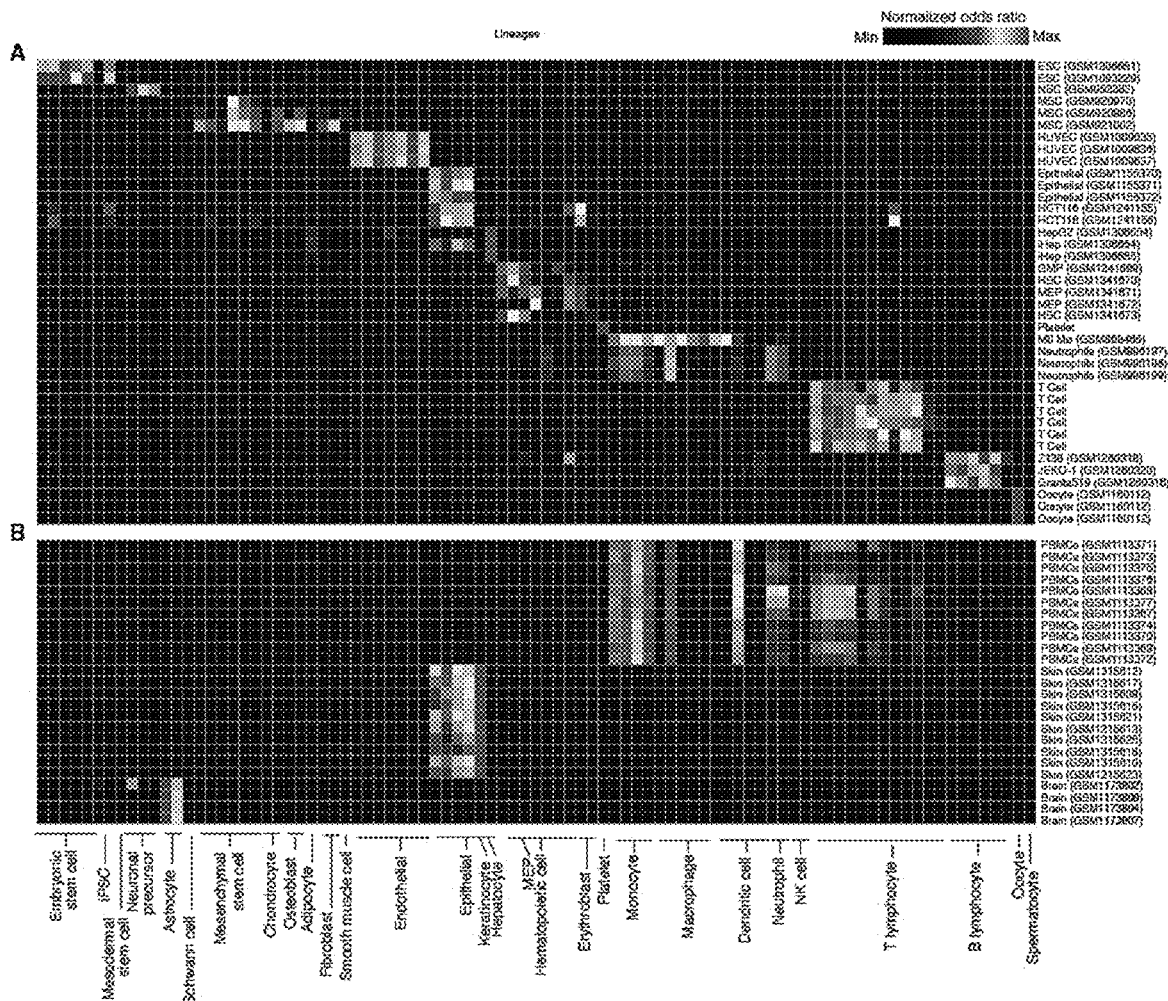
FIG. 15 shows a lineage inference algorithm validation. (A) shows heat maps comparing number of genes enriched for each sample (rows) and lineage (columns) over random enrichment. Samples are published RNA-Seq data from selected lineages. Each coloured box represents a normalized odds ratio of the respective Fisher's exact test from 0 (black) to 1 (light grey). (B) Same as in (A), except that whole tissues or complex cell mixtures such as PBMCs, skin and brain datasets were used.

A workflow for the inference of cellular lineages from transcriptional profiles was further developed (FIGS. 14 and 15). In a comparison including 42 different cell types (FIGS. 9a to 9c), all TECC transcriptomes were associated with the cell types of the endothelial lineage (FIG. 9c). The presence of a series of endothelial lineage markers together with general EMT markers by scrmPCR was confirmed in an additional 14 TECCs (FIG. 8). Endothelial cells are considered a specialized epithelium, and are known to express both Vimentin (often used as a mesenchymal marker) and various keratins (classic markers of epithelium). All TECCs, including those with malignant cytomorphology, stained without exception for endothelial markers such as CD31, VWF or CD144 (FIG. 8B) but were negative for CD45 or markers of megakaryocytic lineages CD41 and CD42B. This indicated that in the colorectal cancer patients, all TECCs detected were of endothelial origin. In addition, single tumor cells within TECCS were not detected. The present findings were in line with El-Heliebi et al., who reported CD31 expression on circulating non-hematologic cells (CNHC) from kidney cancer patients, but were dissimilar from a recent report that described CTC clusters of malignant origins (Aceto et al.). Lineage inference from the RNA-Seq data of CTC clusters described in Aceto et al. in fact indicated the presence of epithelial derived cells. TECCs characterized in the present study represented thus a distinct population of circulating endothelial cell clusters in colorectal cancer patients.

RNA-Seq data principal component analysis. Principal component analysis on the complete RNA-Seq dataset (FIG. 9a-c) was performed. Rank correlations coefficients were calculated by selecting the top 300 genes sorted by their maximum loading in the 1st to 3rd principal component. From this list, the Spearman rank correlation coefficient (p) was calculated for each TECC and tissues and the resulting data were plotted as a heatmap. Dendrograms were generated by average linkage clustering.

RNA-Seq data lineage inference. Workflow for lineage inference is presented in FIG. 14 and was implemented in an R script available upon request. Briefly, the primary cell atlas dataset (GSE49910) (Mabbott et al.) was obtained and expression data from 298 different experiments were selected, corresponding to N=42 different cell types or 'lineages'(FIG. 15). For each gene g in each lineage l, a 'specificity index' S was calculated based on Shannon information entropy and the Q statistics introduced by Schug et al., $$S_{(l|g)} = -\sum_{l=1}^{N} p_{(l|g)} \cdot \log_2(p_{(l|g)}) - \log_2(p_{(l|g)})$$

where p(l|g) is the relative expression of the gene g in the lineage l. Gene specificity was confirmed by visualizing expression data of genes with high specificity index using BioGPS (FIG. 14). For each lineage the top 80 genes with highest specificity index ('specific genes') (FIG. 14a) were selected. 80 genes were chosen as this provided the best resolution in the analysis reported herein. Next, for each RNA-Seq sample, the number of genes specific for each lineage was calculated. At the same time, 1,000× lists of 80 randomly selected genes were generated from the Affymetrix HG-U133_Plus_2 gene list ('random genes') and the average number of genes present by chance in each experimental RNA-Seq profile was determined. Finally, it was examined whether the number of enriched specific genes was equal to the number of randomly enriched genes by performing a Fisher exact test for each tested lineage in each experimental sample. The odds ratios for each test were mean-centered, scaled and visualized in a heat map comprising all tested lineages. The final results were used to generate hypotheses on cellular lineages based on the distribution of the normalized odds ratios. The algorithm was validated using published RNA-Seq datasets generated from various cell types and tissues (FIG. 15).

Endothelial progenitor cell (EPC) assay. Colony-forming EPC assay was performed as previously described (Kalka et al., Colombo et al.). Briefly, living endothelial TECCs were counted in 2-ml microfiltrates by CD144 and Calcein AM fluorescent staining. Unstained microfiltrates from 2 ml of blood from a second device was then placed in culture on 96-well plate coated with fibronectin (1 μg/cm$^2$) (Sigma-Aldrich) in the presence of EGM-2 cell culture medium (Lonza). Presence of TECC was confirmed by bright field microscopy before incubation. HUVECs were used as positive control as follow: 10,000 HUVECs were spiked in 2 ml of donor blood and isolated by microfiltration using two devices. In one device, retrieved HUVECs were quantified by CD144 and Calcein AM staining. HUVECs retrieved from the other device were seeded at defined numbers (5, 10, 20, 40, 80 and 160 cells) in octuplicate wells. After 2 days, the medium was changed and cells were allowed to grow for a total of 30 days by changing half of the medium every other day. Presence and viability of colonies were monitored every week under bright field microscopy. After 30 days, cells were detached by trypsinisation, stained using CD144 antibodies, Calcein AM and Hoechst 33342, and quantified under an 1×81 (Olympus) inverted fluorescence microscope.

Microvessel density and lumen count. Microvessel density (MVD) count was performed using immunofluorescence images of CD31-stained tissue sections as described previously (Wild et al., Gupta et al.) and using ImageJ (Schneider et al.). Briefly, fresh tissues were embedded in Tissue-Tek O.C.T Compound (Sakura) and stored at −80° C. until further use. From all available tissues, five-micrometer cryostat sections were cut on poly-L-lysine slides, fixed in PBS containing 4% paraformaldehyde for 8 min, washed in PBS, and stained using PE-anti-CD antibodies (1:20, clone WM59, BioLegend). The whole tumor area for each tissue section was imaged with a 10× objective by means of an 1×71 microscope system (Olympus) and the MetaMorph software (Molecular Devices). Before imaging and throughout MVD and lumen count, patient's IDs were blinded to avoid subjective bias during data acquisition and analysis.

Endothelial cell isolation from fresh tissues. Endothelial cells were isolated from normal colon and tumor tissues as previously described (Van Beijnum et al.) with minor modifications of the protocol. Briefly, fresh tissues were minced and digested for 60 min at 37° C. using collagenase, dispase and DNAse as described. After a Ficoll-Paque density centrifugation step, a two-step magnetic selection was performed using MACS reagents and materials (Miltenyi Biotec) following manufacturer's instructions. First, CD45$^-$ expressing cells were depleted by negative selection on LD columns, after labelling the cells with anti-CD45 magnetic beads and Human FcR Blocking Reagent. The CD45-depleted fraction was next collected and a second labelling was performed by adding anti-CD31 magnetic beads and human FcR Blocking Reagent. After a positive selection using MS columns the fraction with enriched CD31$^+$CD45$^-$ cells was stored at −80° C. until further use.

Detection of TECCs in Patients with Cancers Other than Colorectal Cancer

TECCs not only can be detected in the blood of colorectal cancer patients, but can also be detected in patients with other malignancies such as breast cancer, prostate cancer, kidney cancer, transitional cell carcinoma, lung cancer and cholangiocarcinoma (see Tables 3 and 4). Therefore, biomarkers for TECCs can be used for the detection of any types of cancer, and also for monitoring and predicting the outcomes of therapeutic treatments such as chemotherapy or surgery.

TABLE 3

TECC count correlate with response to therapy in patients with different types of metastatic disease. Clinical trial details can be accessed at clinicaltrials.gov using the following ID: NCT02435927.

| Patient ID | Disease | TECC count at Baseline | TECC count after treatment | Overall target RECIST response (at TECC count after treatment) |
|---|---|---|---|---|
| ASLAN-0003-FST | Metastatic cholangiocarcinoma | 22 | 3 | −30% |
| ASLAN-0004-HCH | Metastatic breast carcinoma | 14 | 2 | −4% |
| ASLAN-0006-CAM | Metastatic colorectal cancer | 25 | 2 | −11% |
| ASLAN-1002-GMC | Metastatic colorectal cancer | 13 | 0 | −27% |
| ASLAN-1005-NBC | Metastatic colorectal cancer | 26 | 5 | +2% |
| ASLAN-1010-YLB | Metastatic colorectal cancer | 17 | 6 | −42% |

TABLE 4

TECC count in transitional cell carcinoma patients before and after surgery

| Patient ID | Disease | TECC count at Baseline | TECC count after treatment | Treatment type |
|---|---|---|---|---|
| TCC-001 | Transitional cell carcinoma | 33 | 4 | Surgery |
| TCC-002 | Transitional cell carcinoma | 58 | 12 | Surgery |
| TCC-003 | Transitional cell carcinoma | 208 | 4 | Surgery |
| TCC-004 | Transitional cell carcinoma | 0 | 0 | Surgery |

Statistical analysis. Statistical analysis was performed in R environment (version 3.1.0) (R Core Team et al.). Unpaired samples were tested using two-tailed Wilcoxon-Mann-Whitney U test with Bonferroni correction in case of multiple comparisons. For each test, exact P value with location parameter (Hodges-Lehmann estimate $\hat{\Delta}$) and its 95% confidence interval (CI) were computed using the 'coin' package (Zeileis et al.). For paired samples, a two-tailed exact Wilcoxon signed-rank test was used. ROC curves with AUC and 95% CI intervals were computed using the 'pROC' package (Robin et al.). For easy interpretation and comparison of effect sizes, the effect size r for each statistical test was derived as follows: $r=|Z|/\sqrt{n}$ where Z is the Z score of the Wilcoxon-Mann-Whitney U or the Wilcoxon signed-rank test (Rosenthal, et al.). r from AUC was derived as described in Rice & Harris (Rice et al.). As introduced by Cohen (Cohen et al.), the following interpretations were applied: r=0.1, small effect; r=0.3, medium effect; r=0.5, large effect. Boxplots are shown as boxes representing the interquartile range (IQR) with a line across the box indicating the median, whiskers indicate 1.5×IQR. To derive the minimal sample size required to the case control study, it was first assumed there was no association between presence of TECC and presence of colorectal cancer (null hypothesis) and for a target power of 0.95, a minimal sample size of n=72 was estimated using the pwr.chisq.test function of the 'pwr' package (Champely et al.). An effect size w=0.5 at the significance level of 0.01 was assumed, where w=0.5 was chosen based on a pilot test of five colorectal cancer patients, information derived from four healthy controls with negative TECC counts and a review of the literature that reported no TECC in healthy individuals but widespread presence of TECC in cases in various cancer types (Supplementary Table 1). Correlations were tested using Kendall's tau ($\tau$) coefficient and its derived P value. For lineage inference and principal component analysis of RNA-Seq data, Fisher's exact tests and Spearman correlation coefficient ($\rho$) were used respectively, as described in the dedicated method paragraphs. Level of significance was set at 0.05. One asterisk (*), P<0.05; two asterisks (), P<0.01; three asterisks (*), P<0.001; not significant (ns), P≥0.05.

Results and Conclusion of Analysis of TECCs

TECCs isolated from colorectal cancer patients are not cancerous but represent a distinct population of tumor-derived endothelial cells. TECCs do not mirror the genetic variations of matching tumors, yet TECCS express epithelial and mesenchymal transcripts in agreement with previous reports on CTC phenotyping. Transcriptome analysis of single-TECC reveals their identity as endothelial cells with further results indicating their tumor origin and mature phenotype. Widespread presence of endothelial TECCs was found in blood sampled from preoperative, early stage cancer patients but not in healthy donors, suggesting endothelial TECC count as potential indicator for colorectal cancer. Endothelial TECCs should not be confused with bona fide CTCs although their analysis might be helpful diagnostically, and provide direct information on the underlying tumor vasculature during treatment and disease course.

In conclusion, the isolation, retrieval and analysis of single TECC from colorectal cancer patients presents for the first time transcriptome profiling of single-TECC and several lines of evidence for the tumor endothelial origin of TECCs. Endothelial TECCs were detected as structures of multiple cells. As such, TECCs might be shed from the chaotic tumor vasculature undergoing pathological angiogenesis, a recognized early event in colorectal tumor progression. Preclinical models might reveal the mechanisms underlying tumor endothelial cell shedding in circulation, and are currently under investigation. In contrast to CTCs, which are often detected in patients with advanced diseases, TECCs are tumor-derived entities prevalent in early stage and preoperative colorectal cancer patients. Endothelial TECC counts represent therefore an intriguing modus for early colorectal cancer detection. In this study, the presence of CTC clusters was not detected as reported in Aceto et al. This might be the result of differences in patient profiles. In fact, Aceto et al. analyzed blood samples from terminal breast cancer patients, whereas blood samples in this study were mostly derived from preoperative colorectal cancer patients. Further studies would need to address specificities of circulating endothelial cell clusters in various diseases. Interestingly, tissue-specific molecular signatures have been demonstrated in endothelial cells from various organs, indicating that TECC might be traced back to their organ of origin based on the expression of specific gene sets. Because of their cellular morphology reminiscent of malignancy, keratins expression and the mixed epithelial and mesenchymal marker profiles, endothelial TECCs should not be confused with bona fide malignant CTCs undergoing EMT. At the same time, endothelial TECC analysis might contribute to early colorectal cancer detection and provide direct information on the underlying tumor vasculature during treatment and disease course.

REFERENCES

Aceto, N. et al. Circulating tumor cell clusters are oligoclonal precursors of breast cancer metastasis. Cell 158, 1110-1122 (2014).
Champely, S. pwr: Basic Functions for Power Analysis. (R Foundation for Statistical Computing, Vienna, 2009).
Chard T, An Introduction to Radioimmunoassay and Related Techniques, Elsevier Science 1995, ISBN 0444821 198.
Cima, 1. et al. Label-free isolation of circulating tumor cells in microfluidic devices: current research and perspectives. Biomicrofluidics 7, 011810 (2013).
Cohen, J. Statistical Power Analysis for the Behavioral Sciences. (L. Erlbaum Associates, 1988).
Colombo, E., Calcaterra, F., Cappelletti, M., Mavilio, D. & Della Bella, S. Comparison of fibronectin and collagen in supporting the isolation and expansion of endothelial progenitor cells from human adult peripheral blood. PLoS One 8, e66734 (2013).
Coumans, F. A. W., van Dalum, G., Beck, M. & Terstappen, L. W. M. M. Filter characteristics influencing circulating tumor cell enrichment from whole blood. PLoS One 8, e61770 (2013). Crowther, John R. The ELISA Guidebook, 1$^{st}$ ed., Humana Press 2000, ISBN 0896037282
El-Heliebi, A. et al. Are morphological criteria sufficient for the identification of circulating tumor cells in renal cancer? J. Transl. Med. 11, 214 (2013).
Gosling, Immunoassays: A Practical Approach, Oxford University Press, 2000.
Gupta, G. P. et al. Mediators of vascular remodelling co-opted for sequential steps in lung metastasis. Nature 446, 765-770 (2007).
Kalka, C. et al. Transplantation of ex vivo expanded endothelial progenitor cells for therapeutic neovascularization. Proc. Natl. Acad. Sci. USA 97, 3422-3427 (2000).
Lim, L. S. et al. Microsieve lab-chip device for rapid enumeration and fluorescence in situ hybridization of circulating tumor cells. Lab on a Chip 12, 4388-4396 (2012).
Mabbott, N. A., Baillie, J. K., Brown, H., Freeman, T. C. & Hume, D. A. An expression atlas of human primary cells: inference of gene function from coexpression networks. BMC Genomics 14, 632 (2013).
Marrinucci D. et al, 2012, Phys. Biol. 9016003
Peixoto, A., Monteiro, M., Rocha, B. & Veiga-Femandes, H. Quantification of multiple gene expression in individual cells. Genome Res. 14, 1938-1947 (2004).
Price and Newman, Principles and Practice of Immunoassay, 2nd Edition, Grove's Dictionaries, 1997
R Core Team. R: A Language and Environment for Statistical Computing. (R Foundation for Statistical Computing, Vienna, 2005).
Rice, M. E. & Harris, G. T. Comparing effect sizes in follow-up studies: ROC Area, Cohen's d, and r. Law Hum. Behav. 29, 615-620 (2005).
Robin, X. et al. pROC: an open-source package for R and S+ to analyze and compare ROC curves. BMC Bioinformatics 12, 77 (2011).
Rosenthal, R. Meta-analytic Procedures for Social Research. (SAGE Publications, 1991).
Sanchez-Freire, V., Ebert, A. D., Kalisky, T., Quake, S. R. & Wu, J. C. Microfluidic single-cell real-time PCR for comparative analysis of gene expression patterns. Nature protocols 7, 829-38 (2012).
Schneider, C. A., Rasband, W. S. & Eliceiri, K. W. NIH Image to ImageJ: 25 years of image analysis. Nature Methods 9, 671-675 (2012).
Schug, J. et al. Promoter features related to tissue specificity as measured by Shannon entropy. Genome Biol. 6, R33 (2005).
Trapnell, C., Pachter, L. & Salzberg, S. L. TopHat: discovering splice junctions with RNA-Seq. Bioinformatics 25, 1105-1111 (2009).
Trapnell, C. et al. Transcript assembly and quantification by RNA-Seq reveals unannotated transcripts and isoform switching during cell differentiation. Nat. Biotechnol. 28, 511-515 (2010).
Wild, R., Ramakrishnan, S., Sedgewick, J. & Griffioen, A. W. Quantitative assessment of angiogenesis and tumor vessel architecture by computer-assisted digital image analysis: effects of VEGF-toxin conjugate on tumor microvessel density. Microvasc. Res. 59, 368-376 (2000).
Wu, C. et al. BioGPS: an extensible and customizable portal for querying and organizing gene annotation resources. Genome Biol. 10, R130 (2009).
Ye, J. et al. Primer-BLAST: A tool to design target-specific primers for polymerase chain reaction. BMC Bioinformatics 13, 134 (2012).
Van Beijnum, J. R., Rousch, M., Castermans, K., van der Linden, E. & Griffioen, A. W. Isolation of endothelial cells from fresh tissues. Nat. Protoc. 3, 1085-1091 (2008).
Zeileis, A., Wiel, M., Hornik, K. & Hothom, T. Implementing a class of permutation tests: The coin package. J. Stat. Softw. 28, 1-23 (2008).
Supplementary Tables 1-7

SUPPLEMENTARY TABLE 1

Selected publications including circulating tumor cell clusters or CTM described as cancerous entities (1059-2014)

| # | Year | Article reporting CTM or CTC clusters as cancerous entity | Experimental evidence used to define malignancy |
|---|---|---|---|
| 1 | 1959 | Engell, H. | Cytomorphology |
| 2 | 1960 | Finkel, G. C., & Tishkoff, G. H. | Cytomorphology |
| 3 | 1964 | Seal, S. H. | Cytomorphology |
| 4 | 1964 | Sellwood, R. A. et al. | Cytomorphology |
| 5 | 1965 | Cole, W. H. et al. | Cytomorphology |
| 6 | 1971 | Song, J., et al. | Cytomorphology |
| 7 | 1973 | Griffiths, J. D. et al. | Cytomorphology |
| 8 | 1975 | Salsbury, A. J. | Cytomorphology |
| 9 | 1979 | Ejeckam, G. C. et al. | Cytomorphology/Myeloperoxidase staining |
| 10 | 1988 | Glaves, D. et al. | Cytomorphology/CK staining |
| 11 | 1992 | Aboulafia, D. M. | Cytomorphology/CK staining |
| 12 | 2000 | Vona, G. et al. | Cytomorphology/AFP staining |
| 13 | 2001 | Molnar, B et al. | Keratin magnetic labeling |
| 14 | 2004 | Vona, G. et al. | Cytomorphology/AFP staining |
| 15 | 2004 | Allard, W. J. et al. | Cytomorphology/CD45-keratin staining |
| 16 | 2007 | Paterlini-Brechot, P. & Benali, N. L. | Cytomorphology |
| 17 | 2010 | Stott, S. L, et al. | PSMA/CD45, CK7, 8/CD45 stainings |
| 18 | 2010 | Hou, J. M. et al. | Cytomorphology/CD45-NSE stainings |
| 19 | 2011 | Hou, J. M. st al. | CD45/various epithelial and mesenchymal markers immunostainings |

SUPPLEMENTARY TABLE 1-continued

Selected publications including circulating tumor cell clusters or CTM described as cancerous entities (1059-2014)

| # | Year | Article reporting CTM or CTC clusters as cancerous entity | Experimental evidence used to define malignancy |
|---|------|---|---|
| 20 | 2011 | Khoja, L. et al. | Cytomorphology/CD45-CK stainings |
| 21 | 2011 | Desitter, I. et al. | Cytomorphology/CD45-CK stainings |
| 22 | 2011 | Hofman, V. J. et al. | Cytomorphology |
| 23 | 2011 | Hofman, V. et al. | Cytomorphology |
| 24 | 2012 | Hou, J. M. et al. | EPCAM/CD45/CK/Ki67/Mcl-1 stainings |
| 25 | 2012 | Kling, J. | CD45-CK stainings |
| 26 | 2012 | Cho, E. H. et al. | CD45-CK stainings |
| 27 | 2012 | Krebs, M. G. et al. | Cytomorphology/CD45 |
| 28 | 2012 | Marrinucci, D. et al. | CD45-CK stainings Epithelial and mesenchymal transcript and protein markers, high-throughput |
| 29 | 2013 | Yu, M. et al. | RNA sequencing Various stainings including PSMA, EPCAM, CK. Single cell high-throughput |
| 30 | 2014 | Aceto, N. et al. | sequencing |

Supplementary Table 2: Targeted high-throughput sequencing of single TECC do not mirror matching primary tumor mutations

| Gene | Position | Type | Zygosity | Genotype | ExonicFunc.refGene | Patient 13 P13-Tumor |
|---|---|---|---|---|---|---|
| KRAS | KRAS: chr12: 25398284 | SNP | Het | C/T | nonsynonymous SNV | NA |
| PIK3CA | PIK3CA: chr3: 178936095 | SNP | Het | A/G | nonsynonymous SNV | NA |
| TP53 | TP53: chr17: 7574003 | SNP | Het | G/A | stopgain SNV | NA |
| TP53 | TP53: chr17: 7577120 | SNP | Het | C/T | nonsynonymous SNV | NA |
| TP53 | TP53: chr17: 7578202 | DEL | Het | ACACTATGTCG/A | | NA |
| TP53 | TP53: chr17: 7578407 | SNP | Het | G/C | nonsynonymous SNV | 32.33082707 |
| TP53 | TP53: chr17: 7578463 | INS | Het | C/CG | frameshift insertion | NA |
| TP53 | TP53: chr17: 7578645 | SNP | Het | C/T | | NA |

Threshold: 10%

SUPPLEMENTARY TABLE 2

Targeted high-throughput sequencing of single TECC do not mirror matching primary tumor mutations

| Gene | P13-TECC2 | P13-TECC3 | P13-TECC4 | P13-TECC5 | P10-Tumor | P10-TECC1 | P10-TECC4 | P10-TECC5 |
|---|---|---|---|---|---|---|---|---|
| KRAS | NA | NA | NA | NA | NA | NA | NA | NA |
| PIK3CA | NA | NA | NA | NA | NA | NA | NA | NA |
| TP53 | NA | NA | NA | NA | NA | NA | NA | NA |
| TP53 | NA | NA | NA | NA | 49.17458729 | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | 98.611111111 | NA | NA | NA |

Treshold: 10%

SUPPLEMENTARY TABLE 2-continued

Targeted high-throughput sequencing of single TECC do not mirror matching primary tumor mutations

|      | | | Patient 14 | | | Patient 15 | |
| --- | --- | --- | --- | --- | --- | --- | --- |
| Gene | P10-TECC 10 | P10-TECC 12 | P14-Tumor | P14-TECC1 | P14-TECC2 | P15-Tumor | P15-TECC5 |
| KRAS | NA | NA | 68.43291995 | NA | NA | NA | NA |
| PIK3CA | NA | NA | NA | NA | NA | 59.67741935 | NA |
| TP53 | NA | NA | NA | NA | NA | 76.29072682 | NA |
| TP53 | NA | NA | NA | NA | NA | NA | NA |
| TP53 | NA | NA | NA | NA | NA | NA | NA |
| TP53 | NA | NA | NA | NA | NA | NA | NA |
| TP53 | NA | NA | 47.32098147 | NA | NA | NA | NA |
| TP53 | NA | NA | NA | NA | NA | NA | NA |

Treshold: 10%

|      | | Patient 7 | | | Patient 8 | |
| --- | --- | --- | --- | --- | --- | --- |
| Gene | P7-Tumor | P7-TECC6 | P7-TECC8 | P7-TECC9 | P8-Tumor | P8-TECC12 |
| KRAS | NA | NA | NA | NA | NA | NA |
| PIK3CA | NA | NA | NA | NA | NA | NA |
| TP53 | NA | NA | NA | NA | NA | NA |
| TP53 | NA | NA | NA | NA | 81.56565657 | NA |
| TP53 | NA | NA | NA | NA | NA | NA |
| TP53 | NA | NA | NA | NA | NA | NA |
| TP53 | NA | NA | NA | NA | NA | NA |
| TP53 | NA | NA | NA | NA | NA | NA |

Treshold: 10%

Supplementary Table 3: Sparse TECC mutations are not detected in matching primary tumor tissues

| Gene | Position | Type | Zygosity | Genotype | ExonicFunc.refGene | Patient 13 P13-Tumor | P13-TECC2 |
| --- | --- | --- | --- | --- | --- | --- | --- |
| AKT1 | AKT1: chr14: 105258943 | SNP | Het | T/C | nonsynonymous SNV | NA | NA |
| AKT1 | AKT1: chr14: 105258954 | SNP | Het | C/T | synonymous SNV | NA | NA |
| AKT1 | AKT1: chr14: 105258963 | SNP | Het | A/G | synonymous SNV | NA | NA |
| AKT1 | AKT1: chr14: 105259001 | SNP | Het | C/T | NA | NA | NA |
| AKT1 | AKT1: chr14: 105259015 | SNP | Het | T/C | NA | NA | NA |
| BRAF | BRAF: chr7: 140453027 | SNP | Het | T/C | NA | NA | NA |
| BRAF | BRAF: chr7: 140453110 | SNP | Het | G/A | stopgain SNV | NA | NA |
| BRAF | BRAF: chr7: 140453135 | SNP | Hom | A/A | synonymous SNV | NA | NA |
| BRAF | BRAF: chr7: 140453160 | DEL | Het | AT/A |  | NA | NA |
| BRAF | BRAF: chr7: 140453221 | SNP | Het | G/T | NA | NA | NA |
| CTNNB1 | CTNNB1: chr3: 41265533 | SNP | Het | A/C | NA | NA | NA |
| EGFR | EGFR: chr7: 55240848 | SNP | Hom | G/G | NA | NA | NA |

Supplementary Table 3: Sparse TECC mutations are not detected in matching primary tumor tissues

| Gene | Position | Type | Zygosity | Genotype | ExonicFunc.refGene | Patient 13 P13-Tumor | P13-TECC2 |
|---|---|---|---|---|---|---|---|
| EGFR | EGFR: chr7: 55241616 | DEL | Hom | T/T | | NA | NA |
| EGFR | EGFR: chr7: 55241661 | SNP | Het | C/T | synonymous SNV | NA | NA |
| EGFR | EGFR: chr7: 55251727 | SNP | Het | G/A | synonymous SNV | NA | NA |
| EGFR | EGFR: chr7: 55241730 | SNP | Hom | T/T | synonymous SNV | NA | NA |
| EGFR | EGFR: chr7: 55249014 | SNP | Het | A/G | nonsynonymous SNV | NA | NA |
| EGFR | EGFR: chr7: 55249133 | SNP | Het | T/C | nonsynonymous SNV | NA | NA |
| EGFR | EGFR: chr7: 55260481 | SNP | Het | T/C | nonsynonymous SNV | NA | NA |
| EGFR | EGFR: chr7: 55260492 | SNP | Het | T/C | synonymous SNV | NA | NA |
| KRAS | KRAS: chr12: 25378745 | SNP | Het | A/G | NA | NA | 12 |
| KRAS | KRAS: chr12: 25380190 | SNP | Het | A/G | nonsynonymous SNV | NA | NA |
| KRAS | KRAS: chr12: 25380261 | SNP | Het | G/C | nonsynonymous SNV | NA | NA |
| KRAS | KRAS: chr12: 25380262 | SNP | Het | C/T | nonsynonymous SNV | NA | NA |
| KRAS | KRAS: chr12: 25380285 | SNP | Het | G/T | nonsynonymous SNV | NA | NA |
| KRAS | KRAS: chr12: 25380307 | SNP | Het | A/C | nonsynonymous SNV | NA | NA |
| KRAS | KRAS: chr12: 25380309 | DEL | Het | GT/G | | NA | NA |
| KRAS | KRAS: chr12: 25398236 | SNP | Het | A/G | nonsynonymous SNV | NA | NA |
| NRAS | NRAS: chr1: 115256498 | SNP | Hom | T/T | | NA | NA |
| NRAS | NRAS: chr1: 115258685 | SNP | Het | C/T | nonsynonymous SNV | NA | NA |
| PIK3CA | PIK3CA: chr3: 178916625 | SNP | Het | A/G | synonymous SNV | NA | NA |
| PIK3CA | PIK3CA: chr3: 178916635 | SNP | Het | G/A | nonsynonymous SNV | NA | NA |
| PIK3CA | PIK3CA: chr3: 178916638 | DEL | Het | TGGGGCATCCACTT/G | | NA | NA |
| PTEN | PTEN: chr10: 89685300 | DEL | Hom | C/C | | NA | NA |
| PTEN | PTEN: chr10: 89690872 | SNP | Het | T/C | NA | NA | NA |
| PTEN | PTEN: chr10: 89690906 | SNP | Het | T/C | NA | NA | NA |
| PTEN | PTEN: chr10: 89692825 | DEL | Het | CT/C | | NA | NA |
| PTEN | PTEN: chr10: 89692891 | SNP | Het | A/G | synonymous SNV | NA | NA |
| PTEN | PTEN: chr10: 89692916 | SNP | Het | A/T | nonsynonymous SNV | NA | NA |
| PTEN | PTEN: chr10: 89711843 | SNP | Het | A/G | NA | NA | NA |
| PTEN | PTEN: chr10: 89711866 | SNP | Het | G/A | NA | NA | NA |
| PTEN | PTEN: chr10: 89711910 | SNP | Het | T/C | synonymous SNV | NA | NA |
| PTEN | PTEN: chr10: 89711998 | SNP | Het | T/C | nonsynonymous SNV | NA | NA |
| PTEN | PTEN: chr10: 89720698 | SNP | Het | A/G | synonymous SNV | NA | NA |
| PTEN | PTEN: chr10: 89720707 | SNP | Het | C/T | synonymous SNV | NA | NA |
| PTEN | PTEN: chr10: 89720709 | SNP | Het | C/T | nonsynonymous SNV | NA | NA |
| TP53 | TP53: chr17: 7572967 | SNP | Het | T/C | nonsynonymous SNV | NA | NA |
| TP53 | TP53: chr17: 7573857 | SNP | Het | A/G | NA | NA | NA |

-continued

Supplementary Table 3: Sparse TECC mutations are not detected in matching primary tumor tissues

| Gene | Position | Type | Zygosity | Genotype | ExonicFunc.refGene | Patient 13 P13-Tumor | P13-TECC2 |
|------|----------|------|----------|----------|--------------------|----------------------|-----------|
| TP53 | TP53: chr17: 7576637 | SNP | Het | T/A | nonsynonymous SNV | NA | NA |
| TP53 | TP53: chr17: 7577102 | SNP | Het | C/T | nonsynonymous SNV | NA | NA |
| TP53 | TP53: chr17: 7577127 | DEL | Het | CAA/C | | NA | NA |
| TP53 | TP53: chr17: 7577396 | SNP | Het | T/C | NA | NA | NA |
| TP53 | TP53: chr17: 7577444 | SNP | Het | A/G | NA | NA | NA |
| TP53 | TP53: chr17: 7577450 | SNP | Het | A/G | NA | NA | NA |
| TP53 | TP53: chr17: 7577559 | SNP | Hom | A/A | nonsynonymous SNV | NA | NA |
| TP53 | TP53: chr17: 7578155 | SNP | Het | A/G | NA | NA | NA |
| TP53 | TP53: chr17: 7578237 | SNP | Hom | T/T | synonymous SNV | NA | NA |
| TP53 | TP53: chr17: 7578297 | SNP | Het | C/T | NA | NA | NA |
| TP53 | TP53: chr17: 7578369 | DEL | Hom | A/A | | NA | NA |
| TP53 | TP53: chr17: 7578385 | SNP | Hom | T/T | nonsynonymous SNV | NA | NA |
| TP53 | TP53: chr17: 7578389 | DEL | Hom | G/G | | NA | NA |
| TP53 | TP53: chr17: 7578399 | SNP | Het | G/A | synonymous SNV | NA | NA |
| TP53 | TP53: chr17: 7578400 | SNP | Het | G/A | nonsynonymous SNV | NA | NA |
| TP53 | TP53: chr17: 7578502 | SNP | Het | A/G | nonsynonymous SNV | NA | NA |
| TP53 | TP53: chr17: 7578645 | SNP | Hom | T/T | | NA | NA |
| TP53 | TP53: chr17: 7579393 | SNP | Het | A/G | synonymous SNV | NA | NA |
| TP53 | TP53: chr17: 7579432 | SNP | Het | A/G | | NA | 14.814815 |
| TP53 | TP53: chr17: 7579432 | DEL | Het | AG/AGG | | NA | NA |

Threshold: 10%

SUPPLEMENTARY TABLE 3

Sparse TECC mutations are not detected in matching primary tumor tissues

| Gene | P13-TECC3 | P13-TECC4 | P13-TECC5 | Patient 10 | | | | |
|---|---|---|---|---|---|---|---|---|
| | | | | P10-Tumor | P10-TECC1 | P10-TECC4 | P10-TECC5 | P10-TECC10 |
| AKT1 | NA | NA | NA | NA | 26.869159 | NA | NA | NA |
| AKT1 | NA | NA | NA | NA | NA | NA | 12.262357 | NA |
| AKT1 | NA | NA | NA | NA | 15.242494 | NA | NA | NA |
| AKT1 | NA | NA | NA | NA | NA | NA | 11.568123 | NA |
| AKT1 | NA | NA | NA | NA | NA | 39.308963 | NA | NA |
| BRAF | NA | NA | NA | NA | NA | NA | NA | NA |
| BRAF | NA | NA | NA | NA | NA | NA | NA | NA |
| BRAF | NA | NA | NA | NA | NA | NA | NA | NA |
| BRAF | NA | NA | NA | NA | NA | NA | NA | NA |
| BRAF | NA | NA | NA | NA | NA | NA | NA | NA |
| CTNNB1 | NA | NA | NA | NA | NA | NA | NA | NA |
| EGFR | NA | NA | 100 | NA | NA | NA | NA | NA |
| EGFR | NA | NA | 100 | NA | NA | NA | NA | NA |
| EGFR | NA | NA | NA | NA | NA | NA | NA | NA |
| EGFR | NA | NA | NA | NA | NA | NA | NA | NA |
| EGFR | NA | NA | 100 | NA | NA | NA | NA | NA |
| EGFR | NA | NA | NA | NA | NA | NA | NA | NA |
| EGFR | NA | NA | NA | NA | NA | NA | NA | NA |
| EGFR | NA | NA | NA | NA | NA | NA | NA | 13.173653 |
| EGFR | NA | 25.728643 | NA | NA | NA | NA | NA | NA |
| KRAS | NA | NA | NA | NA | NA | NA | NA | NA |
| KRAS | NA | NA | NA | NA | NA | NA | NA | NA |
| KRAS | NA | NA | NA | NA | NA | NA | NA | NA |
| KRAS | NA | NA | NA | NA | NA | NA | NA | NA |
| KRAS | NA | NA | NA | NA | NA | NA | NA | NA |
| KRAS | NA | NA | NA | NA | NA | NA | NA | NA |

SUPPLEMENTARY TABLE 3-continued

Sparse TECC mutations are not detected in matching primary tumor tissues

| | | | | | | | | |
|---|---|---|---|---|---|---|---|---|
| KRAS | NA | NA | 58.930373 | NA | NA | NA | NA | NA |
| KRAS | NA | NA | NA | NA | NA | NA | NA | NA |
| NRAS | NA | NA | NA | NA | NA | NA | NA | NA |
| NRAS | NA | NA | 20.731097 | NA | NA | NA | NA | NA |
| PIK3CA | NA | NA | NA | NA | NA | NA | NA | NA |
| PIK3CA | NA | NA | NA | NA | NA | NA | NA | NA |
| PIK3CA | NA | NA | NA | NA | NA | NA | NA | NA |
| PTEN | NA | NA | NA | NA | NA | NA | NA | NA |
| PTEN | NA | NA | 10.619469 | NA | NA | NA | NA | NA |
| PTEN | NA | NA | NA | NA | NA | NA | NA | NA |
| PTEN | NA | NA | NA | NA | NA | NA | NA | NA |
| PTEN | NA | NA | NA | NA | NA | NA | NA | NA |
| PTEN | NA | NA | NA | NA | NA | NA | NA | NA |
| PTEN | NA | NA | NA | NA | NA | NA | NA | NA |
| PTEN | NA | NA | NA | NA | NA | NA | NA | 13.293944 |
| PTEN | NA | NA | NA | NA | NA | NA | NA | 13.543307 |
| PTEN | NA | NA | NA | NA | NA | NA | NA | NA |
| PTEN | NA | NA | NA | NA | NA | NA | NA | NA |
| PTEN | NA | NA | 14.035088 | NA | NA | NA | NA | NA |
| PTEN | NA | NA | NA | NA | NA | NA | NA | NA |
| TP53 | NA | NA | NA | NA | NA | NA | NA | 34.554974 |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |

SUPPLEMENTARY TABLE 3-continued

Sparse TECC mutations are not detected in matching primary tumor tissues

| TP53 | NA | NA | NA | NA | NA | NA | NA | NA |
| --- | --- | --- | --- | --- | --- | --- | --- | --- |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | 38.157895 |
| TP53 | NA | NA | NA | NA | NA | NA | NA | NA |
| TP53 | NA | NA | NA | NA | NA | NA | NA | 59.375 |

Treshold: 10%

|  |  | Patient 14 | | | Patient 15 | | Patient 7 | |
| --- | --- | --- | --- | --- | --- | --- | --- | --- |
| Gene | P10-TECC12 | P14-Tumor | P14-TECC1 | P14-TECC2 | P15-Tumor | P15-TECC5 | P7-Tumor | P7-TECC6 |
| AKT1 | NA | NA | NA | NA | NA | NA | NA | NA |
| AKT1 | NA | NA | NA | NA | NA | NA | NA | NA |
| AKT1 | NA | NA | NA | NA | NA | NA | NA | NA |
| AKT1 | NA | NA | NA | NA | NA | NA | NA | NA |
| AKT1 | NA | NA | NA | NA | NA | NA | NA | NA |
| BRAF | NA | NA | 37.5 | NA | NA | NA | NA | NA |
| BRAF | NA | NA | NA | 64.839468 | NA | NA | NA | NA |
| BRAF | NA | NA | NA | 100 | NA | NA | NA | NA |
| BRAF | NA | NA | 30.30303 | NA | NA | NA | NA | NA |
| BRAF | NA | NA | 56.149733 | NA | NA | NA | NA | NA |
| CTNNB1 | NA | NA | 23.333333 | NA | NA | NA | NA | NA |
| EGFR | NA | NA | NA | NA | NA | NA | NA | NA |
| EGFR | NA | NA | NA | NA | NA | NA | NA | NA |

SUPPLEMENTARY TABLE 3-continued

Sparse TECC mutations are not detected in matching primary tumor tissues

| | | | | | | | | |
|---|---|---|---|---|---|---|---|---|
| EGFR | NA | NA | NA | NA | NA | NA | NA | NA |
| EGFR | NA | NA | 50 | NA | NA | NA | NA | NA |
| EGFR | NA | NA | NA | NA | NA | NA | NA | NA |
| EGFR | 17.751479 | NA | NA | NA | NA | NA | NA | NA |
| EGFR | NA | NA | NA | NA | NA | NA | NA | NA |
| EGFR | NA | NA | NA | NA | NA | NA | NA | NA |
| EGFR | NA | NA | NA | NA | NA | NA | NA | NA |
| KRAS | NA | NA | NA | NA | NA | NA | NA | NA |
| KRAS | NA | NA | NA | NA | NA | NA | NA | NA |
| KRAS | NA | NA | NA | NA | NA | NA | NA | NA |
| KRAS | NA | NA | NA | NA | NA | NA | NA | NA |
| KRAS | NA | NA | 33.766234 | NA | NA | NA | NA | NA |
| KRAS | NA | NA | 11.538462 | NA | NA | NA | NA | NA |
| KRAS | NA | NA | NA | NA | NA | NA | NA | NA |
| KRAS | NA | NA | NA | 42.857143 | NA | NA | NA | NA |
| NRAS | NA | NA | NA | NA | NA | NA | NA | NA |
| NRAS | NA | NA | NA | NA | NA | NA | NA | NA |
| PIK3CA | NA | NA | 22.413793 | NA | NA | NA | NA | NA |
| PIK3CA | NA | NA | NA | NA | NA | NA | NA | NA |
| PIK3CA | NA | NA | NA | NA | NA | NA | NA | NA |
| PTEN | NA | NA | NA | NA | NA | NA | NA | NA |
| PTEN | NA | NA | NA | NA | NA | NA | NA | NA |
| PTEN | NA | NA | NA | NA | NA | 18.233296 | NA | NA |
| PTEN | NA | NA | NA | NA | NA | NA | NA | NA |
| PTEN | NA | NA | 10.344828 | NA | NA | NA | NA | NA |
| PTEN | NA | NA | NA | NA | NA | NA | NA | NA |
| PTEN | NA | NA | NA | NA | NA | NA | NA | NA |
| PTEN | NA | NA | NA | NA | NA | NA | NA | NA |
| PTEN | NA | NA | NA | NA | NA | NA | NA | NA |
| PTEN | NA | NA | 72.727273 | NA | NA | NA | NA | NA |
| PTEN | NA | NA | NA | NA | NA | NA | NA | NA |
| PTEN | NA | NA | NA | NA | NA | NA | NA | NA |
| PTEN | NA | NA | 47.727273 | NA | NA | NA | NA | NA |
| TP53 | NA | NA | NA | NA | NA | NA | NA | NA |
| TP53 | NA | NA | 13.571429 | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | 19.088319 | NA | NA | NA | NA | NA |
| TP53 | 10.515774 | NA | NA | NA | NA | NA | NA | NA |

SUPPLEMENTARY TABLE 3-continued

Sparse TECC mutations are not detected in matching primary tumor tissues

| | | | | | | | | |
|---|---|---|---|---|---|---|---|---|
| TP53 | NA | NA | NA | NA | NA | NA | NA | NA |
| TP53 | NA | NA | NA | NA | NA | NA | NA | NA |
| TP53 | NA | NA | NA | NA | NA | 100 | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | 100 |
| TP53 | NA | NA | NA | NA | NA | NA | NA | 100 |
| TP53 | NA | NA | NA | NA | NA | NA | NA | 100 |
| TP53 | NA | NA | NA | NA | NA | NA | NA | 97.345133 |
| TP53 | NA | NA | 11.188813 | NA | NA | NA | NA | NA |
| TP53 | NA | NA | 17.241379 | NA | NA | NA | NA | NA |
| TP53 | NA | NA | NA | NA | NA | NA | NA | 100 |
| TP53 | NA | NA | NA | NA | NA | NA | NA | NA |
| TP53 | NA | NA | NA | NA | NA | NA | NA | NA |
| TP53 | NA | NA | NA | NA | NA | NA | NA | NA |

Treshold: 10%

| | | | Patient 8 | |
|---|---|---|---|---|
| Gene | P7-TECC8 | P7-TECC9 | P8-Tumor | P8-TECC12 |
| AKT1 | NA | NA | NA | NA |
| AKT1 | NA | NA | NA | NA |
| AKT1 | NA | NA | NA | NA |
| AKT1 | NA | NA | NA | NA |
| AKT1 | NA | NA | NA | NA |
| BRAF | NA | NA | NA | NA |
| BRAF | NA | NA | NA | NA |
| BRAF | NA | NA | NA | NA |
| BRAF | NA | NA | NA | NA |
| BRAF | NA | NA | NA | NA |
| CTNNB1 | NA | NA | NA | NA |
| EGFR | NA | NA | NA | NA |

SUPPLEMENTARY TABLE 3-continued

Sparse TECC mutations are not detected in matching primary tumor tissues

| | | | | |
|---|---|---|---|---|
| EGFR | NA | NA | NA | NA |
| EGFR | 35 | NA | NA | NA |
| EGFR | NA | NA | NA | NA |
| EGFR | NA | NA | NA | NA |
| EGFR | NA | NA | NA | NA |
| EGFR | 23.880597 | NA | NA | NA |
| EGFR | NA | NA | NA | NA |
| EGFR | NA | NA | NA | NA |
| KRAS | NA | NA | NA | NA |
| KRAS | NA | NA | NA | 19.626168 |
| KRAS | NA | NA | NA | NA |
| KRAS | NA | NA | NA | 16.8 |
| KRAS | NA | NA | NA | NA |
| KRAS | NA | NA | NA | NA |
| KRAS | NA | NA | NA | NA |
| KRAS | NA | NA | NA | NA |
| NRAS | NA | 98.372966 | NA | NA |
| NRAS | NA | NA | NA | NA |
| PIK3CA | NA | NA | NA | NA |
| PIK3CA | NA | NA | NA | 91.941392 |
| PIK3CA | NA | NA | NA | 88.489209 |
| PTEN | NA | NA | NA | NA |
| PTEN | NA | NA | NA | NA |
| PTEN | NA | NA | NA | NA |
| PTEN | 40 | NA | NA | NA |

SUPPLEMENTARY TABLE 3-continued

Sparse TECC mutations are not detected in matching primary tumor tissues

| | | | | |
|---|---|---|---|---|
| PTEN | NA | NA | NA | NA |
| PTEN | 18.518519 | NA | NA | NA |
| PTEN | 19.485294 | NA | NA | NA |
| PTEN | NA | NA | NA | NA |
| PTEN | NA | NA | NA | NA |
| PTEN | NA | NA | NA | NA |
| PTEN | 11.666667 | NA | NA | NA |
| PTEN | NA | NA | NA | NA |
| PTEN | NA | NA | NA | NA |
| TP53 | NA | NA | NA | NA |
| TP53 | NA | NA | NA | NA |
| TP53 | NA | NA | NA | NA |
| TP53 | 10.714286 | NA | NA | NA |
| TP53 | NA | NA | NA | NA |
| TP53 | NA | NA | NA | NA |
| TP53 | NA | 13.157895 | NA | NA |
| TP53 | NA | 18.421053 | NA | NA |
| TP53 | NA | NA | NA | NA |
| TP53 | NA | NA | NA | 14.220183 |
| TP53 | NA | NA | NA | 98.536585 |
| TP53 | NA | NA | NA | NA |
| TP53 | NA | NA | NA | NA |
| TP53 | NA | NA | NA | NA |
| TP53 | NA | NA | NA | NA |
| TP53 | NA | NA | NA | NA |
| TP53 | NA | NA | NA | NA |
| TP53 | NA | NA | NA | 100 |
| TP53 | NA | NA | NA | NA |
| TP53 | NA | NA | NA | NA |
| TP53 | NA | NA | NA | NA |

Treshold: 10%

SUPPLEMENTARY TABLE 4

RNA-seq data, uniquely mapped reads to hg19 exons

| ID | #Unique reads mapped to hg19 exons |
|---|---|
| P10-T | 9,824,250 |
| P19-Met | 9,200,220 |
| P1-N | 12,046,807 |
| P1-TUc | 11,627,650 |
| P1-TUd | 10,474,561 |
| P1-TUs | 12,120,551 |

SUPPLEMENTARY TABLE 4-continued

RNA-seq data, uniquely mapped reads to hg19 exons

| ID | #Unique reads mapped to hg19 exons |
|---|---|
| P18-N | 11,691,022 |
| P18-T | 10,077,598 |
| P10-N | 11,940,709 |
| P21-N | 12,115,725 |
| P21-T | 10,030,315 |
| P20-N | 9,710,218 |
| P20-T | 7,196,431 |
| P8-N | 9,574,544 |
| P8-T | 9,413,088 |
| P19-N | 9,868,631 |
| P19-T | 9,156,651 |
| P8-TECC10 | 7,055,733 |
| P8-TECC11 | 6,873,889 |
| P16-TECC2 | 772,636 |
| P21-TECC11 | 6,526,429 |
| P19-TECC2 | 741,682 |
| P1-TECC1 | 3,368,445 |
| P1-TECC3 | 4,825,103 |
| P1-TECC4 | 5,493,502 |
| P10-TECC10 | 2,916,536 |
| P18-TECC4 | 357,116 |
| P18-TECC6 | 3,113,219 |
| P20-TECC16 | 1,001,059 |
| P20-TECC14 | 896,617 |
| P1-TECC8 | 620,380 |
| P18-TECC5 | 1,363,670 |
| P8-TECC7 | 3,763,227 |
| P20-TECC15 | 1,424,262 |
| P18-TECC2 | 1,007,933 |

Legend:
P, patient
T, tumor tissue
c, center
d, deep
s, superficial
N, normal tissue
Met, metastasis
TECC, tumor-derived endothelial cell clusters

SUPPLEMENTARY TABLE 5

Figure 4:
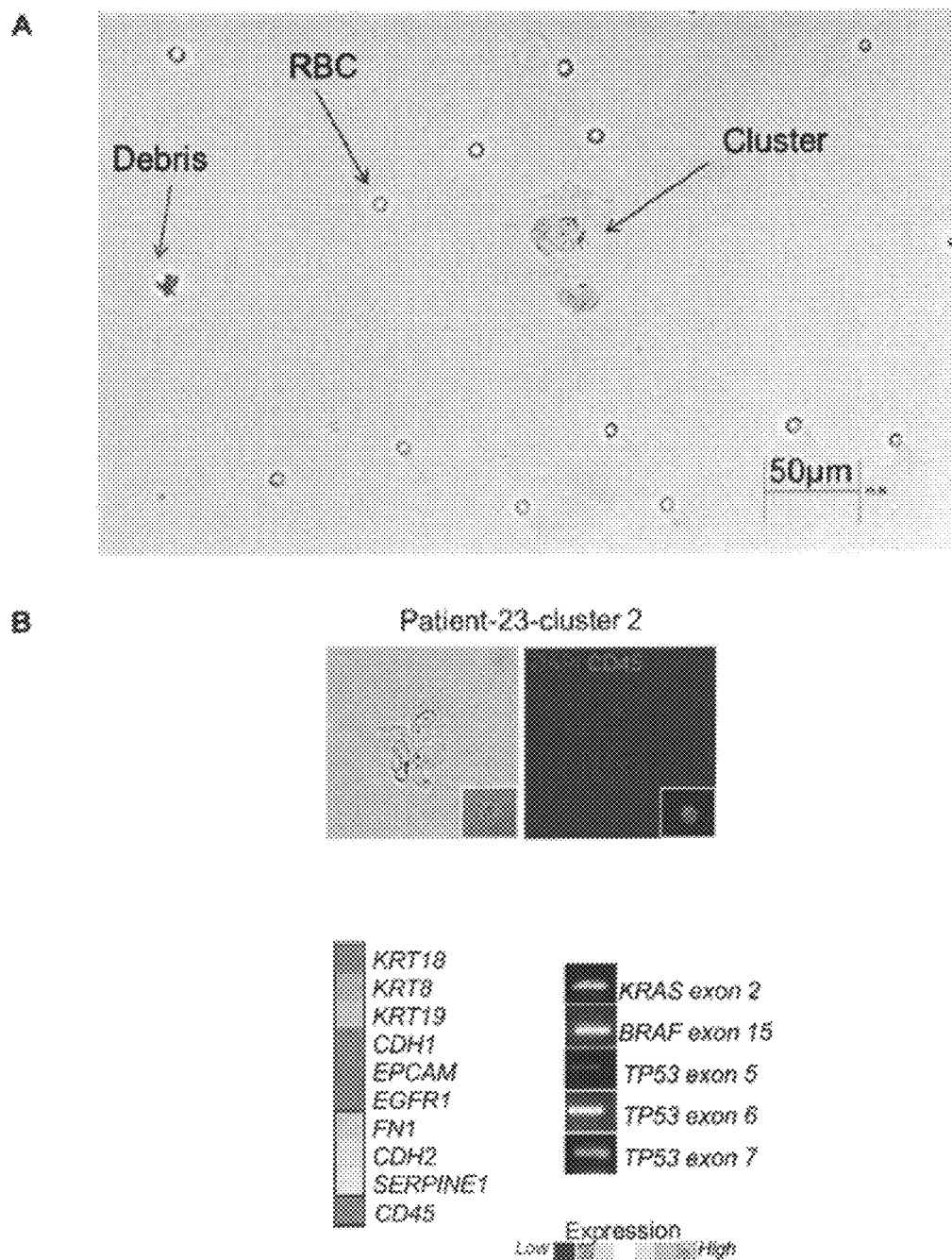
FIG. 4 shows the visualization of cells captured and retrieved using the device described herein. (A) shows that cells retrieved from the blood of colorectal cancer patient could be easily visualized by inverted fluorescence microscopy using standard differential interference contrast (DIC). Large multinucleated cell cluster or microemboli were observed. (B) shows that cellular clusters retrieved from clinical samples could be easily micromanipulated and analyzed for their gene expression and genomic DNA content. In this example, a cellular cluster was identified by means of immunofluorescence staining for CD45 and DAPI, and subsequently micromanipulated for analysis of gene expression and genomic DNA content.

Pre- and post surgery TECC count. Data from FIG. 4 e

| | TECC count | |
|---|---|---|
| Patient | Pre | Post |
| P05 | 9 | 6 |
| P19 | 2 | 0 |
| P22 | 124 | 0 |
| P54 | 0 | 3 |
| P64 | 4 | 0 |
| P66 | 46 | 0 |
| P67 | 1 | 0 |
| P69 | 0 | 0 |
| P71 | 79 | 2 |
| P72 | 24 | 0 |
| P73 | 48 | 0 |
| P74 | 13 | 2 |
| P75 | 3 | 0 |
| P77 | 1 | 0 |
| P78 | 1 | 0 |
| P80 | 0 | 0 |
| P82 | 36 | 0 |

Pre: TECC count in blood 0-24 hrs before surgery
Post: TECC count in blood 24-72 hrs after surgery

SUPPLEMENTARY TABLE 6

Baseline patients and healthy donors characteristics

| Characteristic | Patients | Controls |
|---|---|---|
| Total, n | 80 | 45 |
| Age, yr, median (range) | 60 (26-80) | 45 (26-81) |
| Gender, n (%) | | |
| Male | 48 (60) | 19 (43) |
| Female | 32 (40) | 25 (57) |
| Ethnicity, n (%) | | |
| Chinese | 56 (70) | |
| Other | 24 (30) | |
| Tumor Location n (%) | | |
| Recto-sigmoid | 67 (77) | |
| Other | 18 (23) | |
| Stage, n (%) | | |
| ≤IIA | 26 (35) | |
| IIB-IIIC | 26 (35) | |
| IV | 22 (30) | |
| Grade, n (%) | | |
| 1-2 | 58 (89) | |
| 3-4 | 7 (11) | |
| Metastatic CRC, n (%) | | |
| M0 (no distant metastasis) | 54 (72) | |
| M1 (distant metastasis) | 21 (28) | |
| Treatment, n (%) | | |
| Untreated | 52 (65) | |
| Neoadjuvant | 11 (14) | |
| Surgery* | 5 (6) | |
| Adjuvant | 4 (5) | |
| Palliative | 8 (10) | |

*post op. data from FIG. 3e not included

SUPPLEMENTARY TABLE 7

TECC count for each baseline sample type and number of single TECC analyzed in this study

| Patient ID | Abbreviation | Source | Baseline sample type | TECC count* |
|---|---|---|---|---|
| Donor 1 | D01 | NUH | Healthy | 0 |
| Donor 2 | D02 | NUH | Healthy | 0 |
| Donor 3 | D03 | NUH | Healthy | 0 |
| Donor 4 | D04 | NUH | Healthy | 0 |
| Donor 5 | D05 | NUH | Healthy | 0 |
| Donor 6 | D06 | NUH | Healthy | 0 |
| Donor 7 | D07 | NUH | Healthy | 0 |
| Donor 8 | D08 | NUH | Healthy | 0 |
| Donor 9 | D09 | NUH | Healthy | 0 |
| Donor 10 | D10 | NUH | Healthy | 0 |
| Donor 11 | D11 | NUH | Healthy | 0 |
| Donor 12 | D12 | NUH | Healthy | 0 |
| Donor 13 | D13 | IBN | Healthy | 0 |
| Donor 14 | D14 | NUH | Healthy | 0 |
| Donor 15 | D15 | NUH | Healthy | 0 |
| Donor 16 | D16 | NUH | Healthy | 0 |
| Donor 17 | D17 | NUH | Healthy | 0 |
| Donor 18 | D18 | NUH | Healthy | 0 |
| Donor 19 | D19 | NUH | Healthy | 0 |
| Donor 20 | D20 | NUH | Healthy | 0 |
| Donor 21 | D21 | NUH | Healthy | 0 |
| Donor 22 | D22 | NUH | Healthy | 0 |
| Donor 23 | D23 | NUH | Healthy | 0 |
| Donor 24 | D24 | NUH | Healthy | 0 |
| Donor 25 | D25 | NUH | Healthy | 0 |
| Donor 26 | D26 | NUH | Healthy | 0 |
| Donor 27 | D27 | NUH | Healthy | 0 |
| Donor 28 | D28 | NUH | Healthy | 0 |
| Donor 29 | D29 | IBN | Healthy | 0 |

SUPPLEMENTARY TABLE 7-continued

TECC count for each baseline sample type and number of single TECC analyzed in this study

| Patient ID | Abbreviation | Source | Baseline sample type | TECC count* |
|---|---|---|---|---|
| Donor 30 | D30 | IBN | Healthy | 0 |
| Donor 31 | D31 | IBN | Healthy | 0 |
| Donor 32 | D32 | IBN | Healthy | 0 |
| Donor 33 | D33 | NUH | Healthy | 0 |
| Donor 34 | D34 | NUH | Healthy | 0 |
| Donor 35 | D35 | NUH | Healthy | 0 |
| Donor 36 | D36 | NUH | Healthy | 0 |
| Donor 37 | D37 | NUH | Healthy | 0 |
| Donor 38 | D38 | NUH | Healthy | 0 |
| Donor 39 | D39 | NUH | Healthy | 0 |
| Donor 40 | D40 | NUH | Healthy | 0 |
| Donor 41 | D41 | NUH | Healthy | 0 |
| Donor 42 | D42 | NUH | Healthy | 0 |
| Donor 43 | D43 | NUH | Healthy | 0 |
| Donor 44 | D44 | NUH | Healthy | 9 |
| Donor 45 | D45 | NUH | Healthy | 0 |
| Patient 01 | P01 | NCC | CRC - Treatment Naive | 49 |
| Patient 02 | P02 | NCC | CRC - Treatment Naive | 3 |
| Patient 03 | P03 | FSH | CRC - Treatment Naive | 7 |
| Patient 04 | P04 | NCC | CRC - Palliative | 17 |
| Patient 05 | P05 | NCC | CRC - Treatment Naive | 9 |
| Patient 06 | P06 | FSH | CRC - Post Neoadjuvant | 0 |
| Patient 07 | P07 | FSH | CRC - Treatment Naive-Early stage | 26 |
| Patient 08 | P08 | FSH | CRC - Treatment Naive- Early stage | 76 |
| Patient 09 | P09 | FSH | CRC - Treatment Naive- Early stage | 52 |
| Patient 10 | P10 | FSH | CRC - Treatment Naive | 26 |
| Patient 11 | P11 | NCC | CRC - Palliative | 1 |
| Patient 12 | P12 | NCC | CRC - Palliative | 0 |
| Patient 13 | P13 | FSH | CRC - Treatment Naive- Early stage | 32 |
| Patient 14 | P14 | FSH | CRC - Treatment Naive-Early stage | 3 |
| Patient 15 | P15 | FSH | CRC - Treatment Naive- Early stage | 13 |
| Patient 16 | P16 | FSH | CRC - Treatment Naive | 2 |
| Patient 17 | P17 | FSH | CRC - Treatment Naive | 0 |
| Patient 18 | P18 | FSH | CRC - Treatment Naive- Early stage | 9 |
| Patient 19 | P19 | NCC | CRC - Treatment Naive | 2 |
| Patient 20 | P20 | FSH | CRC - Treatment Naive | 80 |
| Patient 21 | P21 | FSH | CRC - Treatment Naive | 16 |
| Patient 22 | P22 | FSH | CRC - Post Neoadjuvant | 124 |
| Patient 23 | P23 | FSH | CRC - Treatment Naive- Early stage | 12 |
| Patient 24 | P24 | FSH | CRC - Treatment Naive- Early stage | 23 |
| Patient 25 | P25 | FSH | CRC - Treatment Naive | 45 |
| Patient 26 | P26 | FSH | CRC - Treatment Naive | 5 |
| Patient 27 | P27 | FSH | CRC - Treatment Naive- Early stage | 34 |
| Patient 28 | P28 | FSH |  | NA |
| Patient 29 | P29 | FSH | CRC - Post Neoadjuvant | 15 |
| Patient 30 | P30 | FSH | CRC - Treatment Naive | 3 |
| Patient 31 | P31 | FSH | CRC - Treatment Naive | 0 |
| Patient 32 | P32 | FSH | CRC - Treatment Naive- Early stage | 18 |
| Patient 33 | P33 | FSH | CRC - Post Neoadjuvant | 3 |
| Patient 34 | P34 | FSH | CRC - Treatment Naive- Early stage | 2 |
| Patient 35 | P35 | FSH | CRC - Post Neoadjuvant | 2 |
| Patient 36 | P36 | FSH | CRC - Post Neoadjuvant | 0 |
| Patient 37 | P37 | FSH | CRC - Post Neoadjuvant | 1 |
| Patient 38 | P38 | FSH |  | NA |
| Patient 39 | P39 | FSH | CRC - Treatment Naive | 0 |
| Patient 40 | P40 | FSH | CRC - Treatment Naive- Early stage | 1 |
| Patient 41 | P41 | FSH | CRC - Treatment Naive | 2 |
| Patient 42 | P42 | FSH | CRC - Treatment Naive- Early stage | 3 |
| Patient 43 | P43 | FSH | CRC - Treatment Naive | 93 |
| Patient 44 | P44 | FSH | CRC - Treatment Naive | 48 |
| Patient 45 | P45 | FSH | CRC - Treatment Naive | 9 |
| Patient 46 | P46 | FSH | CRC - Treatment Naive | 249 |
| Patient 47 | P47 | FSH | CRC - Treatment Naive- Early stage | 0 |
| Patient 48 | P48 | FSH | CRC - Treatment Naive | 6 |
| Patient 49 | P49 | FSH | CRC - Treatment Naive | 25 |
| Patient 50 | P50 | FSH | CRC - Treatment Naive- Early stage | 0 |
| Patient 51 | P51 | NCC | CRC - Palliative | 24 |
| Patient 52 | P52 | NCC | CRC - Palliative | 0 |
| Patient 53 | P53 | NCC | CRC - Post Surgery | 0 |
| Patient 54 | P54 | NCC | CRC - Post Neoadjuvant | 0 |
| Patient 55 | P55 | NCC | CRC - Post Surgery | 0 |
| Patient 56 | P56 | NCC | CRC - Post Surgery | 0 |
| Patient 57 | P57 | NCC | CRC - Post Adjuvant | 0 |
| Patient 58 | P58 | NCC | CRC - Post Adjuvant | 6 |
| Patient 59 | P59 | NCC | CRC - Palliative | 1 |
| Patient 60 | P60 | NCC | CRC - Palliative | 0 |
| Patient 61 | P61 | NCC | CRC - Post Surgery | 0 |
| Patient 62 | P62 | NCC | CRC - Palliative | 3 |
| Patient 63 | P63 | NCC | CRC - Post Neoadjuvant | 40 |
| Patient 64 | P64 | NCC | CRC - Post Neoadjuvant | 4 |
| Patient 65 | P65 | NCC | CRC - Post Surgery | 0 |
| Patient 66 | P66 | NCC | CRC - Treatment Naive | 46 |
| Patient 67 | P67 | NCC | CRC - Treatment Naive | 1 |
| Patient 68 | P68 | NCC | CRC - Post Adjuvant | 0 |
| Patient 69 | P69 | NCC | CRC - Treatment Naive- Early stage | 0 |
| Patient 70 | P70 | NCC | CRC - Treatment Naive | 7 |
| Patient 71 | P71 | NCC | CRC - Treatment Naive | 79 |

SUPPLEMENTARY TABLE 7-continued

TECC count for each baseline sample type and number of single TECC analyzed in this study

| Patient ID | Abbreviation | Source | Baseline sample type | TECC count* |
|---|---|---|---|---|
| Patient 72 | P72 | NCC | CRC - Treatment Naive- Early stage | 24 |
| Patient 73 | P73 | NCC | CRC - Treatment Naive | 48 |
| Patient 74 | P74 | NCC | CRC - Treatment Naive- Early stage | 13 |
| Patient 75 | P75 | NCC | CRC - Treatment Naive- Early stage | 3 |
| Patient 76 | P76 | NCC | CRC - Treatment Naive | 12 |
| Patient 77 | P77 | NCC | CRC - Treatment Naive- Early stage | 1 |
| Patient 78 | P78 | NCC | CRC - Treatment Naive | 1 |
| Patient 79 | P79 | NCC | CRC - Treatment Naive- Early stage | 14 |
| Patient 80 | P80 | NCC | CRC - Treatment Naive | 0 |
| Patient 81 | P81 | NCC | CRC - Treatment Naive | 14 |
| Patient 82 | P82 | NCC | CRC - Post Neoadjuvant | 36 |

Legend:
NUH, National University Hospital Singapore
IBN, Institute of Bioengineering and Nanotechnology, Singapore
FSH, Fortis Surgical Hospital, Singapore
NCC, National Cancer Center, Singapore
CRC, Colorectal cancer
Early stage, stage ≤ IIA
*post-OP samples from FIG. 3f not included

---

The invention claimed is:

1. An apparatus for capturing and retrieving a cell from a sample, comprising at least one column, the column comprising:
   (i) an inner wall defining an inner chamber, the inner chamber having an inlet opening at a first end of the column for receiving the sample, and an outlet opening at a second end of the column;
   (ii) a perforated plug disposed within the inner chamber adjacent to the second end of the column;
   (iii) a sleeve insert having an opening at a first end and an opening at a second end, the sleeve insert comprising a channel tapered at the second end and disposed within the inner chamber with its second end adjacent to the perforated plug; and
   (iv) a filtering means housed within the sleeve insert, the filtering means comprising a sieve sandwiched between two sealing means.

2. The apparatus of claim 1, wherein the apparatus comprises two or more columns.

3. The apparatus of claim 1, wherein the second end of a column is adapted for connection to one or more pumps for controlling flow-rate of the sample through the column.

4. The apparatus of claim 3, wherein the apparatus further comprises one or more pumps and wherein a pump is adapted for passing the sample at a flow-rate selected from the group consisting of at least about 0.05 mL/min, at least about 0.10 mL/min, at least about 0.15 mL/min, at least about 0.20 mL/min, at least about 0.25 mL/min, at least about 0.30 mL/min, at least about 0.40 mL/min, and at least about 0.50 mL/min.

5. The apparatus of claim 1, wherein the sieve comprises one or more of the following: a non cell-adhesive material selected from the group consisting of silicon, silicon dioxide, silicon nitride, epoxy-based negative photoresist, ceramic, and an epoxy-based negative photoresist comprises SU-8.

6. The apparatus of claim 1, wherein the sieve comprises a plurality of pores having a diameter selected from the group consisting of at least about 6 µm, at least about 7 µm, at least about 8 µm, at least about 9 µm, at least about 10 µm, at least about 12 µm, at least about 14 µm, at least about 16 µm, at least about 18 µm and at least about 20 µm.

7. A kit comprising the apparatus of claim 1, and one or more of the following components:
   (a) one or more cell lysis buffers;
   (b) a set of primers comprising a first primer pair, a second primer pair, a nested primer and/or a nested primer pair; wherein the first or the second primer pair are selected from the group consisting of: (i) SEQ ID NO: 1 and SEQ ID NO: 2; (ii) SEQ ID NO: 3 and SEQ ID NO: 4; (iii) SEQ ID NO: 5 and SEQ ID NO: 6; (iv) SEQ ID NO: 7 and SEQ ID NO: 8; (v) SEQ ID NO: 9 and SEQ ID NO: 10; (vi) SEQ ID NO: 11 and SEQ ID NO: 12; (vii) SEQ ID NO: 13 and SEQ ID NO: 14; (viii) SEQ ID NO: 15 and SEQ ID NO: 16; (ix) SEQ ID NO: 17 and SEQ ID NO: 18; (x) SEQ ID NO: 19 and SEQ ID NO: 20; (xi) SEQ ID NO: 21 and SEQ ID NO: 22; (xii) SEQ ID NO: 23 and SEQ ID NO: 24; (xiii) SEQ ID NO: 25 and SEQ ID NO: 26; (xiv) SEQ ID NO: 27 and SEQ ID NO: 28; (xv) SEQ ID NO: 29 and SEQ ID NO: 30; (xvi) SEQ ID NO: 31 and SEQ ID NO: 32; (xvii) SEQ ID NO: 33 and SEQ ID NO: 34; (xviii) SEQ ID NO: 52 and 53; and (xix) SEQ ID NO: 54 and 55; and wherein the primer pair for semi-nested or nested PCR are selected from the group consisting of: (i) SEQ ID NO: 35 and SEQ ID NO: 2; (ii) SEQ ID NO: 3 and SEQ ID NO: 36; (iii) SEQ ID NO: 5 and SEQ ID NO: 37; (iv) SEQ ID NO: 38 and SEQ ID NO: 8; (v) SEQ ID NO: 39 and SEQ ID NO: 10; (vi) SEQ ID NO: 40 and SEQ ID NO: 12; (vii) SEQ ID NO: 41 and SEQ ID NO: 14; (viii) SEQ ID NO: 42 and SEQ ID NO: 16; (ix) SEQ ID NO: 17 and SEQ ID NO: 43; (x) SEQ ID NO: 44 and SEQ ID NO: 20; (xi) SEQ ID NO: 45 and SEQ ID NO: 22; (xii) SEQ ID NO: 46 and SEQ ID NO: 24;

(xiii) SEQ ID NO: 25 and SEQ ID NO: 47; (xiv) SEQ ID NO: 27 and SEQ ID NO: 48; (xv) SEQ ID NO: 49 and SEQ ID NO: 30; (xvi) SEQ ID NO: 31 and SEQ ID NO: 50; (xvii) SEQ ID NO: 51 and SEQ ID NO: 34; (xviii) SEQ ID NO: 56 and SEQ ID NO: 57; and (xix) SEQ ID NO: 58 and SEQ ID NO: 55;

(c) one or more reagents, selected from the group consisting of:

i. a reverse transcriptase and one or more suitable reaction buffers, ii. a DNA polymerase and one or more suitable reaction buffers, and iii. one or more labelled or unlabelled deoxyribonucleotides selected from the group consisting of dATP, dCTP, dGTP, and dTTP or dUTP; and (d) an antibody capable of specific binding to a protein selected from the group consisting of PAI-1, Vimentin, FOXC1, keratin-8, keratin-18, keratin-19, Ep-CAM, CD45, VWF, PECAM-1, CD146, CD41, CD34, PSMA, CD105, CD309, CD144, CD202B and Angiopoietin 2.

8. The kit of claim 7, wherein the antibody is coupled to a detectable label.

9. The kit of claim 8, wherein the kit further comprises a means for detecting the detectable label.

10. The kit of claim 7, wherein the set of primers and/or reagents are pre-mixed in combinations suitable for the lysis, pre-amplification, amplification, and/or for analysis of gene expression profiles or mutation signatures.

11. The kit of claim 7, wherein the kit further comprises instructions for using the kit components.

12. The kit of claim 7, wherein the kit further comprises one or more containers comprising the one or more reaction buffers for performing the nested and/or semi-nested PCR.

* * * * *

SEQUENCE LISTING

<160> NUMBER OF SEQ ID NOS: 58

<210> SEQ ID NO 1
<211> LENGTH: 17
<212> TYPE: DNA
<213> ORGANISM: Artificial Sequence
<220> FEATURE:
<223> OTHER INFORMATION: SERPINE1 Preamplification Forward Primer

<400> SEQUENCE: 1
gccaagagcg ctgtcaa                                                  17

<210> SEQ ID NO 2
<211> LENGTH: 19
<212> TYPE: DNA
<213> ORGANISM: Artificial Sequence
<220> FEATURE:
<223> OTHER INFORMATION: SERPINE1 Preamplification and Amplification
      Reverse Primer

<400> SEQUENCE: 2
cagcagaccc ttcaccaaa                                                19

<210> SEQ ID NO 3
<211> LENGTH: 20
<212> TYPE: DNA
<213> ORGANISM: Artificial Sequence
<220> FEATURE:
<223> OTHER INFORMATION: VIM Preamplification and Amplification Forward
      Primer

<400> SEQUENCE: 3
gatgtttcca agcctgacct                                               20

<210> SEQ ID NO 4
<211> LENGTH: 19
<212> TYPE: DNA
<213> ORGANISM: Artificial Sequence
<220> FEATURE:
<223> OTHER INFORMATION: VIM Preamplification Reverse Primer

<400> SEQUENCE: 4
cagtggactc ctgctttgc                                                19

-continued

<210> SEQ ID NO 5
<211> LENGTH: 20
<212> TYPE: DNA
<213> ORGANISM: Artificial Sequence
<220> FEATURE:
<223> OTHER INFORMATION: FOXC1 Preamplification and Amplification
      Forward Primer

<400> SEQUENCE: 5
cacaccctca aagccgaact                                              20

<210> SEQ ID NO 6
<211> LENGTH: 20
<212> TYPE: DNA
<213> ORGANISM: Artificial Sequence
<220> FEATURE:
<223> OTHER INFORMATION: FOXC1 Preamplification Reverse Primer

<400> SEQUENCE: 6
aaagtggagg tggctctgaa                                              20

<210> SEQ ID NO 7
<211> LENGTH: 20
<212> TYPE: DNA
<213> ORGANISM: Artificial Sequence
<220> FEATURE:
<223> OTHER INFORMATION: KRT8 Preamplification Forward Primer

<400> SEQUENCE: 7
aaggatgcca acgccaagtt                                              20

<210> SEQ ID NO 8
<211> LENGTH: 20
<212> TYPE: DNA
<213> ORGANISM: Artificial Sequence
<220> FEATURE:
<223> OTHER INFORMATION: KRT8 Preamplification and Amplification Reverse
      Primer

<400> SEQUENCE: 8
ccgctggtgg tcttcgtatg                                              20

<210> SEQ ID NO 9
<211> LENGTH: 17
<212> TYPE: DNA
<213> ORGANISM: Artificial Sequence
<220> FEATURE:
<223> OTHER INFORMATION: EPCAM Preamplification Forward Primer

<400> SEQUENCE: 9
gcaggtcctc gcgttcg                                                 17

<210> SEQ ID NO 10
<211> LENGTH: 22
<212> TYPE: DNA
<213> ORGANISM: Artificial Sequence
<220> FEATURE:
<223> OTHER INFORMATION: EPCAM Preamplification and Amplification
      Reverse Primer

<400> SEQUENCE: 10
tctcccaagt tttgagccat tc                                           22

<210> SEQ ID NO 11
<211> LENGTH: 24
<212> TYPE: DNA

```
<213> ORGANISM: Artificial Sequence
<220> FEATURE:
<223> OTHER INFORMATION: PTPRC Preamplification Forward Primer

<400> SEQUENCE: 11
gacatcatca cctagcagtt catg                                              24

<210> SEQ ID NO 12
<211> LENGTH: 19
<212> TYPE: DNA
<213> ORGANISM: Artificial Sequence
<220> FEATURE:
<223> OTHER INFORMATION: PTPRC Preamplification and Amplification
      Reverse Primer

<400> SEQUENCE: 12
cagtggggga aggtgttgg                                                    19

<210> SEQ ID NO 13
<211> LENGTH: 19
<212> TYPE: DNA
<213> ORGANISM: Artificial Sequence
<220> FEATURE:
<223> OTHER INFORMATION: VWF Preamplification Forward Primer

<400> SEQUENCE: 13
acacaggggg accaaagag                                                    19

<210> SEQ ID NO 14
<211> LENGTH: 19
<212> TYPE: DNA
<213> ORGANISM: Artificial Sequence
<220> FEATURE:
<223> OTHER INFORMATION: VWF Preamplification and Amplification Reverse
      Primer

<400> SEQUENCE: 14
gagatgcccg ttcacacca                                                    19

<210> SEQ ID NO 15
<211> LENGTH: 19
<212> TYPE: DNA
<213> ORGANISM: Artificial Sequence
<220> FEATURE:
<223> OTHER INFORMATION: PECAM1 Preamplification Forward Primer

<400> SEQUENCE: 15
tctcaacggt gacttgtgg                                                    19

<210> SEQ ID NO 16
<211> LENGTH: 21
<212> TYPE: DNA
<213> ORGANISM: Artificial Sequence
<220> FEATURE:
<223> OTHER INFORMATION: PECAM1 Preamplification and Amplification
      Reverse Primer

<400> SEQUENCE: 16
gttcttccca ttttgcaccg t                                                 21

<210> SEQ ID NO 17
<211> LENGTH: 18
<212> TYPE: DNA
<213> ORGANISM: Artificial Sequence
<220> FEATURE:
<223> OTHER INFORMATION: MCAM Preamplification and Amplification Forward
      Primer
```

```
<400> SEQUENCE: 17
ctcggtccca ggagtacc                                                        18

<210> SEQ ID NO 18
<211> LENGTH: 21
<212> TYPE: DNA
<213> ORGANISM: Artificial Sequence
<220> FEATURE:
<223> OTHER INFORMATION: MCAM Preamplification Reverse Primer

<400> SEQUENCE: 18
tgtacaaacc actcgactcc a                                                    21

<210> SEQ ID NO 19
<211> LENGTH: 19
<212> TYPE: DNA
<213> ORGANISM: Artificial Sequence
<220> FEATURE:
<223> OTHER INFORMATION: ITGA2B Preamplification Forward Primer

<400> SEQUENCE: 19
cttctatgca ggccccaat                                                       19

<210> SEQ ID NO 20
<211> LENGTH: 22
<212> TYPE: DNA
<213> ORGANISM: Artificial Sequence
<220> FEATURE:
<223> OTHER INFORMATION: ITGA2B Preamplification and Amplification
      Reverse Primer

<400> SEQUENCE: 20
agcctacatt tcgggtctca tc                                                   22

<210> SEQ ID NO 21
<211> LENGTH: 25
<212> TYPE: DNA
<213> ORGANISM: Artificial Sequence
<220> FEATURE:
<223> OTHER INFORMATION: CD34 Preamplification Forward Primer

<400> SEQUENCE: 21
ccttctgggt tcatgagtct tgaca                                                25

<210> SEQ ID NO 22
<211> LENGTH: 25
<212> TYPE: DNA
<213> ORGANISM: Artificial Sequence
<220> FEATURE:
<223> OTHER INFORMATION: CD34 Preamplification and Amplification Reverse
      Primer

<400> SEQUENCE: 22
tgtcgtttct gtgatgtttg ttgtg                                                25

<210> SEQ ID NO 23
<211> LENGTH: 23
<212> TYPE: DNA
<213> ORGANISM: Artificial Sequence
<220> FEATURE:
<223> OTHER INFORMATION: FOLH1 Preamplification Forward Primer

<400> SEQUENCE: 23
cggatattgt accacctttc agt                                                  23
```

-continued

<210> SEQ ID NO 24
<211> LENGTH: 20
<212> TYPE: DNA
<213> ORGANISM: Artificial Sequence
<220> FEATURE:
<223> OTHER INFORMATION: FOLH1 Preamplification and Amplification
      Reverse Primer

<400> SEQUENCE: 24
agcagggtcg gagtagagaa                                              20

<210> SEQ ID NO 25
<211> LENGTH: 22
<212> TYPE: DNA
<213> ORGANISM: Artificial Sequence
<220> FEATURE:
<223> OTHER INFORMATION: ENG Preamplification and Amplification Forward
      Primer

<400> SEQUENCE: 25
gtgacggtga aggtggaact ga                                           22

<210> SEQ ID NO 26
<211> LENGTH: 20
<212> TYPE: DNA
<213> ORGANISM: Artificial Sequence
<220> FEATURE:
<223> OTHER INFORMATION: ENG Preamplification Reverse Primer

<400> SEQUENCE: 26
ttgaggtgtg tctgggagct                                              20

<210> SEQ ID NO 27
<211> LENGTH: 23
<212> TYPE: DNA
<213> ORGANISM: Artificial Sequence
<220> FEATURE:
<223> OTHER INFORMATION: KDR Preamplification and Amplification Forward
      Primer

<400> SEQUENCE: 27
gaaatgacac tggagcctac aag                                          23

<210> SEQ ID NO 28
<211> LENGTH: 21
<212> TYPE: DNA
<213> ORGANISM: Artificial Sequence
<220> FEATURE:
<223> OTHER INFORMATION: KDR Preamplification Reverse Primer

<400> SEQUENCE: 28
aatggacccg agacatggaa t                                            21

<210> SEQ ID NO 29
<211> LENGTH: 22
<212> TYPE: DNA
<213> ORGANISM: Artificial Sequence
<220> FEATURE:
<223> OTHER INFORMATION: CDH5 Preamplification Forward Primer

<400> SEQUENCE: 29
gttcacgcat cggttgttca at                                           22

<210> SEQ ID NO 30
<211> LENGTH: 20
<212> TYPE: DNA

```
<213> ORGANISM: Artificial Sequence
<220> FEATURE:
<223> OTHER INFORMATION: CDH5 Preamplification and Amplification Reverse
      Primer

<400> SEQUENCE: 30
gcctgcttct ctcggtccaa                                              20

<210> SEQ ID NO 31
<211> LENGTH: 23
<212> TYPE: DNA
<213> ORGANISM: Artificial Sequence
<220> FEATURE:
<223> OTHER INFORMATION: TEK Preamplification and Amplification Forward
      Primer

<400> SEQUENCE: 31
cttatttctg tgaagggcga gtt                                          23

<210> SEQ ID NO 32
<211> LENGTH: 22
<212> TYPE: DNA
<213> ORGANISM: Artificial Sequence
<220> FEATURE:
<223> OTHER INFORMATION: TEK Preamplification Reverse Primer

<400> SEQUENCE: 32
ctcccttgtc cacagtcata gt                                           22

<210> SEQ ID NO 33
<211> LENGTH: 25
<212> TYPE: DNA
<213> ORGANISM: Artificial Sequence
<220> FEATURE:
<223> OTHER INFORMATION: ANGPT2 Preamplification Forward Primer

<400> SEQUENCE: 33
aacactccct ctcgacaaac aaatt                                        25

<210> SEQ ID NO 34
<211> LENGTH: 24
<212> TYPE: DNA
<213> ORGANISM: Artificial Sequence
<220> FEATURE:
<223> OTHER INFORMATION: ANGPT2 Preamplification and Amplification
      Reverse Primer

<400> SEQUENCE: 34
ctgtagttgg atgatgtgct tgtc                                         24

<210> SEQ ID NO 35
<211> LENGTH: 23
<212> TYPE: DNA
<213> ORGANISM: Artificial Sequence
<220> FEATURE:
<223> OTHER INFORMATION: SERPINE1 Amplification Forward Primer

<400> SEQUENCE: 35
agaacttcag gatgcagatg tct                                          23

<210> SEQ ID NO 36
<211> LENGTH: 21
<212> TYPE: DNA
<213> ORGANISM: Artificial Sequence
<220> FEATURE:
<223> OTHER INFORMATION: VIM Amplification Reverse Primer
```

<400> SEQUENCE: 36
tgtaccattc ttctgcctcc t    21

<210> SEQ ID NO 37
<211> LENGTH: 22
<212> TYPE: DNA
<213> ORGANISM: Artificial Sequence
<220> FEATURE:
<223> OTHER INFORMATION: FOXC1 Amplification Reverse Primer

<400> SEQUENCE: 37
gagggatatt ctgttcgctg gt    22

<210> SEQ ID NO 38
<211> LENGTH: 17
<212> TYPE: DNA
<213> ORGANISM: Artificial Sequence
<220> FEATURE:
<223> OTHER INFORMATION: KRT8 Amplification Forward Primer

<400> SEQUENCE: 38
gctggagggc gaggaga    17

<210> SEQ ID NO 39
<211> LENGTH: 20
<212> TYPE: DNA
<213> ORGANISM: Artificial Sequence
<220> FEATURE:
<223> OTHER INFORMATION: EPCAM Amplification Forward Primer

<400> SEQUENCE: 39
ccgcagctca ggaagaatgt    20

<210> SEQ ID NO 40
<211> LENGTH: 21
<212> TYPE: DNA
<213> ORGANISM: Artificial Sequence
<220> FEATURE:
<223> OTHER INFORMATION: PTPRC Amplification Forward Primer

<400> SEQUENCE: 40
caacagtgga gaaaggacgc a    21

<210> SEQ ID NO 41
<211> LENGTH: 20
<212> TYPE: DNA
<213> ORGANISM: Artificial Sequence
<220> FEATURE:
<223> OTHER INFORMATION: VWF Amplification Forward Primer

<400> SEQUENCE: 41
tgcctccaaa gggctgtatc    20

<210> SEQ ID NO 42
<211> LENGTH: 21
<212> TYPE: DNA
<213> ORGANISM: Artificial Sequence
<220> FEATURE:
<223> OTHER INFORMATION: PECAM1 Amplification Forward Primer

<400> SEQUENCE: 42
cagtcttcac tctcaggatg c    21

<210> SEQ ID NO 43
<211> LENGTH: 22

```
<212> TYPE: DNA
<213> ORGANISM: Artificial Sequence
<220> FEATURE:
<223> OTHER INFORMATION: MCAM Amplification Reverse Primer

<400> SEQUENCE: 43
cggccattct tgtaccagat ga                                              22

<210> SEQ ID NO 44
<211> LENGTH: 16
<212> TYPE: DNA
<213> ORGANISM: Artificial Sequence
<220> FEATURE:
<223> OTHER INFORMATION: ITGA2B Amplification Forward Primer

<400> SEQUENCE: 44
ggcggcgtgt tcctgt                                                     16

<210> SEQ ID NO 45
<211> LENGTH: 22
<212> TYPE: DNA
<213> ORGANISM: Artificial Sequence
<220> FEATURE:
<223> OTHER INFORMATION: CD34 Amplification Forward Primer

<400> SEQUENCE: 45
ctaccccaga gttacctacc ca                                              22

<210> SEQ ID NO 46
<211> LENGTH: 20
<212> TYPE: DNA
<213> ORGANISM: Artificial Sequence
<220> FEATURE:
<223> OTHER INFORMATION: FOLH1 Amplification Forward Primer

<400> SEQUENCE: 46
ccagagggcg atctagtgta                                                 20

<210> SEQ ID NO 47
<211> LENGTH: 24
<212> TYPE: DNA
<213> ORGANISM: Artificial Sequence
<220> FEATURE:
<223> OTHER INFORMATION: ENG Amplification Reverse Primer

<400> SEQUENCE: 47
agtattctcc agtggtccag atct                                            24

<210> SEQ ID NO 48
<211> LENGTH: 21
<212> TYPE: DNA
<213> ORGANISM: Artificial Sequence
<220> FEATURE:
<223> OTHER INFORMATION: KDR Amplification Reverse Primer

<400> SEQUENCE: 48
tgttggtcac taacagaagc a                                               21

<210> SEQ ID NO 49
<211> LENGTH: 20
<212> TYPE: DNA
<213> ORGANISM: Artificial Sequence
<220> FEATURE:
<223> OTHER INFORMATION: CDH5 Amplification Forward Primer

<400> SEQUENCE: 49
```

```
cacgcctctg tcatgtacca                                              20

<210> SEQ ID NO 50
<211> LENGTH: 21
<212> TYPE: DNA
<213> ORGANISM: Artificial Sequence
<220> FEATURE:
<223> OTHER INFORMATION: TEK Amplification Reverse Primer

<400> SEQUENCE: 50
gtagctggta ggaaggaagc t                                            21

<210> SEQ ID NO 51
<211> LENGTH: 24
<212> TYPE: DNA
<213> ORGANISM: Artificial Sequence
<220> FEATURE:
<223> OTHER INFORMATION: ANGPT2 Amplification Forward Primer

<400> SEQUENCE: 51
ggaccagacc agtgaaataa acaa                                         24

<210> SEQ ID NO 52
<211> LENGTH: 20
<212> TYPE: DNA
<213> ORGANISM: Artificial Sequence
<220> FEATURE:
<223> OTHER INFORMATION: KRT18 Preamplification Forward Primer

<400> SEQUENCE: 52
tgctcaccac acagtctgat                                              20

<210> SEQ ID NO 53
<211> LENGTH: 20
<212> TYPE: DNA
<213> ORGANISM: Artificial Sequence
<220> FEATURE:
<223> OTHER INFORMATION: KRT18 Preamplification Reverse Primer

<400> SEQUENCE: 53
cactttgcca tccactagcc                                              20

<210> SEQ ID NO 54
<211> LENGTH: 20
<212> TYPE: DNA
<213> ORGANISM: Artificial Sequence
<220> FEATURE:
<223> OTHER INFORMATION: KRT19 Preamplification Forward Primer

<400> SEQUENCE: 54
cagccactac tacacgacca                                              20

<210> SEQ ID NO 55
<211> LENGTH: 18
<212> TYPE: DNA
<213> ORGANISM: Artificial Sequence
<220> FEATURE:
<223> OTHER INFORMATION: KRT19 Preamplification Reverse Primer

<400> SEQUENCE: 55
cgttgatgtc ggcctcca                                                18

<210> SEQ ID NO 56
<211> LENGTH: 20
<212> TYPE: DNA
<213> ORGANISM: Artificial Sequence
```

```
<220> FEATURE:
<223> OTHER INFORMATION: KRT18 Amplification Forward Primer

<400> SEQUENCE: 56
tggaggaccg ctacgcccta                                              20

<210> SEQ ID NO 57
<211> LENGTH: 20
<212> TYPE: DNA
<213> ORGANISM: Artificial Sequence
<220> FEATURE:
<223> OTHER INFORMATION: KRT18 Amplification Reverse Primer

<400> SEQUENCE: 57
ccaaggcatc accaagacta                                              20

<210> SEQ ID NO 58
<211> LENGTH: 20
<212> TYPE: DNA
<213> ORGANISM: Artificial Sequence
<220> FEATURE:
<223> OTHER INFORMATION: KRT19 Preamplification Forward Primer

<400> SEQUENCE: 58
tgcgggacaa gattcttggt                                              20
```